(12) United States Patent
Levien et al.

(10) Patent No.: US 9,125,987 B2
(45) Date of Patent: Sep. 8, 2015

(54) UNMANNED DEVICE UTILIZATION METHODS AND SYSTEMS

(75) Inventors: Royce A. Levien, Lexington, MA (US);
Richard T. Lord, Tacoma, WA (US);
Robert W. Lord, Seattle, WA (US);
Mark A. Malamud, Seattle, WA (US);
John D. Rinaldo, Jr., Bellevue, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 607 days.

(21) Appl. No.: 13/551,320

(22) Filed: Jul. 17, 2012

(65) Prior Publication Data

US 2014/0025235 A1 Jan. 23, 2014

Related U.S. Application Data

(63) Continuation-in-part of application No. 13/551,266, filed on Jul. 17, 2012, and a continuation-in-part of application No. 13/551,287, filed on Jul. 17, 2012, and a continuation-in-part of application No. 13/551,301, filed on Jul. 17, 2012, and a continuation-in-part of application No. 13/551,334, filed on Jul. 17, 2012.

(51) Int. Cl.
*G06F 7/76* (2006.01)
*A61M 5/20* (2006.01)
*G05D 1/00* (2006.01)
*G06F 19/00* (2011.01)

(52) U.S. Cl.
CPC . *A61M 5/20* (2013.01); *G05D 1/00* (2013.01); *G06F 7/76* (2013.01); *B64C 2201/00* (2013.01); *B64C 2201/12* (2013.01); *B64C 2201/126* (2013.01); *B64C 2201/128* (2013.01); *B64C 2201/141* (2013.01); *G06F 19/3456* (2013.01)

(58) Field of Classification Search
CPC ................ B64C 2201/128; B64C 2201/141
See application file for complete search history.

(56) References Cited

U.S. PATENT DOCUMENTS

| 5,521,817 | A |   | 5/1996  | Burdoin et al. |
|-----------|---|---|---------|----------------|
| 5,798,733 | A | * | 8/1998  | Ethridge .................. 342/357.34 |
| 6,163,745 | A |   | 12/2000 | Purchase et al. |
| 6,176,451 | B1 |  | 1/2001  | Drymon |
| 6,335,910 | B1 |  | 1/2002  | Yoshizawa et al. |
| 6,470,989 | B1 |  | 10/2002 | Puputti et al. |

(Continued)

FOREIGN PATENT DOCUMENTS

| CN | 102120489 A | 7/2011 |
|----|-------------|--------|
| JP | 2000/180100 | 6/2000 |

(Continued)

OTHER PUBLICATIONS

Fischer, Markus; "A robot that flies like a bird" Online Video Clip; TED Conferences, LLC; Jul. 2011; accessed on Sep. 11, 2012; located a http://www.ted.com/talks/a_robot_that_flies_like_a_bird.html.

(Continued)

*Primary Examiner* — Helal A Algahaim
*Assistant Examiner* — Paul Castro
(74) *Attorney, Agent, or Firm* — Suiter Swantz pc llo

(57) ABSTRACT

Structures and protocols are presented for configuring an unmanned aerial device to perform a task, alone or in combination with other entities, or for using data resulting from such a configuration or performance.

29 Claims, 20 Drawing Sheets

(56) References Cited

U.S. PATENT DOCUMENTS

| | | |
|---|---|---|
| 6,574,538 B2 | 6/2003 | Sasaki |
| 6,923,404 B1 | 8/2005 | Liu et al. |
| 7,392,151 B2 | 6/2008 | Makela |
| 7,581,702 B2 | 9/2009 | Olson et al. |
| 7,631,834 B1 | 12/2009 | Johnson et al. |
| 7,725,232 B2 | 5/2010 | Makela et al. |
| 8,565,913 B2 | 10/2013 | Emanuel et al. |
| 8,639,396 B1 | 1/2014 | Hirsch et al. |
| 8,688,598 B1 | 4/2014 | Shakes et al. |
| 8,930,044 B1 | 1/2015 | Peeters et al. |
| 8,948,935 B1 | 2/2015 | Peeters et al. |
| 8,983,682 B1 | 3/2015 | Peeters et al. |
| 9,022,324 B1 | 5/2015 | Abhyanker |
| 2003/0200726 A1 | 10/2003 | Rast |
| 2004/0134336 A1 | 7/2004 | Solomon |
| 2004/0143602 A1 | 7/2004 | Ruiz et al. |
| 2006/0197835 A1 | 9/2006 | Anderson et al. |
| 2006/0221328 A1 | 10/2006 | Rouly |
| 2006/0249622 A1 | 11/2006 | Steele |
| 2007/0061041 A1 | 3/2007 | Zweig |
| 2007/0180318 A1 | 8/2007 | Morozumi |
| 2007/0192910 A1* | 8/2007 | Vu et al. ............ 901/17 |
| 2007/0225993 A1 | 9/2007 | Moore |
| 2009/0008499 A1* | 1/2009 | Shaw ............ 244/17.23 |
| 2009/0050750 A1* | 2/2009 | Goossen ............ 244/76 R |
| 2009/0055019 A1 | 2/2009 | Stiehl et al. |
| 2009/0198371 A1 | 8/2009 | Emanuel et al. |
| 2009/0207048 A1 | 8/2009 | He et al. |
| 2009/0232355 A1 | 9/2009 | Minear et al. |
| 2009/0299551 A1 | 12/2009 | So et al. |
| 2009/0322877 A1 | 12/2009 | Tigner |
| 2010/0004798 A1 | 1/2010 | Bodin et al. |
| 2010/0084513 A1 | 4/2010 | Gariepy et al. |
| 2010/0224732 A1 | 9/2010 | Olson et al. |
| 2010/0250022 A1 | 9/2010 | Hines et al. |
| 2011/0049290 A1 | 3/2011 | Seydoux et al. |
| 2011/0084162 A1 | 4/2011 | Goossen et al. |
| 2011/0102197 A1 | 5/2011 | Herwich |
| 2011/0139928 A1 | 6/2011 | Morris et al. |
| 2011/0221692 A1 | 9/2011 | Seydoux et al. |
| 2011/0288696 A1 | 11/2011 | Lefebure |
| 2012/0091260 A1 | 4/2012 | Callou |
| 2012/0152654 A1* | 6/2012 | Marcus ............ 182/129 |
| 2012/0200703 A1 | 8/2012 | Nadir et al. |
| 2012/0215382 A1 | 8/2012 | Lee et al. |
| 2012/0224732 A1 | 9/2012 | Secall et al. |
| 2012/0226394 A1 | 9/2012 | Marcus |
| 2012/0271491 A1* | 10/2012 | Spata ............ 701/3 |
| 2012/0290152 A1* | 11/2012 | Cheung et al. ............ 701/2 |
| 2012/0304085 A1 | 11/2012 | Kim et al. |
| 2012/0309288 A1 | 12/2012 | Lu |
| 2012/0320510 A1 | 12/2012 | Varga et al. |
| 2013/0006675 A1 | 1/2013 | Bowne et al. |
| 2013/0314502 A1 | 11/2013 | Urbach et al. |
| 2014/0032034 A1* | 1/2014 | Raptopoulos et al. ............ 701/25 |
| 2014/0172727 A1 | 1/2014 | Abhyanker et al. |
| 2014/0188776 A1 | 7/2014 | Shuster et al. |
| 2014/0316614 A1 | 10/2014 | Newman |
| 2014/0347482 A1 | 11/2014 | Weinmann et al. |
| 2015/0093956 A1 | 4/2015 | Mielniczek |
| 2015/0120094 A1 | 4/2015 | Kimchi et al. |
| 2015/0120126 A1 | 4/2015 | So et al. |

FOREIGN PATENT DOCUMENTS

| | | |
|---|---|---|
| KR | 101339183 | 12/2013 |
| NL | 1032982 C2 | 4/2008 |
| WO | WO 2012/047977 A1 | 12/2012 |

OTHER PUBLICATIONS

Kumar, Vijay; "Robots that fly . . . and cooperate" Online Video Clip; TED Conferences, LLC; Feb. 2012; accessed on Sep. 11, 2012; located at http://www.ted.com/talks/vijay_kumar_robots_that_fly_and_cooperate.html.

Lermusiaux, Pierre; "Optimal paths for automated underwater vehicles (AUVs)" Online Video Clip; MITNewsOffice; published on Mar. 8, 2012; accessed on Sep. 11, 2012; located at http://www.youtube.com/watch?v=OtnOgefsm0w; also located at http://www.engadget.com/2012/03/12/mit-software-optimizes-paths-for-automated-undersea-vehicles/.

Song, Yale; "Guiding robot planes with hand gestures" Online Video Clip; MITNewsOffice; published on Mar. 13, 2012; accessed on Sep. 11, 2012; also located at http://www.youtube.com/watch?v=VjVmLA8_uHY; also located at http://web.mit.edu/newsoffice/2012/robots-hand-gestures-0314.html.

Yu et al.; "FlyingBuddy2: A Brain-controlled Assistant for the Handicapped" Online Video Clip; Pervasive Computing Group At CCNT Lab, Zhejiang University, China; Presented at Ubicomp 2012; accessed on Sep. 11, 2012; located at http://www.youtube.com/watch?v=JH96O5niEnl&feature=youtu.be; also located at http://www.wired.com/gadgetlab/2012/08/zhejiang-university-china-brain-controlled-quadcopter/.

* cited by examiner

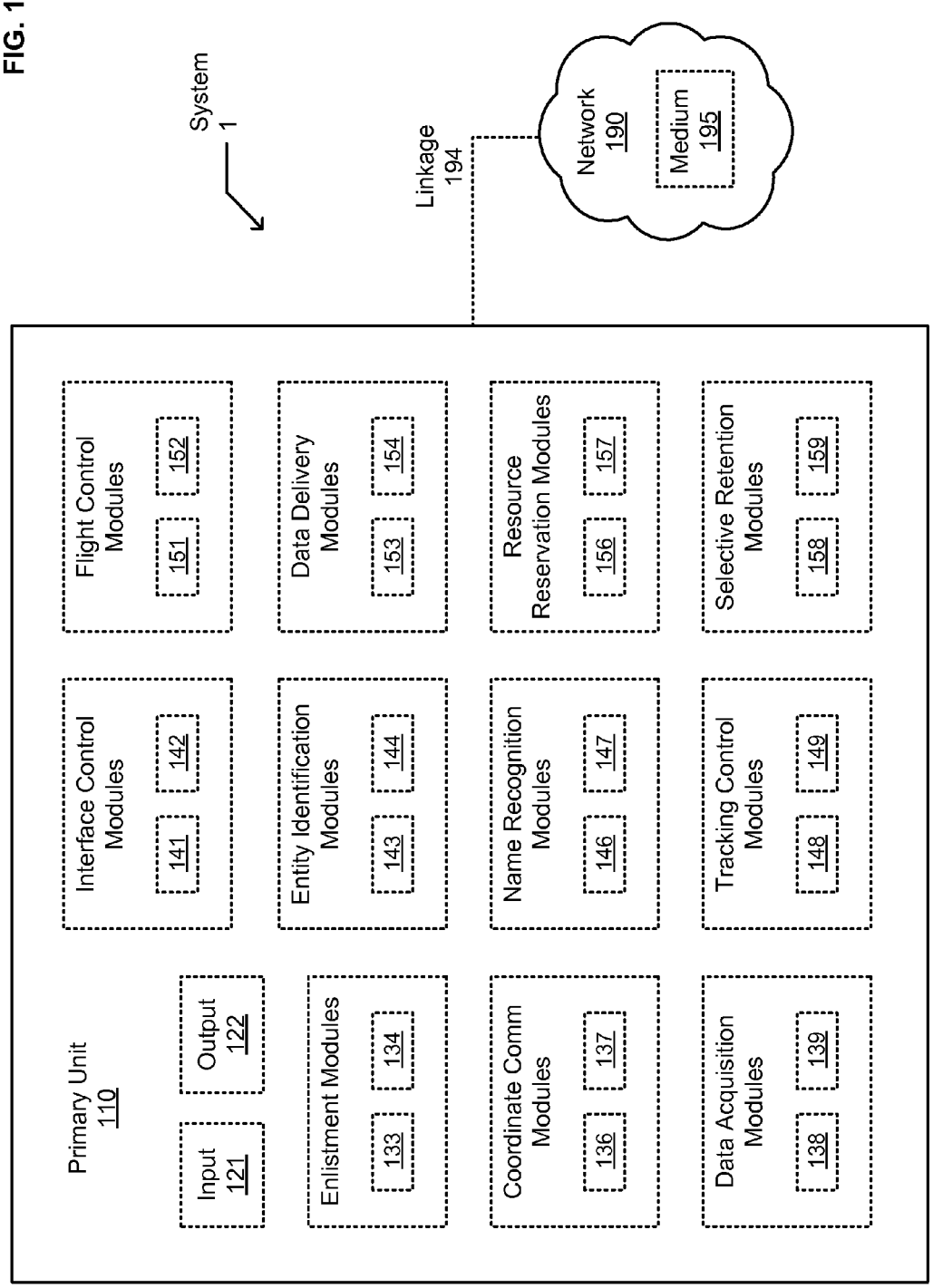

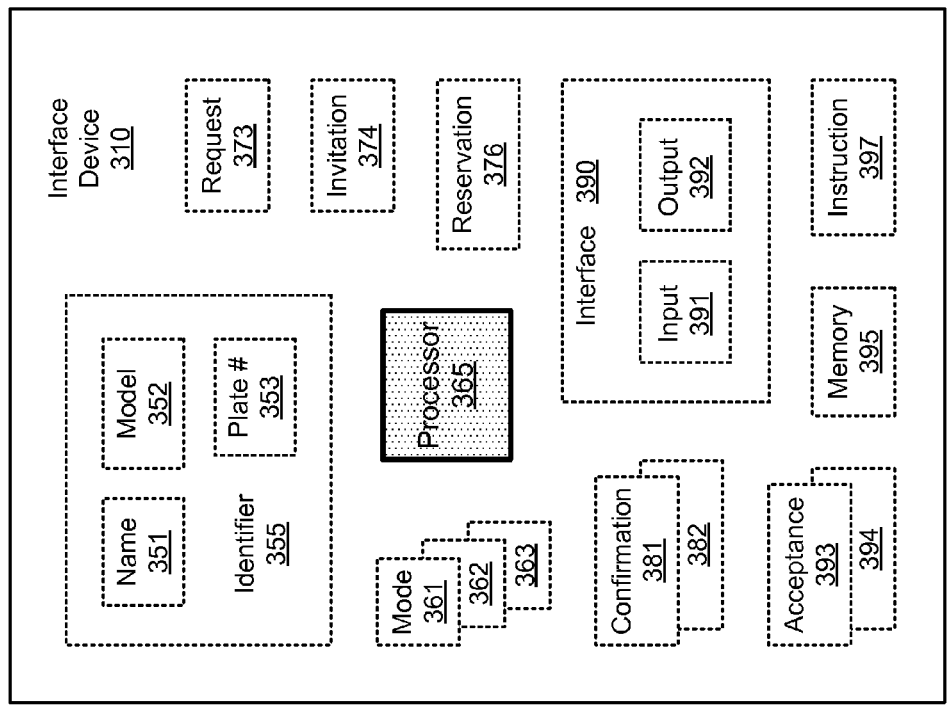
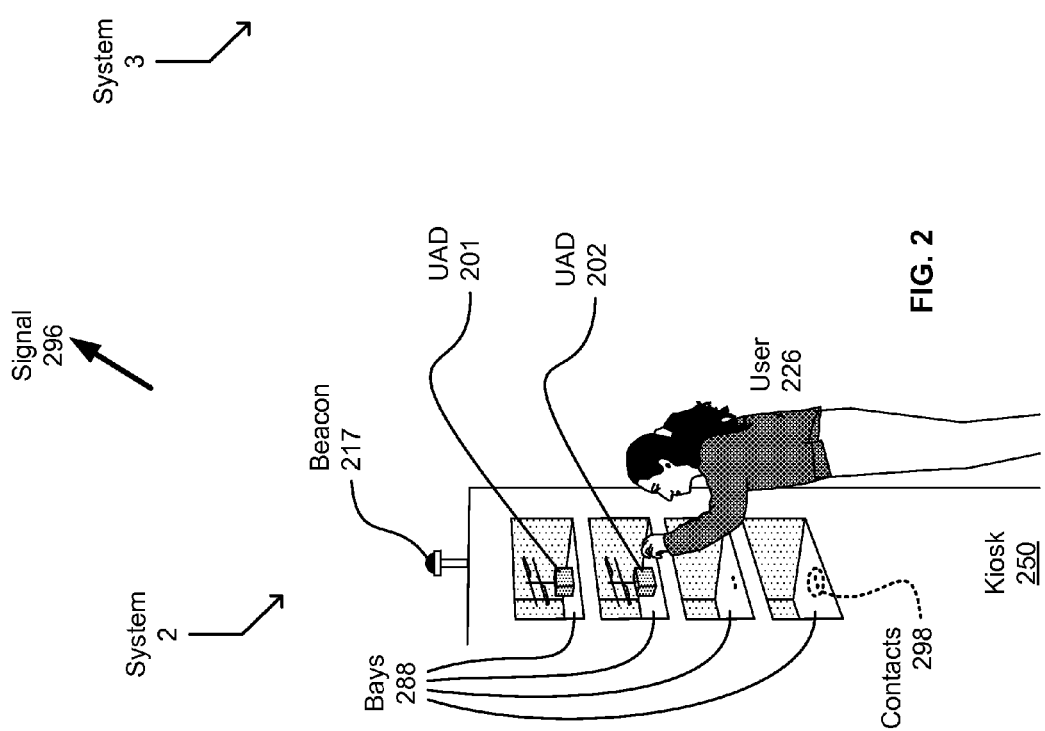

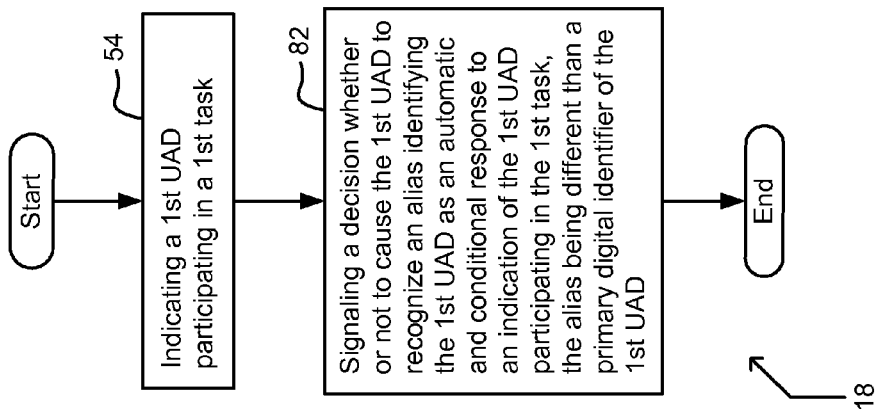
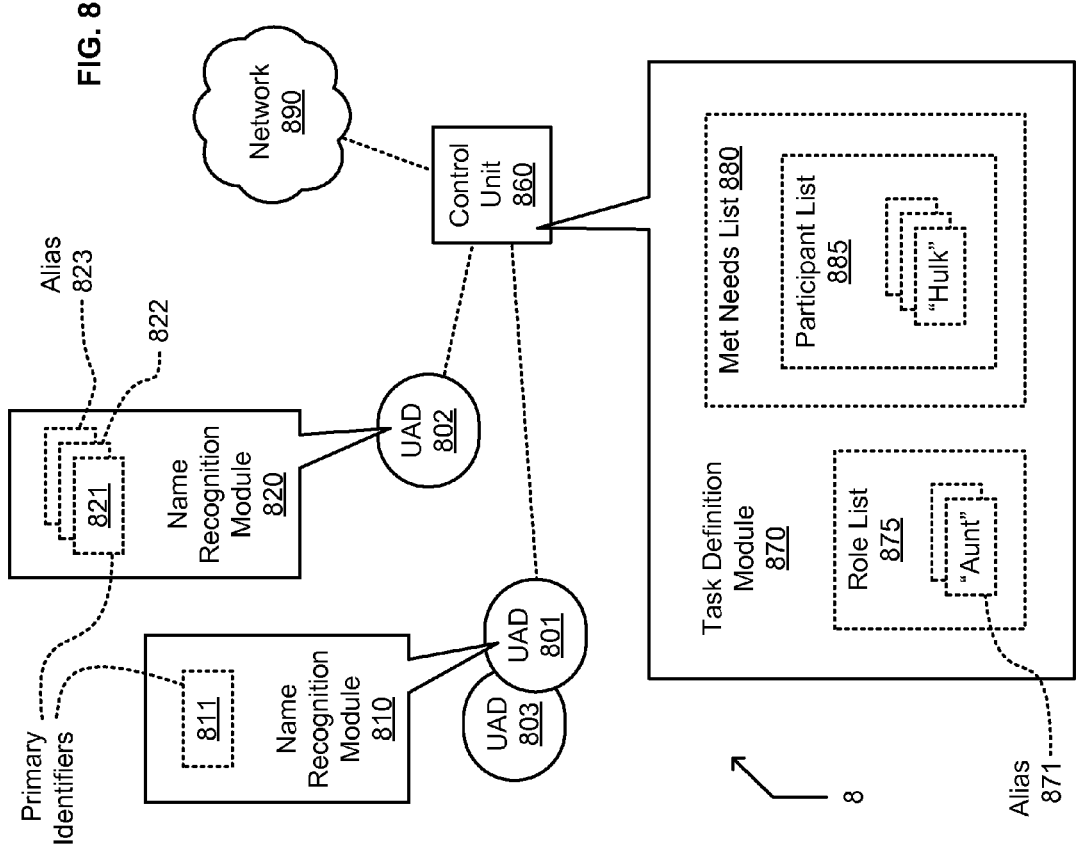

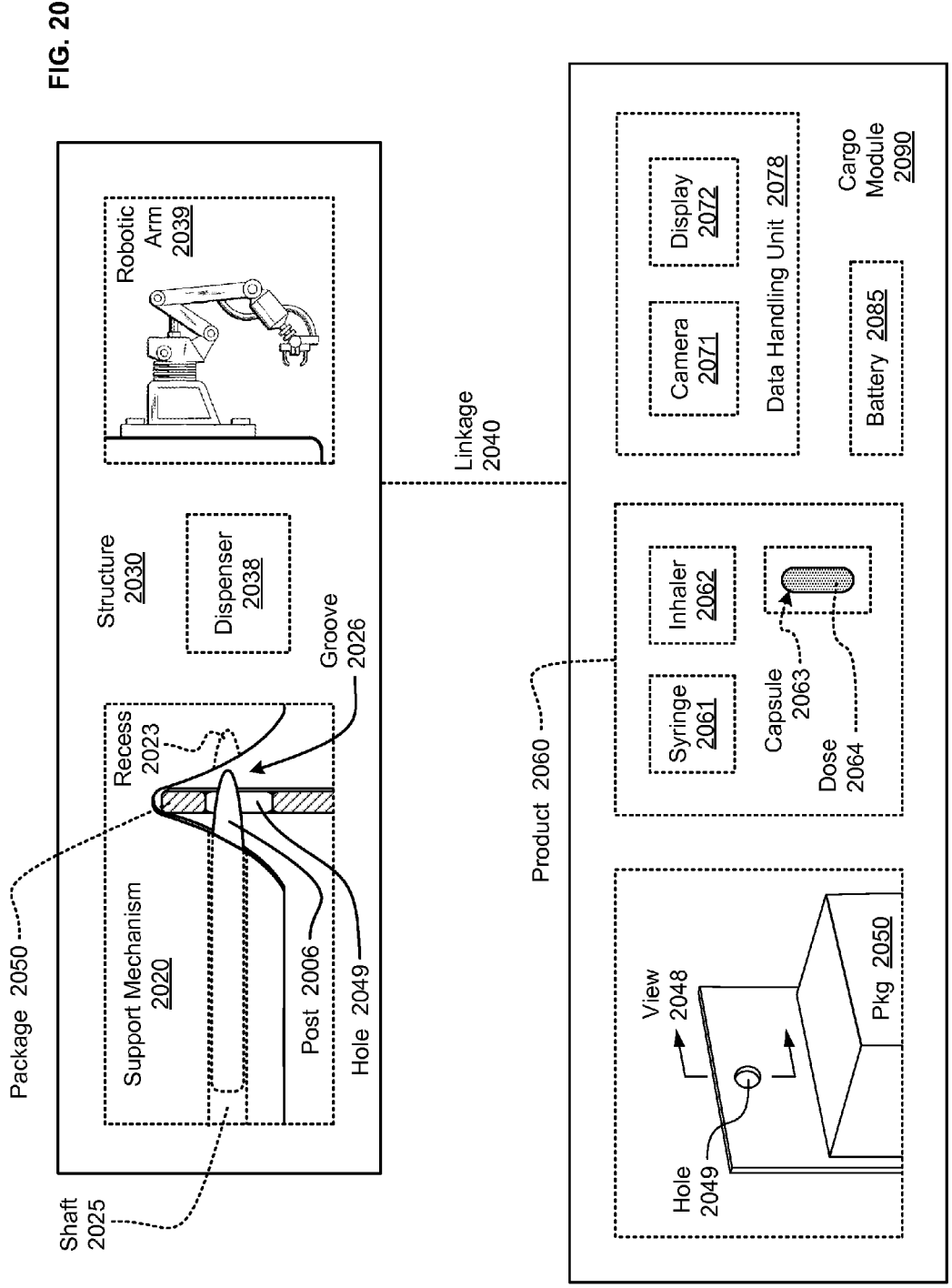

UNMANNED DEVICE UTILIZATION METHODS AND SYSTEMS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/551,266, U.S. patent application Ser. No. 13/551,287, U.S. patent application Ser. No. 13/551,301, and U.S. patent application Ser. No. 13/551,334, each entitled UNMANNED DEVICE UTILIZATION METHODS AND SYSTEMS, naming Royce A. Levien, Richard T. Lord, Robert W. Lord, Mark A. Malamud, John D. Rinaldo, Jr., and Lowell L. Wood, Jr., as inventors, filed 17 Jul. 2012, each of which is currently co-pending or is an application of which a currently co-pending application is entitled to the benefit of the filing date.

For purposes of the USPTO extra-statutory requirements, the present application claims benefit of priority of U.S. patent application Ser. No. 13/551,266, U.S. patent application Ser. No. 13/551,287, U.S. patent application Ser. No. 13/551,301, and U.S. patent application Ser. No. 13/551,334, each entitled UNMANNED DEVICE UTILIZATION METHODS AND SYSTEMS, naming Royce A. Levien, Richard T. Lord, Robert W. Lord, Mark A. Malamud, John D. Rinaldo, Jr., and Lowell L. Wood, Jr., as inventors, filed 17 Jul. 2012, each of which was filed within the twelve months preceding the filing date of the present application or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

BACKGROUND

The claims, description, and drawings of this application may describe one or more of the instant technologies in operational/functional language, for example as a set of operations to be performed by a computer. Such operational/functional description in most instances would be understood by one skilled the art as specifically-configured hardware (e.g., because a general purpose computer in effect becomes a special purpose computer once it is programmed to perform particular functions pursuant to instructions from program software).

Importantly, although the operational/functional descriptions described herein are understandable by the human mind, they are not abstract ideas of the operations/functions divorced from computational implementation of those operations/functions. Rather, the operations/functions represent a specification for the massively complex computational machines or other means. As discussed in detail below, the operational/functional language must be read in its proper technological context, i.e., as concrete specifications for physical implementations.

The logical operations/functions described herein are a distillation of machine specifications or other physical mechanisms specified by the operations/functions such that the otherwise inscrutable machine specifications may be comprehensible to the human mind. The distillation also allows one of skill in the art to adapt the operational/functional description of the technology across many different specific vendors' hardware configurations or platforms, without being limited to specific vendors' hardware configurations or platforms.

Some of the present technical description (e.g., detailed description, drawings, claims, etc.) may be set forth in terms of logical operations/functions. As described in more detail in the following paragraphs, these logical operations/functions are not representations of abstract ideas, but rather representative of static or sequenced specifications of various hardware elements. Differently stated, unless context dictates otherwise, the logical operations/functions will be understood by those of skill in the art to be representative of static or sequenced specifications of various hardware elements. This is true because tools available to one of skill in the art to implement technical disclosures set forth in operational/functional formats—tools in the form of a high-level programming language (e.g., C, java, visual basic), etc.), or tools in the form of Very high speed Hardware Description Language ("VHDL," which is a language that uses text to describe logic circuits)—are generators of static or sequenced specifications of various hardware configurations. This fact is sometimes obscured by the broad term "software," but, as shown by the following explanation, those skilled in the art understand that what is termed "software" is a shorthand for a massively complex interchaining/specification of ordered-matter elements. The term "ordered-matter elements" may refer to physical components of computation, such as assemblies of electronic logic gates, molecular computing logic constituents, quantum computing mechanisms, etc.

For example, a high-level programming language is a programming language with strong abstraction, e.g., multiple levels of abstraction, from the details of the sequential organizations, states, inputs, outputs, etc., of the machines that a high-level programming language actually specifies. See, e.g., Wikipedia, High-level programming language, http://en.wikipedia.org/wiki/High-level_programming_language (as of Jun. 5, 2012, 21:00 GMT). In order to facilitate human comprehension, in many instances, high-level programming languages resemble or even share symbols with natural languages. See, e.g., Wikipedia, Natural language, http://en.wikipedia.org/wiki/Natural_language (as of Jun. 5, 2012, 21:00 GMT).

It has been argued that because high-level programming languages use strong abstraction (e.g., that they may resemble or share symbols with natural languages), they are therefore a "purely mental construct." (e.g., that "software"—a computer program or computer programming—is somehow an ineffable mental construct, because at a high level of abstraction, it can be conceived and understood in the human mind). This argument has been used to characterize technical description in the form of functions/operations as somehow "abstract ideas." In fact, in technological arts (e.g., the information and communication technologies) this is not true.

The fact that high-level programming languages use strong abstraction to facilitate human understanding should not be taken as an indication that what is expressed is an abstract idea. In fact, those skilled in the art understand that just the opposite is true. If a high-level programming language is the tool used to implement a technical disclosure in the form of functions/operations, those skilled in the art will recognize that, far from being abstract, imprecise, "fuzzy," or "mental" in any significant semantic sense, such a tool is instead a near incomprehensibly precise sequential specification of specific computational machines—the parts of which are built up by activating/selecting such parts from typically more general computational machines over time (e.g., clocked time). This fact is sometimes obscured by the superficial similarities between high-level programming languages and natural languages. These superficial similarities also may cause a glossing over of the fact that high-level programming language implementations ultimately perform valuable work by creating/controlling many different computational machines.

The many different computational machines that a high-level programming language specifies are almost unimaginably complex. At base, the hardware used in the computational machines typically consists of some type of ordered matter (e.g., traditional electronic devices (e.g., transistors), deoxyribonucleic acid (DNA), quantum devices, mechanical switches, optics, fluidics, pneumatics, optical devices (e.g., optical interference devices), molecules, etc.) that are arranged to form logic gates. Logic gates are typically physical devices that may be electrically, mechanically, chemically, or otherwise driven to change physical state in order to create a physical reality of Boolean logic.

Logic gates may be arranged to form logic circuits, which are typically physical devices that may be electrically, mechanically, chemically, or otherwise driven to create a physical reality of certain logical functions. Types of logic circuits include such devices as multiplexers, registers, arithmetic logic units (ALUs), computer memory, etc., each type of which may be combined to form yet other types of physical devices, such as a central processing unit (CPU)—the best known of which is the microprocessor. A modern microprocessor will often contain more than one hundred million logic gates in its many logic circuits (and often more than a billion transistors). See, e.g., Wikipedia, Logic gates, http://en.wikipedia.org/wiki/Logic_gates (as of Jun. 5, 2012, 21:03 GMT).

The logic circuits forming the microprocessor are arranged to provide a microarchitecture that will carry out the instructions defined by that microprocessor's defined Instruction Set Architecture. The Instruction Set Architecture is the part of the microprocessor architecture related to programming, including the native data types, instructions, registers, addressing modes, memory architecture, interrupt and exception handling, and external Input/Output. See, e.g., Wikipedia, Computer architecture, http://en.wikipedia.org/wiki/Computer_architecture (as of Jun. 5, 2012, 21:03 GMT).

The Instruction Set Architecture includes a specification of the machine language that can be used by programmers to use/control the microprocessor. Since the machine language instructions are such that they may be executed directly by the microprocessor, typically they consist of strings of binary digits, or bits. For example, a typical machine language instruction might be many bits long (e.g., 32, 64, or 128 bit strings are currently common). A typical machine language instruction might take the form "11110000101011110000111100111111" (a 32 bit instruction).

It is significant here that, although the machine language instructions are written as sequences of binary digits, in actuality those binary digits specify physical reality. For example, if certain semiconductors are used to make the operations of Boolean logic a physical reality, the apparently mathematical bits "1" and "0" in a machine language instruction actually constitute a shorthand that specifies the application of specific voltages to specific wires. For example, in some semiconductor technologies, the binary number "1" (e.g., logical "1") in a machine language instruction specifies around +5 volts applied to a specific "wire" (e.g., metallic traces on a printed circuit board) and the binary number "0" (e.g., logical "0") in a machine language instruction specifies around −5 volts applied to a specific "wire." In addition to specifying voltages of the machines' configuration, such machine language instructions also select out and activate specific groupings of logic gates from the millions of logic gates of the more general machine. Thus, far from abstract mathematical expressions, machine language instruction programs, even though written as a string of zeros and ones, specify many, many constructed physical machines or physical machine states.

Machine language is typically incomprehensible by most humans (e.g., the above example was just ONE instruction, and some personal computers execute more than two billion instructions every second). See, e.g., Wikipedia, Instructions per second, http://en.wikipedia.org/wiki/Instructions_per_second (as of Jun. 5, 2012, 21:04 GMT).

Thus, programs written in machine language—which may be tens of millions of machine language instructions long—are incomprehensible. In view of this, early assembly languages were developed that used mnemonic codes to refer to machine language instructions, rather than using the machine language instructions' numeric values directly (e.g., for performing a multiplication operation, programmers coded the abbreviation "mult," which represents the binary number "011000" in MIPS machine code). While assembly languages were initially a great aid to humans controlling the microprocessors to perform work, in time the complexity of the work that needed to be done by the humans outstripped the ability of humans to control the microprocessors using merely assembly languages.

At this point, it was noted that the same tasks needed to be done over and over, and the machine language necessary to do those repetitive tasks was the same. In view of this, compilers were created. A compiler is a device that takes a statement that is more comprehensible to a human than either machine or assembly language, such as "add 2+2 and output the result," and translates that human understandable statement into a complicated, tedious, and immense machine language code (e.g., millions of 32, 64, or 128 bit length strings). Compilers thus translate high-level programming language into machine language.

This compiled machine language, as described above, is then used as the technical specification which sequentially constructs and causes the interoperation of many different computational machines such that humanly useful, tangible, and concrete work is done. For example, as indicated above, such machine language—the compiled version of the higher-level language—functions as a technical specification which selects out hardware logic gates, specifies voltage levels, voltage transition timings, etc., such that the humanly useful work is accomplished by the hardware.

Thus, a functional/operational technical description, when viewed by one of skill in the art, is far from an abstract idea. Rather, such a functional/operational technical description, when understood through the tools available in the art such as those just described, is instead understood to be a humanly understandable representation of a hardware specification, the complexity and specificity of which far exceeds the comprehension of most any one human. With this in mind, those skilled in the art will understand that any such operational/functional technical descriptions—in view of the disclosures herein and the knowledge of those skilled in the art—may be understood as operations made into physical reality by (a) one or more interchained physical machines, (b) interchained logic gates configured to create one or more physical machine(s) representative of sequential/combinatorial logic(s), (c) interchained ordered matter making up logic gates (e.g., interchained electronic devices (e.g., transistors), DNA, quantum devices, mechanical switches, optics, fluidics, pneumatics, molecules, etc.) that create physical reality representative of logic(s), or (d) virtually any combination of the foregoing. Indeed, any physical object which has a stable, measurable, and changeable state may be used to construct a machine based on the above technical description. Charles Babbage, for example, constructed the first computer out of wood and powered by cranking a handle.

Thus, far from being understood as an abstract idea, those skilled in the art will recognize a functional/operational technical description as a humanly-understandable representation of one or more almost unimaginably complex and time sequenced hardware instantiations. The fact that functional/operational technical descriptions might lend themselves readily to high-level computing languages (or high-level block diagrams for that matter) that share some words, structures, phrases, etc. with natural language simply cannot be taken as an indication that such functional/operational technical descriptions are abstract ideas, or mere expressions of abstract ideas. In fact, as outlined herein, in the technological arts this is simply not true. When viewed through the tools available to those of skill in the art, such functional/operational technical descriptions are seen as specifying hardware configurations of almost unimaginable complexity.

As outlined above, the reason for the use of functional/operational technical descriptions is at least twofold. First, the use of functional/operational technical descriptions allows near-infinitely complex machines and machine operations arising from interchained hardware elements to be described in a manner that the human mind can process (e.g., by mimicking natural language and logical narrative flow). Second, the use of functional/operational technical descriptions assists the person of skill in the art in understanding the described subject matter by providing a description that is more or less independent of any specific vendor's piece(s) of hardware.

The use of functional/operational technical descriptions assists the person of skill in the art in understanding the described subject matter since, as is evident from the above discussion, one could easily, although not quickly, transcribe the technical descriptions set forth in this document as trillions of ones and zeroes, billions of single lines of assembly-level machine code, millions of logic gates, thousands of gate arrays, or any number of intermediate levels of abstractions. However, if any such low-level technical descriptions were to replace the present technical description, a person of skill in the art could encounter undue difficulty in implementing the disclosure, because such a low-level technical description would likely add complexity without a corresponding benefit (e.g., by describing the subject matter utilizing the conventions of one or more vendor-specific pieces of hardware). Thus, the use of functional/operational technical descriptions assists those of skill in the art by separating the technical descriptions from the conventions of any vendor-specific piece of hardware.

In view of the foregoing, the logical operations/functions set forth in the present technical description are representative of static or sequenced specifications of various ordered-matter elements, in order that such specifications may be comprehensible to the human mind and adaptable to create many various hardware configurations. The logical operations/functions disclosed herein should be treated as such, and should not be disparagingly characterized as abstract ideas merely because the specifications they represent are presented in a manner that one of skill in the art can readily understand and apply in a manner independent of a specific vendor's hardware implementation.

SUMMARY

An embodiment provides a method. In one implementation, the method includes but is not limited to indicating a first unmanned aerial device participating in a first task and signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. §101 of hardware, software, and/or firmware configured to effect the herein-referenced method aspects depending upon the design choices of the system designer.

An embodiment provides a system. In one implementation, the system includes but is not limited to circuitry for indicating a first unmanned aerial device participating in a first task and circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to indicating a first unmanned aerial device participating in a first task and signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for indicating a first unmanned aerial device participating in a first task and signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device. In addition to the foregoing, other system aspects are described in the claims, drawings, and text forming a part of the present disclosure.

An embodiment provides a method. In one implementation, the method includes but is not limited to obtaining first data indicating that a first unmanned aerial device delivered a first item to a first entity and transmitting via a free space medium the first data to a provider of the first item as an automatic and conditional response to the first data indicating that the first unmanned aerial device delivered the first item to the first entity, the first data indicating at least one of the first item or the first entity or the first unmanned aerial device. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. §101 of hardware, software, and/or firmware configured to effect the herein-referenced method aspects depending upon the design choices of the system designer.

An embodiment provides a system. In one implementation, the system includes but is not limited to circuitry for obtaining first data indicating that a first unmanned aerial device delivered a first item to a first entity and circuitry for transmitting via a free space medium the first data to a provider of the first item as an automatic and conditional response to the first data indicating that the first unmanned aerial device delivered the first item to the first entity, the first data indicating at least one of the first item or the first entity or the first unmanned aerial device. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining first data indicating that a first unmanned aerial device delivered a first item to a first entity and transmitting via a free space medium the first data to a provider of the first item as an automatic and conditional response to the first data indicating that the first unmanned aerial device delivered the first item to the first entity, the first data indicating at least one of the first item or the first entity or the first unmanned aerial device. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining first data indicating that a first unmanned aerial device delivered a first item to a first entity and transmitting via a free space medium the first data to a provider of the first item as an automatic and conditional response to the first data indicating that the first unmanned aerial device delivered the first item to the first entity, the first data indicating at least one of the first item or the first entity or the first unmanned aerial device. In addition to the foregoing, other system aspects are described in the claims, drawings, and text forming a part of the present disclosure.

An embodiment provides a method. In one implementation, the method includes but is not limited to obtaining first position data from a first entity, by a second entity, the first entity being a first unmanned aerial device and signaling a decision whether or not to allocate a first resource to the second entity after the first position data passes from the first unmanned aerial device to the second entity, the first resource being associated with the first position data. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. §101 of hardware, software, and/or firmware configured to effect the herein-referenced method aspects depending upon the design choices of the system designer.

An embodiment provides a system. In one implementation, the system includes but is not limited to circuitry for obtaining first position data from a first entity, by a second entity, the first entity being a first unmanned aerial device and circuitry for signaling a decision whether or not to allocate a first resource to the second entity after the first position data passes from the first unmanned aerial device to the second entity, the first resource being associated with the first position data. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining first position data from a first entity, by a second entity, the first entity being a first unmanned aerial device and signaling a decision whether or not to allocate a first resource to the second entity after the first position data passes from the first unmanned aerial device to the second entity, the first resource being associated with the first position data. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining first position data from a first entity, by a second entity, the first entity being a first unmanned aerial device and signaling a decision whether or not to allocate a first resource to the second entity after the first position data passes from the first unmanned aerial device to the second entity, the first resource being associated with the first position data. In addition to the foregoing, other system aspects are described in the claims, drawings, and text forming a part of the present disclosure.

An embodiment provides a method. In one implementation, the method includes but is not limited to causing a first unmanned aerial device to guide a first individual to a first destination and causing the first unmanned aerial device to fly to a second destination as an automatic and conditional response to an indication of the first individual arriving at the first destination. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. §101 of hardware, software, and/or firmware configured to effect the herein-referenced method aspects depending upon the design choices of the system designer.

An embodiment provides a system. In one implementation, the system includes but is not limited to circuitry for causing a first unmanned aerial device to guide a first individual to a first destination and circuitry for causing the first unmanned aerial device to fly to a second destination as an automatic and conditional response to an indication of the first individual arriving at the first destination. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to causing a first unmanned aerial device to guide a first individual to a first destination and causing the first unmanned aerial device to fly to a second destination as an automatic and conditional response to an indication of the first individual arriving at the first destination. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for causing a first unmanned aerial device to guide a first individual to a first destination and causing the first unmanned aerial device to fly to a second destination as an automatic and conditional response to an indication of the first individual arriving at the first destination. In addition to the foregoing, other system aspects are described in the claims, drawings, and text forming a part of the present disclosure.

An embodiment provides a method. In one implementation, the method includes but is not limited to obtaining a tracking mode of a delivery task of a first unmanned aerial device and signaling a decision whether or not to omit a record of the first unmanned aerial device completing the delivery task of the first unmanned aerial device as an automatic and conditional response to the tracking mode of the delivery task of the first unmanned aerial device. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. §101 of hardware, software, and/or firmware configured to effect the herein-referenced method aspects depending upon the design choices of the system designer.

An embodiment provides a system. In one implementation, the system includes but is not limited to circuitry for obtaining a tracking mode of a delivery task of a first unmanned aerial device and circuitry for signaling a decision whether or not to omit a record of the first unmanned aerial device completing the delivery task of the first unmanned aerial device as an automatic and conditional response to the tracking mode of the delivery task of the first unmanned aerial device. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining a tracking mode of a delivery task of a first unmanned aerial device and signaling a decision whether or not to omit a record of the first unmanned aerial device completing the delivery task of the first unmanned aerial device as an automatic and conditional response to the tracking mode of the delivery task of the first unmanned aerial device. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining a tracking mode of a delivery task of a first unmanned aerial device and signaling a decision whether or not to omit a record of the first unmanned aerial device completing the delivery task of the first unmanned aerial device as an automatic and conditional response to the tracking mode of the delivery task of the first unmanned aerial device. In addition to the foregoing, other system aspects are described in the claims, drawings, and text forming a part of the present disclosure.

In addition to the foregoing, various other method and/or system and/or program product aspects are set forth and described in the teachings such as text (e.g., claims and/or detailed description) and/or drawings of the present disclosure. The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth below.

BRIEF DESCRIPTION OF THE FIGURES

FIG. 1 depicts an exemplary environment featuring a primary unit operably linked to a network.

FIG. 2 depicts an exemplary environment featuring a user-accessible kiosk having several bays in which unmanned aerial devices (UAD's) may reside.

FIG. 3 depicts an exemplary environment featuring an interface device having at least one processor.

FIG. 8 depicts an exemplary environment featuring UAD's operably coupled with a network.

FIG. 18 depicts a high-level logic flow of an operational process described with reference to FIG. 8.

FIG. 20 depicts an exemplary environment featuring a structural component of a UAD having at least a releasable mechanical linkage to a package or other cargo module.

DETAILED DESCRIPTION

Figure 4:
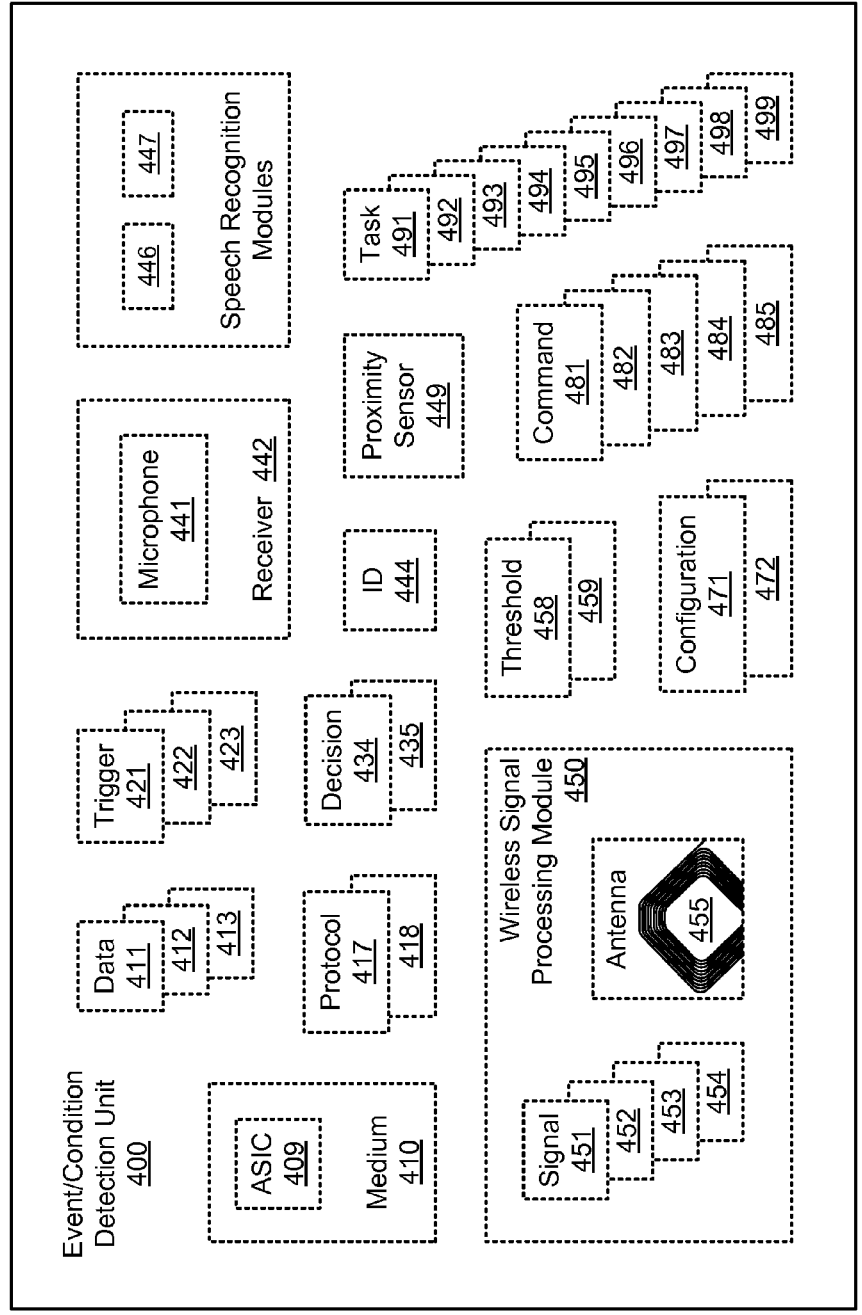
FIG. 4 depicts an exemplary environment featuring an event/condition detection unit.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described below. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will also recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will further recognize that at least a portion of the devices and/or processes described herein can be integrated into an image processing system. A typical image processing system may generally include one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will likewise recognize that at least some of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

FIG. 1 depicts a context in which one or more technologies may be implemented. System 1 comprises a primary unit 110 that may comprise one or more instances of inputs 121; outputs 122; enlistment modules 133, 134; coordinate communication modules 136, 137; data acquisition modules 138, 139; interface control modules 141, 142; entity identification modules 143, 144; name recognition modules 146, 147; tracking control modules 148, 149; flight control modules 151, 152; data delivery modules 153, 154; resource reservation modules 156, 157; or selective retention modules 158, 159 as described in further detail below. In some contexts, primary unit 110 may be operably coupled to one or more networks 190 via one or more communication linkages 140. Instances of storage or other data-handling media 195 operably coupled to one or more such modules may, moreover, reside in primary unit 110 or network 190, as described below. As exemplified herein, a "module" may include special-purpose hardware, general-purpose hardware configured with special-purpose software, or other circuitry configured to perform one or more functions recited below. Also in some contexts such "modules" may be configured to establish or utilize an association (between two devices, e.g.) in response to common interactions (a backup from one device to the other, both logging into a password-access account, or sharing the same printer or router or other peripheral, e.g.). Moreover respective embodiments of primary unit 110 may implement substantially any combination thereof, as exemplified in protocols described below.

FIG. 2 depicts another context in which one or more technologies may be implemented. System 2 comprises a kiosk 250 having several bays 288 each large enough to receive a respective unmanned aerial device (UAD) 201, 202 and accessible to one or more users 226. In some variants kiosk 250 may also include one or more beacons 217 configured to emit an optical or other wireless homing signal 296 recognizable to one or more UAD's 201, 202. The signal 296 is distinctive enough to facilitate UAD's 201, 202 finding beacon 217 several meters or more away from kiosk 250. Moreover each of the bays 288 has protruding or recessed electrical contacts 298 therein to permit each UAD 201, 202 to recharge after it is placed or lands within the bay.

FIG. 3 depicts another system 3 in which one or more technologies may be implemented, one in which one or more instances of a name 351, model 352, or other identifier 355 refer to and identify interface device 310. In a context in which interface device 310 comprises a minivan or other passenger vehicle, for example, such identifier(s) 355 may comprise a plate number 353 of the vehicle. As explained below, interface device 310 may further include one or more instances (implemented in special-purpose circuitry or software executable by one or more processors 365, e.g.) of modes 361, 362, 363; requests 373; invitations 374; reservations 376; confirmations 381, 382; touchscreens or other local interfaces 390 (comprising one or more inputs 391 or outputs 392 physically accessible to or observable by a user at interface device 310, e.g.); acceptances 393, 394; memories 395; or instructions 397.

In light of teachings herein, numerous existing techniques may be applied for configuring special-purpose circuitry or other structures effective for conducting a context-specific structured dialog or other user interaction without undue experimentation or for configuring other decisions and devices as described herein. See, e.g., U.S. Pat. No. 8,024,329 ("Using inverted indexes for contextual personalized information retrieval"); U.S. Pat. No. 7,970,735 ("Cross varying dimension support for analysis services engine"); U.S. Pat. No. 7,920,678 ("Personal virtual assistant"); U.S. Pat. No. 7,870,117 ("Constructing a search query to execute a contextual personalized search of a knowledge base"); U.S. Pat. No. 7,761,480 ("Information access using ontologies"); U.S. Pat. No. 7,743,051 ("Methods, systems, and user interface for e-mail search and retrieval"); U.S. Pat. No. 7,593,982 ("Method, system, and computer program product for saving a search result within a global computer network"); U.S. Pat. No. 7,363,246 ("System and method for enhancing buyer and seller interaction during a group-buying sale"); U.S. Pat. No. 7,177,948 ("Method and apparatus for enhancing online searching sale"); U.S. Pat. No. 6,798,867 ("System and method for the creation and automatic deployment of personalized, dynamic and interactive voice services, with real-time database queries"); U.S. Pub. No. 2011/0081053 ("Methods and systems for occlusion tolerant face recognition"); U.S. Pub. No. 2008/0159622 ("Target object recognition in images and video").

Referring again to FIG. 1, network 190 may serve as a context for introducing one or more processes, systems or other articles described below. In some instances network 190 may include one or more search engines, satellites, servers, processors, routers, or other devices. In some contexts, one or more interface devices owned or operated by user 226 may interact through network 190 (e.g. with one or more other interface devices or networks as described herein). One or more such associated interface devices 310 may be mobile devices, in some contexts, or may function in cooperation (as a network subsystem, e.g.) even when remote from one another. Alternatively or additionally, one or more other interface devices owned or operated by user 226 may likewise interact locally or remotely with or through one another or other interface devices (through network 190, e.g.).

In some contexts, such interface devices (of FIG. 2, e.g.) may include or otherwise communicate with one or more instances of primary unit 110 and may include one or more instances of data outputs or other implementations of machines, articles of manufacture, or compositions of matter that include circuitry or other logic as described below. In some contexts, such implementations may be held or transmitted by conduits, storage devices, memories, other holding devices, or other circuitry for handling data or software (in a satellite, server, or router, e.g.) as described herein. In various embodiments, one or more instances of implementation components or implementation output data may each be expressed within any aspect or combination of software, firmware, or hardware as signals, data, designs, logic, instructions, or other such special-purpose expression or implementation. Interface devices (such as that of FIG. 2, e.g.) may likewise include one or more instances of lenses, transmitters, receivers, integrated circuits, antennas, output devices, reflectors, or input devices for handling data or communicating with local users or via linkage 140, for example.

Those skilled in the art will recognize that some list items may also function as other list items. In the above-listed types of media, for example, some instances of interface devices may include conduits or may also function as storage devices that are also holding devices. One or more transmitters may likewise include input devices or bidirectional user interfaces, in many implementations of interface devices 310. Each such listed term should not be narrowed by any implication from other terms in the same list but should instead be understood in its broadest reasonable interpretation as understood by those skilled in the art.

"Apparent," "automatic," "selective," "conditional," "indicative," "normal," "represented," "related," "partly," "responsive," "distilled," "local," "in a vicinity," "remote," "wireless," "periodic," "free," "aerial," "associated," "primary," "met," "passive," "implemented," "executable," "particular," "specific," "human," "performed," "mobile," "of," "prior," "activated," "future," "light," "contemporaneous," "portable," "toward," or other such descriptors herein are used in their normal yes-or-no sense, not as terms of degree, unless context dictates otherwise. In light of the present disclosure those skilled in the art will understand from context what is meant by "vicinity," by being "in" or "at" a detection region, by "remote," and by other such positional descriptors used herein. "For" is not used to articulate a mere intended purpose in phrases like "circuitry for" or "instruction for," moreover, but is used normally, in descriptively identifying special purpose circuitry or code.

Some descriptions herein refer to a "distillation" of data. Such distillations can include an average, estimate, range, or other computation at least partly distilling a set of data. They can likewise include an indexing, sorting, summarization, distributed sampling, or other process having a purpose or effect of showing some aspect of the data more concisely or effectively than a conventional display or archiving of the entire data. Selecting a last portion of a data set can constitute a distillation, for example, in a context in which the data's utility apparently increases (medians or other cumulative computations, e.g.). Removing duplicative data or indexing available data are useful ways of "distilling" data so that it becomes manageable even while retaining some of its meaning. Those skilled in the art will recognize many useful modes of distilling data in light of the state of the art and of teachings herein.

In some embodiments, "signaling" something can include identifying, contacting, requesting, selecting, or indicating the thing. In some cases a signaled thing is susceptible to fewer than all of these aspects, of course, such as a task definition that cannot be "contacted."

In some embodiments, "status indicative" data can reflect a trend or other time-dependent phenomenon (indicating some aspect of an entity's condition, e.g.). Alternatively or additionally, a status indicative data set can include portions that have no bearing upon such status. Although some types of distillations can require authority or substantial expertise (e.g. making a final decision upon a risky procedure or other course of action), many other types of distillations can readily be implemented without undue experimentation in light of teachings herein.

In some embodiments, one or more applicable "criteria" can include maxima or other comparison values applied to durations, counts, lengths, widths, frequencies, signal magnitudes or phases, digital values, or other aspects of data characterization. In some contexts, such criteria can be applied by determining when or how often a recognizable pattern can be found: a text string, a quantity, a sound, an arrhythmia, a visible dilation, a failure to respond, a non-change, an allergic response, a symptom relating to an apparent condition of the user, or the like.

In some embodiments, "causing" events can include triggering, producing or otherwise directly or indirectly bringing the events to pass. This can include causing the events remotely, concurrently, partially, or otherwise as a "cause in fact," whether or not a more immediate cause also exists.

Some descriptions herein refer to an "indication whether" an event has occurred. An indication is "positive" if it indicates that the event has occurred, irrespective of its numerical sign or lack thereof. Whether positive or negative, such indications may be weak (i.e. slightly probative), definitive, or many levels in between. In some cases the "indication" may include a portion that is indeterminate, such as an irrelevant portion of a useful photograph.

FIG. 4 depicts another system 4 in which one or more technologies may be implemented. Event/condition detection unit 400 comprises special-purpose circuitry implemented as one or more application-specific integrated circuits (ASICs) 409 or other such data-handling media 410. Event/condition detection unit 400 may, in some variants, include one or more instances of data 411, 412, 413; hard-wired or other special-purpose protocols 417, 418; triggers 421, 422, 423; decisions 434, 435; microphones 441 or other receivers 442; identifiers 444; proximity sensors 449; wireless signal processing modules 450 (operable to handle one or more signals 451, 452, 453, 434 transmitted or received via antenna 455, e.g.); thresholds 458, 459; configurations 471, 472; commands 481, 482, 483, 484, 485; or tasks 491, 492, 493, 494, 495, 496, 497, 498, 499 (implemented in special-purpose circuitry or software executable by one or more processors 365, e.g.). In some variants, such commands 481-485 or tasks 491-499 may be received (from user 226, e.g.) via a microphone 441 and a speech recognition module 446, 447 or other such configurations of inputs 391. (In some embodiments, a "module" as described herein may include one or more of special-purpose circuitry or special-purpose device-executable code: code by which a processor 365 that is executing the code, for example, becomes a special-purpose machine.)

Figure 5:
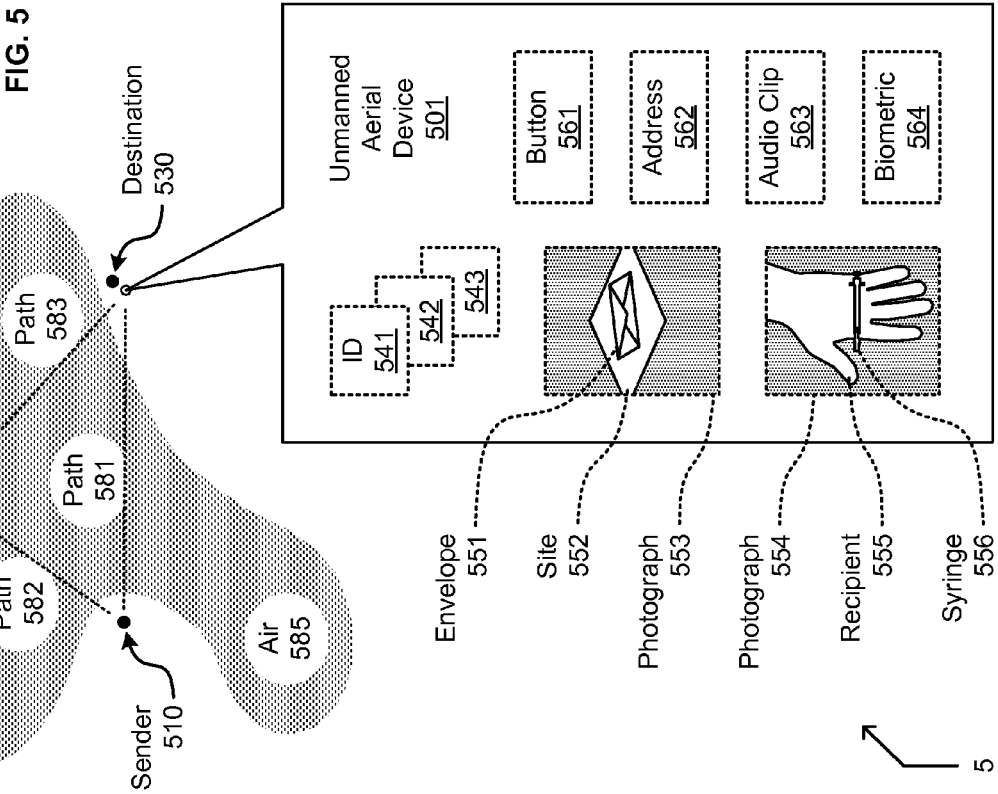
FIG. 5 depicts an exemplary environment featuring a UAD in a vicinity of a destination.

FIG. 5 depicts another system 5 in which one or more technologies may be implemented. An unmanned aerial device (UAD) 501 may travel among a sender 510 (of cargo to be delivered, e.g.), a station 520, and a destination 530 (of the cargo, e.g.) along travel paths 581, 582, 583 through the air 585 as shown. One or more media 195, 410 aboard UAD 501 may contain one or more identifiers 541 of cargo, identifiers 542 of destination 530, or identifiers 543 of the UAD 501 tasked with delivery. Such media may likewise contain other indicia of various planned or completed delivery tasks 491-499, such as a photograph 553 of an item of cargo (envelope 551, e.g.) having been delivered to a delivery site 552 (at destination 530, e.g.); a photograph 554 of a part of a recipient 555 or of an item of cargo (syringe 556, e.g.) being delivered to a destination (recipient 555, e.g.); addresses (of sender 510, station 520, or destination 530, e.g.); audio clips 563 (of recipient 555 refusing or accepting delivery, e.g.); or biometrics 564 (of sender 510 or recipient 555, e.g.). In some implementations, moreover, UAD 501 may implement or interact with one or more instances of interfaces 390 (having one or more buttons 561 thereon as inputs 391, e.g.) as described below.

Figure 15:
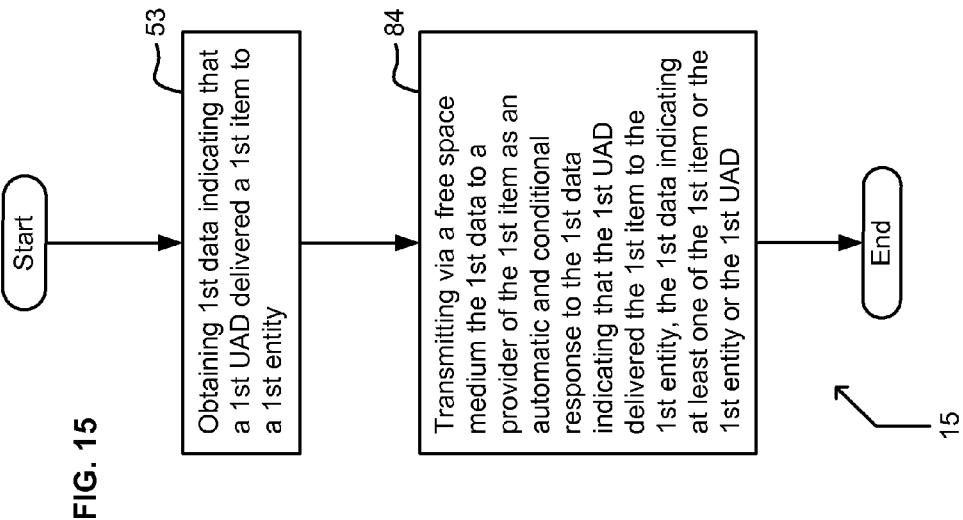
FIG. 15 depicts a high-level logic flow of an operational process described with reference to FIG. 5.

With reference now to FIG. 15, shown is a high-level logic flow 15 of an operational process. Intensive operation 53 describes obtaining first data indicating that a first unmanned aerial device delivered a first item to a first entity (e.g. data acquisition module 138 receiving one or more addresses 562 or photographs 553 as data 411 indicating that one or more UAD's 501 delivered an envelope 551, signature document, or other article to a placement site 552 or other destination 530). This can occur, for example, in a context in which UAD 501 implements or interacts with primary unit 110, UAD 201, and event/condition detection unit 400 as described above. Alternatively or additionally, data 412 may include a biometric 564 (fingerprint, e.g.) or other manifestation of a recipient 555 receiving a medication (in a syringe 556 or capsule, e.g.) or other delivered material as described herein. Either such "first" data 411, 412 may likewise include one or more of an identifier 541 of the "first" item (envelope 551 or syringe 556, e.g.), an identifier 542 of the "first" entity (site 552 or recipient 555, e.g.), an identifier 543 (serial number or alias, e.g.) of the "first" UAD 201, 501 or other such indications signifying a successful delivery.

In light of teachings herein, numerous existing techniques may be applied for configuring special-purpose circuitry or other structures effective for dispatching a vehicle for making deliveries without undue experimentation or for configuring other decisions and devices as described herein. See, e.g., U.S. Pat. No. 8,140,592 ("Delivery operations information system with route adjustment feature and methods of use"); U.S. Pat. No. 8,041,649 ("Methods and systems for postcode-to-postcode delivery interval and routing calculation"); U.S. Pat. No. 7,947,916 ("Mail sorter system and method for moving trays of mail to dispatch in delivery order"); U.S. Pat. No. 7,868,264 ("System and process for reducing number of stops on delivery route by identification of standard class mail"); U.S. Pat. No. 7,739,202 ("Computer system for routing package deliveries"); U.S. Pat. No. 7,647,875 ("Seed hopper and routing structure for varying material delivery to row units"); U.S. Pat. No. 6,801,139 ("Method and system for delivering a time-efficient mobile vehicle route that encompasses multiple limited-duration events").

In light of teachings herein, numerous existing techniques may be applied for configuring special-purpose circuitry or other structures effective for data acquisition (relating to a delivery, e.g.) without undue experimentation or for configuring other decisions and devices as described herein. See, e.g., U.S. Pat. No. 8,111,819 ("Message server and method for notification of a user about the delivery of an electronic message"); U.S. Pat. No. 8,074,642 ("Visual indicator for an aerosol medication delivery apparatus and system"); U.S. Pat. No. 7,984,100 ("Email system automatically notifying sender status and routing information during delivery"); U.S. Pat. No. 7,713,229 ("Drug delivery pen with event notification means"); U.S. Pat. No. 7,559,456 ("Mail delivery indicator system"); U.S. Pat. No. 7,222,081 ("System and method for continuous delivery schedule including automated customer notification"); U.S. Pat. No. 6,902,109 ("Parcel delivery notice"); U.S. Pat. No. 6,859,722 ("Notification systems and methods with notifications based upon prior package delivery"); U.S. Pat. No. 6,535,585 ("System and method for notification upon successful message delivery"); U.S. Pat. No. 6,356,196 ("Verified receipt, notification, and theft deterrence of courier-delivered parcels").

In light of teachings herein, numerous existing techniques may be applied for configuring special-purpose circuitry or other structures effective for detecting and responding automatically to position data, optical data, auditory data, or other indications of a delivery without undue experimentation or for configuring other decisions and devices as described herein. See, e.g., U.S. Pat. No. 8,131,652 ("Residential delivery indicator"); U.S. Pat. No. 7,559,456 ("Mail delivery indicator system"); U.S. Pat. No. 7,483,721 ("Communication device providing diverse audio signals to indicate receipt of a call or message"); U.S. Pat. No. 7,346,662 ("Methods, systems, and products for indicating receipt of electronic mail"); U.S. Pat. No. 7,013,350 ("System setting flags based on address types in destination address field of a message to indicate different transports to deliver the message"); U.S. Pat. No. 7,006,013 ("System and method for visually indicating receipt of a radio communication directed to a uniquely identified vehicle").

In some embodiments described herein, a response (generating a decision, e.g.) to a stimulus is "conditional" if the stimulus can take on either a first possible value or a second possible value (or perhaps others) and in which the content (yes or no, e.g.) or occurrence of the response depends upon which of the possible stimuli are manifested. Likewise a response is "automatic" if it can occur (for at least one possible stimulus set, e.g.) without any human interaction.

Referring again to FIG. 15, extensive operation 84 describes transmitting via a free space medium the first data to a provider of the first item as an automatic and conditional response to the first data indicating that the first unmanned aerial device delivered the first item to the first entity, the first data indicating at least one of the first item or the first entity or the first unmanned aerial device (e.g. data delivery module 153 transmitting a wireless signal 454 (radio frequency, e.g.) containing data 411, 412 indicating a delivery of the first item to the sender 510 of the first item). This can occur, for example, in a context in which data delivery module 153 receives such first data from data acquisition module 138; in which the first item comprises an envelope 551, syringe 556, material, or other such articles physically delivered by one or more UAD's 201, 501 to destination 530; in which such a UAD includes a data delivery module 153 configured to transmit such first data via a wireless signal path 581 (through air 585 or water vapor, e.g.); and in which sender 510 would otherwise be unwilling to entrust the item to be transferred via UAD 501. Alternatively or additionally, such a data delivery module 153 may be configured to transmit such first data indirectly (via a wireless signal path 583 through air 585 and through a station 520 that relays signal 454 to sender 510, e.g.). Alternatively or additionally, station 520 may include (an instance of) a data delivery module 153 configured to perform operation 84 by transmitting some or all such data 411, 412 wirelessly via path 582 as an automatic and conditional response to a suitable trigger 421. In respective embodiments, for example, a primary unit 110 may be configured to perform flow 15 such that trigger 421 comprises any of (1) UAD 501 delivering the first item to destination 530; (2) UAD 501 arriving at station 520 after having delivered the first item to destination 530; or (3) data delivery module 153 receiving an indication that UAD 201 delivered the first item to destination 530.

In light of teachings herein, numerous existing techniques may be applied for configuring special-purpose circuitry or other structures effective for deciding whether or not to route data through a free space medium without undue experimentation or for configuring other decisions and devices as described herein. See, e.g., U.S. Pat. No. 8,175,025 ("Wireless communication apparatus for selecting suitable transfer route on wireless network"); U.S. Pat. No. 8,099,060 ("Wireless/wired mobile communication device with option to automatically block wireless communication when connected for wired communication"); U.S. Pat. No. 8,090,132 ("Wireless communication headset with wired and wireless modes"); U.S. Pat. No. 8,081,967 ("Method to manage medium access for a mixed wireless network"); U.S. Pat. No. 8,040,864 ("Map indicating quality of service for delivery of video data to wireless device"); U.S. Pat. No. 7,899,027 ("Automatic route configuration in hierarchical wireless mesh networks"); U.S. Pat. No. 7,869,444 ("Mixed wireless and cabled data acquisition network"); U.S. Pat. No. 7,865,186 ("Method for operating wired and wireless phone services interconnectively"); U.S. Pat. No. 7,315,548 ("Method and apparatus for determining a route between a source node and a destination node in a wireless multihopping communication network"); U.S. Pat. No. 6,578,085 ("System and method for route optimization in a wireless internet protocol network"); U.S. Pat. No. 6,058,312 ("Automatic selecting apparatus for an optimum wireless communication route").

In light of teachings herein, numerous existing techniques may be applied for configuring special-purpose circuitry or other structures effective for mobile data delivery (deciding when to transmit data from or via a mobile device, e.g.) without undue experimentation or for configuring other decisions and devices as described herein. See, e.g., U.S. Pat. No. 8,200,223 ("Base station and data transfer method for transferring data when a mobile station performs a handover"); U.S. Pat. No. 7,865,212 ("Methods and apparatus for use in transferring user data between two different mobile communication devices using a removable memory card"); U.S. Pat. No. 7,359,346 ("Apparatus for controlling data transmission/reception between main system and remote system of BTS in mobile communication system"); U.S. Pat. No. 7,240,075 ("Interactive generating query related to telestrator data designating at least a portion of the still image frame and data identifying a user is generated from the user designating a selected region on the display screen, transmitting the query to the remote information system"); U.S. Pat. No. 7,107,064 ("Mobile communication device and method for determining whether to transmit position data"); U.S. Pat. No. 6,742,037 ("Method and apparatus for dynamic information transfer from a mobile target to a fixed target that tracks their relative movement and synchronizes data between them"); U.S. Pat. No. 6,694,177 ("Control of data transmission between a remote monitoring unit and a central unit"); U.S. Pat. No. 6,604,038 ("Apparatus, method, and computer program product for establishing a remote data link with a vehicle with minimal data transmission delay"); U.S. Pat. No. 6,591,101 ("Method of subscriber data control in a mobile communication network where subscriber data is transferred from a home mobile switching center to a destination mobile switching center").

Figure 6:
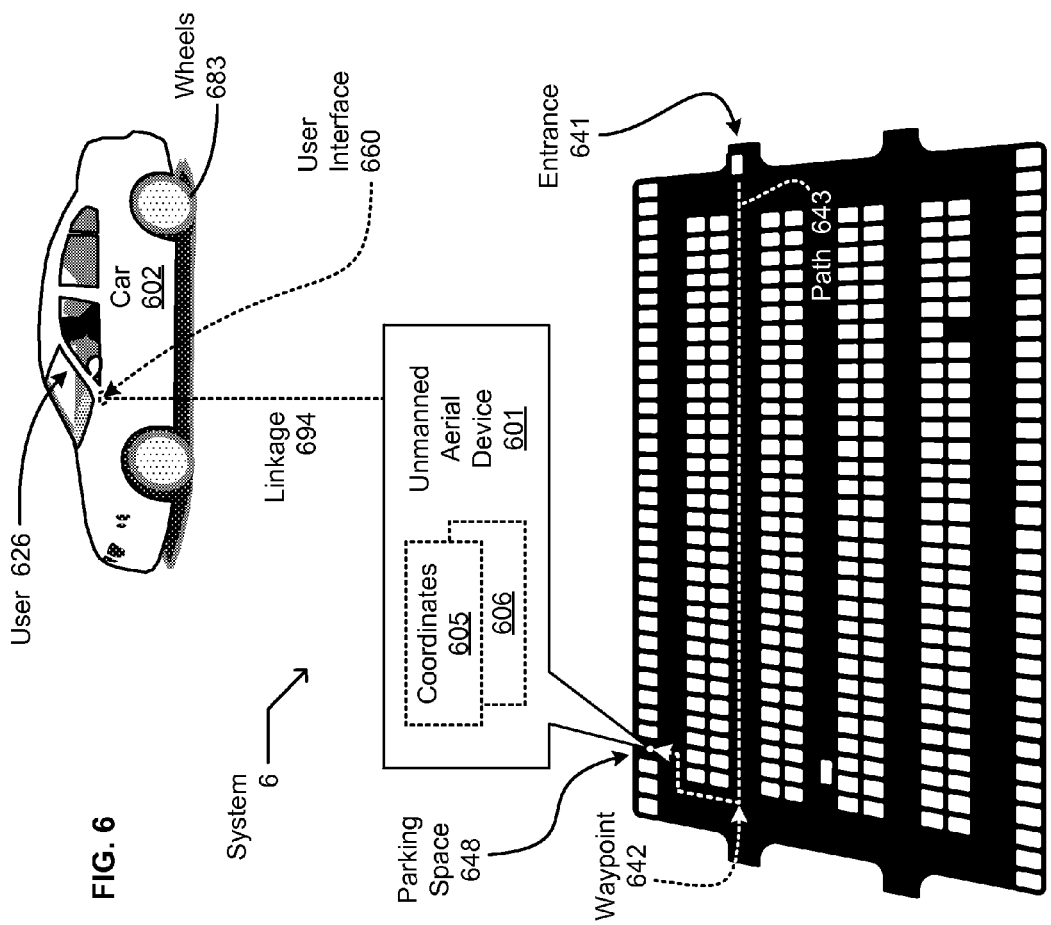
FIG. 6 depicts an exemplary environment featuring a UAD and another entity (a car or driver, e.g.) communicating about a resource (parking space, e.g.).

FIG. 6 depicts another system 6 in which one or more technologies may be implemented, one involving a passenger vehicle (car 602, e.g.) with wheels 683, pontoons, or other such support structures configured to facilitate transportation. As shown, car 602 is configured to bear at least one person (user 626, e.g.) and to include a user interface 660 (navigation system, e.g.). In a context in which such a passenger vehicle approaches an entrance 641 of a parking lot, UAD 601 may be configured (in association with the vehicle or with a zone comprising the parking lot, e.g.) to transmit to the vehicle information of interest. Such information can include coordinates 605, 606 (indicating an open parking space 648 or other location of interest, e.g.) or other positional information (indicating a recommended path 643 or waypoint 642 thereof, e.g.) transmitted via a wireless communication linkage 694.

Figure 16:
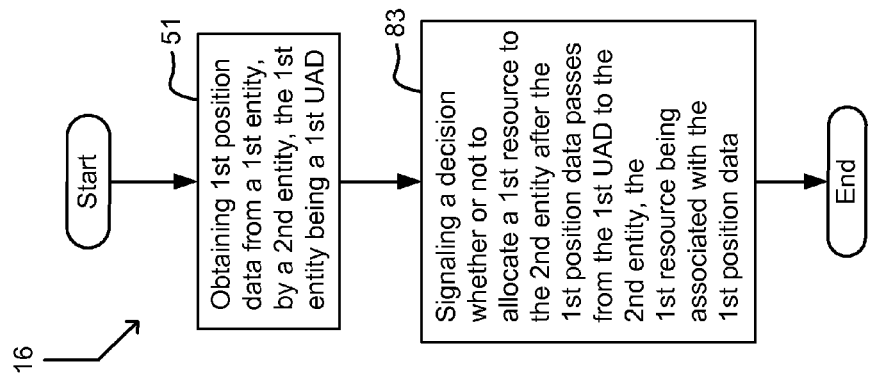
FIG. 16 depicts a high-level logic flow of an operational process described with reference to FIG. 6.

With reference now to FIG. 16, shown is a high-level logic flow 16 of an operational process. Intensive operation 51 describes obtaining first position data from a first entity, by a second entity, the first entity being a first unmanned aerial device (e.g. a coordinate communication module 136 resident in car 602 receiving two or more coordinates 605 from UAD 601 indicating the position of UAD 601). This can occur, for example, in a context in which UAD 601 implements one or more UAD's 201, 501 as described above; in which an instance of primary unit 110 is resident in one or both of the "first" and "second" entities; in which the "second" entity (car 602 or user 626, e.g.) has arrived at an entrance 641 of a crowded parking lot; in which UAD 601 has found and occupied a vacant parking space 648; and in which UAD 601 transmits its location (to a user interface 660 of the "second" entity, e.g.) via a wireless linkage 694 to assist a device or user (in finding and occupying the parking space 648, e.g.). In some contexts, the first UAD 601 may include an interface control module 141 configured to transmit turn-by-turn instructions, coordinates 605, or other such guidance, for example. See FIG. 17. Such guidance can, for example, lead a "second" device (UAD 202 or car 602, e.g.) or user 226, 626 thereof to a pickup or delivery site 552, an article or other material there, a person in a crowd, or other such resources and destinations having locations known to primary unit 110.

In light of teachings herein, numerous existing techniques may be applied for configuring special-purpose circuitry or other structures effective for coordinate communication (acquiring, transmitting, receiving, or using altitude or other positional coordinates, e.g.) without undue experimentation or for configuring other decisions and devices as described herein. See, e.g., U.S. Pat. No. 8,107,608 ("System and method for providing routing, mapping, and relative position information to users of a communication network"); U.S. Pat. No. 8,041,453 ("Method and apparatus for defining and utilizing product location in a vending machine"); U.S. Pat. No. 8,009,058 ("Tracking location and usage of a mechanical sub assembly (MSA) within an automated storage library utilizing a unique identifier associated with location coordinates of the MSA"); U.S. Pat. No. 7,819,315 ("Apparatus and method for providing product location information to customers in a store"); U.S. Pat. No. 7,705,714 ("Wheel position detecting device that performs dedicated local communication for each wheel and tire air pressure detecting device including the same"); U.S. Pat. No. 7,555,386 ("System and method for sharing position information using mobile communication system"); U.S. Pat. No. 6,609,317 ("Signs for display of store item location systems").

In light of teachings herein, numerous existing techniques may be applied for configuring special-purpose circuitry or other structures effective for locating particular individuals or other mobile targets without undue experimentation or for configuring other decisions and devices as described herein. See, e.g., U.S. Pat. No. 8,200,247 ("Confirming a venue of user location"); U.S. Pat. No. 8,106,746 ("Method, apparatus, and system for selecting and locating objects having radio frequency identification (RFID) tags"); U.S. Pat. No. 8,064,647 ("System for iris detection tracking and recognition at a distance"); U.S. Pat. No. 8,032,153 ("Multiple location estimators for wireless location"); U.S. Pat. No. 7,925,093 ("Image recognition apparatus"); U.S. Pat. No. 7,893,848 ("Apparatus and method for locating, identifying and tracking vehicles in a parking area"); U.S. Pat. No. 7,876,215 ("System and method for locating and notifying a mobile user of people having attributes or interests matching a stated preference"); U.S. Pat. No. 7,656,292 ("Flexible anti-theft pack for tracking and location"); U.S. Pat. No. 7,647,171 ("Learning, storing, analyzing, and reasoning about the loss of location-identifying signals"); U.S. Pat. No. 7,092,566 ("Object recognition system and process for identifying people and objects in an image of a scene"); U.S. Pat. No. 6,513,015 ("System and method for customer recognition using wireless identification and visual data transmission"); U.S. Pat. No. 6,219,639 ("Method and apparatus for recognizing identity of individuals employing synchronized biometrics").

In light of teachings herein, numerous existing techniques may be applied for configuring special-purpose circuitry or other structures effective for locating specific resources without undue experimentation or for configuring other decisions and devices as described herein. See, e.g., U.S. Pat. No. 8,194,975 ("Use of an intrinsic image in face recognition"); U.S. Pat. No. 7,659,835 ("Method and apparatus for recognizing parking slot by using bird's eye view and parking assist system using the same"); U.S. Pat. No. 7,480,394 ("Method and arrangement for recognizing objects in mail item images, their position and reading their postal information"); U.S. Pat. No. 6,592,033 ("Item recognition method and apparatus"); U.S. Pat. No. 6,373,982 ("Process and equipment for recognition of a pattern on an item presented"); U.S. Pat. No. 6,313,745 ("System and method for fitting room merchandise item recognition using wireless tag"); U.S. Pat. No. 6,121,916 ("Method and apparatus for recognizing stationary objects with a moving side-looking radar").

Referring again to FIG. 16, extensive operation 83 describes signaling a decision whether or not to allocate a first resource to the second entity after the first position data passes from the first unmanned aerial device to the second entity, the first resource being associated with the first position data (e.g. resource reservation module 156 confirming a reservation 376 of parking space 648 after coordinates 605 thereof arrive at user interface 660). This can occur, for example, in a context in which parking space 648 is the "first" resource; in which the "second" entity is identified as the driver (by name 351, e.g.) or as the car (by model 352 or license plate number 353, e.g.); in which UAD 601 and user interface 660 each contain an instance of primary unit 110; in which UAD 601 receives and announces one or more such identifiers (via a speaker, projector, or other output 122 of UAD 601, e.g.) to passersby; in which user 626 enters the decision by indicating whether or not to associate the "first" resource with an identifier 355 of the second entity via input 121 of user interface 660; and in which user 626 would otherwise be unable to reserve the resource before happening across it. In other applications of flow 16, such "first" resources may include a cashier or other living entity; a public table or other space; a power or network connection; an item for sale or other object; or other such resources that a device can deem available for allocation under conditions as described herein. Moreover such "second" entities may include UAD's or other devices or people as described herein (identified by entity identification module 143, e.g.).

In light of teachings herein, numerous existing techniques may be applied for configuring special-purpose circuitry or other structures effective for entity identification (associating a specific identifier with a device, user, group, or other entity, e.g.) without undue experimentation or for configuring other decisions and devices as described herein. See, e.g., U.S. Pat. No. 8,176,156 ("Server identification assignment in a distributed switched storage environment"); U.S. Pat. No. 8,136,025 ("Assigning document identification tags"); U.S. Pat. No. 7,970,426 ("Method of assigning provisional identification to a subscriber unit and group"); U.S. Pat. No. 7,877,515 ("Identity assignment for software components"); U.S. Pat. No. 7,495,576 ("Modular electronic sign and method of assigning a unique identifier to common modules of said sign"); U.S. Pat. No. 7,383,174 ("Method for generating and assigning identifying tags to sound files"); U.S. Pat. No. 6,721,761 ("System for assigning digital identifiers to telephone numbers and IP numbers"); U.S. Pat. No. 6,430,182 ("Fabric system and method for assigning identifier for fabric apparatus therefor"); U.S. Pat. No. 6,283,227 ("Downhole activation system that assigns and retrieves identifiers"); U.S. Pat. No. 6,114,970 ("Method of assigning a device identification"); U.S. Pat. No. 6,091,738 ("Transmission-equipment and method for assigning transmission-equipment identification number in transmission system").

In light of teachings herein, numerous existing techniques may be applied for configuring special-purpose circuitry or other structures effective for resource reservation (associating an entity identifier with a living or other resource, e.g.) without undue experimentation or for configuring other decisions and devices as described herein. See, e.g., U.S. Pat. No. 8,166,484 ("System for confirming and cancelling tentative resource reservation within the valid time indicates period during which the tentative reservation request is valid"); U.S. Pat. No. 8,160,906 ("System and method for improved rental vehicle reservation management"); U.S. Pat. No. 8,150,403 ("Reservation of mobile station communication resources"); U.S. Pat. No. 8,117,051 ("Method for determining the number of available transport seats in a computerized reservation system"); U.S. Pat. No. 8,065,287 ("Method and system for searching availability of an entity for purchase or reservation"); U.S. Pat. No. 7,956,769 ("Method and system for reservation-based parking"); U.S. Pat. No. 7,818,190 ("Camping reservation system, method and program"); U.S. Pat. No. 7,783,530 ("Parking reservation systems and related methods"); U.S. Pat. No. 7,783,506 ("System and method for managing reservation requests for one or more inventory items"); U.S. Pat. No. 7,693,779 ("Method and system for requesting a reservation for a set of equity instruments to be offered"); U.S. Pat. No. 7,634,426 ("Golf reservation system"); U.S. Pat. No. 7,548,866 ("Individual seat selection ticketing and reservation system").

Figure 7:
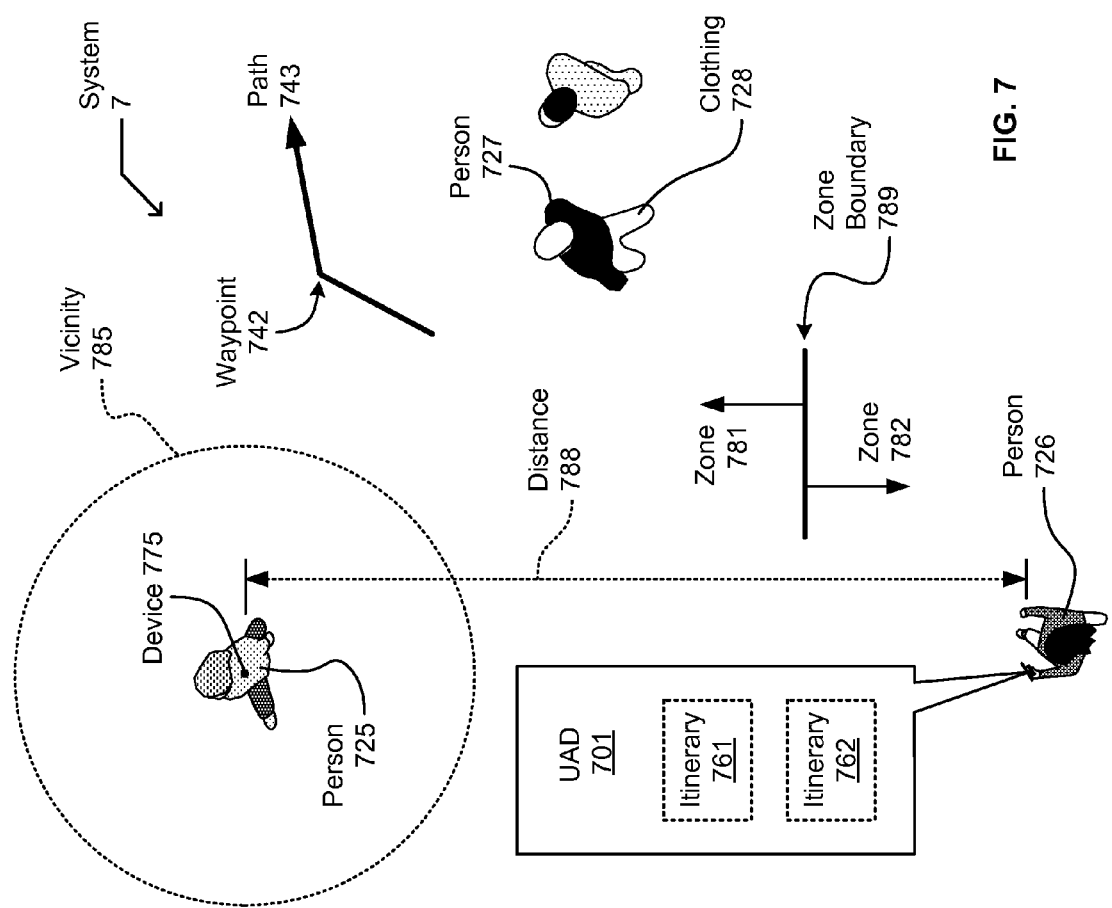
FIG. 7 depicts an exemplary environment featuring three pedestrians in one zone, one pedestrian in another zone, and at least one handheld UAD.

FIG. 7 depicts another system 7 in which one or more technologies may be implemented, depicting a view from above of several people 725, 726, 727 near a zone boundary 789 dividing two zones 781, 782 (areas of land, e.g.). Person 726 is shown carrying an unmanned aerial device 701 containing itineraries 761, 762 (in a memory 395 or other medium 195 thereof, e.g.) in one or more contexts further described below. In one context, person 726 is walking, and UAD 701 is traveling, toward a person 725 or device 775 that is currently a distance 788 away. In another, the destination 530 is defined as a vicinity 785 (a detection range of a proximity sensor 449, e.g.) of such a device 775. In another context, UAD 701 is guiding person 726 generally along a static or dynamic path 743 comprising a waypoint 742. In yet another context, a subject (person 727, e.g.) has one or more attributes (clothing 728 or voice or face or other biometric 564, e.g.) susceptible of automatic recognition by one or more stationary event/condition detection units 400 or other recognition modules (aboard a UAD 701 or other portable device 775, e.g.). See FIG. 14.

Figure 17:
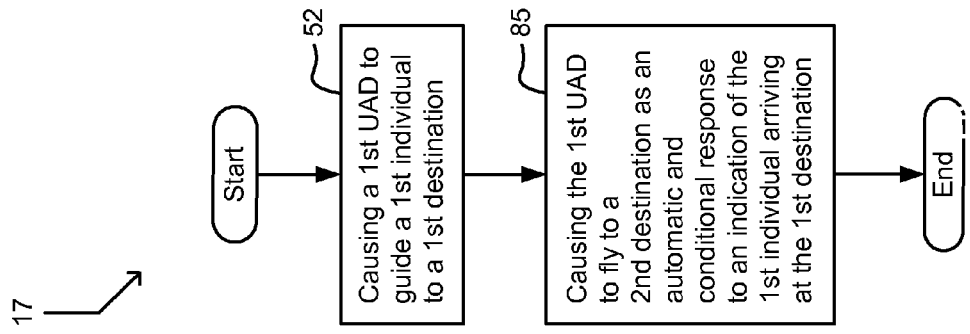
FIG. 17 depicts a high-level logic flow of an operational process described with reference to FIG. 7.

With reference now to FIG. 17, shown is a high-level logic flow 17 of an operational process. Intensive operation 52 describes causing a first unmanned aerial device to guide a first individual to a first destination (e.g. interface control module 141 causing a display, speaker, or other output 392 of unmanned aerial device 701 to provide navigational instruction 397 effective for guiding person 726 according to a first itinerary 761). This can occur, for example, in a context in which the first destination is a vicinity 785 of a person 725 or of a portable device 775; in which the first destination is also a non-stationary component of the first itinerary 761 (indicating such a person 725, device 775, or other destination, e.g.); in which person 726 is the "first" individual, who may be traveling through a zone 782 in which conventional GPS navigation devices cannot be used; and in which person 726 would otherwise have to find the "first" destination without any device assistance. On a cruise ship or tightly managed facility in which an owner (of zone 782, e.g.) does not provide a public wireless connectivity (cell tower access, e.g.) or in which individuals are not permitted to bring their own wireless devices onsite, for example, the owner may lend such UAD's 701 to visitors for authorized uses (finding a stationary or other destination 530 within or across a controlled zone 782, e.g.). Alternatively, in some variants, a flight control module 151 may perform operation 52 by flying ahead of the first individual (user 626, e.g.) slow enough to be followed. This can occur, for example, in a context in which itinerary 761 defines the first destination (parking space 648, e.g.) and in which flight control module 151 is configured to respond to a microphone, accelerometer, camera, or other input 391 of a "first" UAD signaling such flying guidance. For example, flight control module 151 may be configured to cause the first UAD to maintain a suitable lead distance (on the order of 1-3 meters, e.g.) of the first individual in some contexts, landing or otherwise slowing down as necessary if the individual follows slowly, moving laterally or backward if the individual moves orthogonally to or opposite to the first UAD's current or next direction of travel, giving up (and returning to a kiosk 250 or other "home" station, e.g.) if the individual stops following for a period of time exceeding a threshold (on the order of 1 or 60 seconds, e.g.).

Alternatively or additionally, an instance of flight control module 151 aboard UAD 701 may be configured (by including a microphone 441 operatively coupled to a speech recognition module 446, e.g.) to recognize and conditionally follow one or more commands given by the first person ("stay with me" or "fly away" e.g.). In some variants, for example, such a command 482 of "stay with me" can conditionally cause an override or modification of a default configuration of flight control module 151 so that flight control module 152 is temporarily disabled or so that itinerary 762 is suspended until after speech recognition module 446 detects and signals the "fly away" command 483 (to one or more flight control modules 151, 152, e.g.). This can occur, for example, in a context in which the latter event defines an alternative trigger 422 causing the first UAD to fly to a "home" station (or a "second" destination, e.g.) defined by itinerary 762 under the control of flight control module 152.

In light of teachings herein, numerous existing techniques may be applied for configuring special-purpose circuitry or other structures effective for interface control (remotely or locally controlling how an interface handles user input or output, e.g.) without undue experimentation or for configuring other decisions and devices as described herein. See, e.g., U.S. Pat. No. 8,201,143 ("Dynamic mating of a modified user interface with pre-modified user interface code library"); U.S. Pat. No. 8,198,568 ("Input sensitive user interface"); U.S. Pat. No. 8,185,483 ("System for design and use of decision models"); U.S. Pat. No. 8,184,070 ("Method and system for selecting a user interface for a wearable computing device"); U.S. Pat. No. 8,181,119 ("User interface with inline customization"); U.S. Pat. No. 8,171,460 ("System and method for user interface automation"); U.S. Pat. No. 8,171,394 ("Methods and systems for providing a customized user interface for viewing and editing meta-data"); U.S. Pat. No. 8,165,567 ("Method and system for customizing user interface by editing multimedia content"); U.S. Pat. No. 8,151,201 ("User interface manager and method for reacting to a change in system status"); U.S. Pat. No. 8,127,233 ("Remote user interface updates using difference and motion encoding"); U.S. Pat. No. 8,122,365 ("System and method for dynamic creation and customization of a user interface in a web service environment"); U.S. Pat. No. 7,908,221 ("System providing methods for dynamic customization and personalization of user interface").

Referring again to FIG. 17, extensive operation 85 describes causing the first unmanned aerial device to fly to a second destination as an automatic and conditional response to an indication of the first individual arriving at the first destination (e.g. flight control module 152 causing a "first" UAD 701 to fly to a kiosk 250 or other station 520 as an implementation of an itinerary 762 triggered by the first UAD arriving at the first destination). This can occur, for example, in a context in which the first UAD implements one or more primary units 110 or interface devices 310; in which the "second" destination comprises the kiosk 250 or other station 520; in which a proximity sensor 449 or other such input 121 (operatively coupled to a flight control module 152 of device 775, e.g.) detects that UAD 701 is in a vicinity 785 of device 775 (as the indication of the first individual arriving at the first destination, e.g.); and in which person 726 would otherwise have to instruct UAD 701 what to do after arriving. In some variants, for example, such an input 121 may include a wireless signal processing module 450 configured to transmit a first wireless signal 451 and receive a second wireless signal 452 (echo, e.g.) responsive thereto, the wireless signals 451, 452 jointly manifesting a delay indicative of a distance 788 between the devices so that a signal 453 derived therefrom indicates the first UAD arriving "at" the first destination as the derived signal 453 crossing a threshold 458, the flight control module 152 being operatively coupled to wireless signal processing module 450 and responsive to such crossing. Alternatively or additionally, network 190 may include an event/condition detection unit 400 implemented in UAD 701. In some variants, moreover, one or more additional flight control modules 152 may be configured to perform one or more variants of operation 85 (causing the 1st UAD to fly to a 3nd destination as an automatic and conditional response to an indication of the first individual arriving at the 2nd destination or to some other indication of the first UAD arriving at the 2nd destination, e.g.).

In light of teachings herein, numerous existing techniques may be applied for configuring special-purpose circuitry or other structures effective for flight control (using one or more remote or on-board controllers to cause an aerial device to implement a user-specified or autonomously selected route or itinerary, e.g.) without undue experimentation or for configuring other decisions and devices as described herein. See, e.g., U.S. Pat. No. 8,186,589 ("UAV decision and control system"); U.S. Pat. No. 8,100,366 ("Automatic kite flight control system"); U.S. Pat. No. 8,074,941 ("Aircraft flight control"); U.S. Pat. No. 7,962,252 ("Self-contained avionics sensing and flight control system for small unmanned aerial vehicle"); U.S. Pat. No. 7,502,684 ("Method and system for the automatic piloting of an aircraft on the approach to an airdrop position"); U.S. Pat. No. 7,431,243 ("Guidance and control for an autonomous soaring UAV"); U.S. Pat. No. 7,130,741 ("Navigating a UAV with a remote control device"); U.S. Pat. No. 6,926,233 ("Automatic formation flight control system (AFFCS)—a system for automatic formation flight control of vehicles not limited to aircraft, helicopters, or space platforms"); U.S. Pat. No. 6,856,894 ("Navigating a UAV under remote control and manual control with three dimensional flight depiction"); U.S. Pat. No. 6,847,856 ("Method for determining juxtaposition of physical components with use of RFID tags"); U.S. Pat. No. 6,497,600 ("Automatic pilot system for model aircraft").

Another system 8 in which one or more technologies may be implemented is shown in FIG. 8, depicting a view of several unmanned aerial devices (UAD's) 801, 802, 803 configured to communicate with a control unit 860 on a network 890. Task definition module 870 (residing in control unit 860, e.g.) may include one or more aliases 871 in a role list 875 (identifying one or more unmet needs of a task 491-499, e.g.) and one or more aliases ("Hulk," e.g.) in a participant list 885 or other met needs list 880 of the task or job. UAD 801 comprises a name recognition module 810 configured to recognized a primary identifier 811 of UAD 801. UAD 802 comprises a name recognition module 820 configured to recognized a primary identifier 821 of UAD 802 as well as one or more aliases 822, 823 of UAD 802. (In some embodiments, one or more aliases or other identifiers "of" a device may also refer to a specific circuit or virtual entity at least partly aboard the device.)

With reference now to FIG. 18, shown is a high-level logic flow 18 of an operational process. Intensive operation 54 describes indicating a first unmanned aerial device participating in a first task (e.g. enlistment module 133 generating a confirmation 381 that UAD 801 will participate in a delivery task 491 being coordinated by control unit 860). This can occur, for example, in a context in which one or more networks 190, 890 comprise interface device 310; in which control unit 860 and UAD's 801, 802, 803 may each contain (a respective instance of) primary unit 110, each optionally including event/condition detection unit 400; in which (an instance of) enlistment module 133 resides in control unit 840 and transmits an invitation 374 to UAD 801 to participate in one or more tasks 491-499; and in which UAD 801 transmits a timely acceptance 393 of the invitation 374. Alternatively or additionally, one or more enlistment modules 134 (resident in UAD 801, e.g.) may be configured to identify tasks 491, 492 suitable for UAD 801 to participate in and may transmit one or more requests 373 for such participation (to control unit 860, e.g.). This can occur, for example, in which enlistment module 133 is configured to perform an instance of operation 54 by transmitting an acceptance 394 of request 373. In some contexts, such requests 373 and invitations 374 (in an instance of network 190 that includes several UAD's 801, 802, 803 as described above, e.g.) may include a temporal threshold 459 expressing a deadline at or before which the request or invitation recipient must respond (as an expiration time of the request or invitation after which no acceptance of such request 373 or invitation 374 would be valid, e.g.). Alternatively or additionally, in the absence of such expression, one or more enlistment modules 133, 134 may be configured to apply a default deadline (within 1-2 orders of magnitude of a millisecond or a second after such transmission, e.g.), after which such recruitment subtask may be deemed unsuccessful.

In light of teachings herein, numerous existing techniques may be applied for configuring special-purpose circuitry or other structures effective for device enlistment (enabling or otherwise causing one or more available devices to participate in one or more suitable tasks, e.g.) without undue experimentation or for configuring other decisions and devices as described herein. See, e.g., U.S. Pat. No. 8,151,272 ("Optimized usage of collector resources for performance data collection through even task assignment"); U.S. Pat. No. 8,128,484 ("Game system generating second game according to game result of a device and allowing other devices to participate in second game thus generated"); U.S. Pat. No. 8,051,764 ("Fluid control system having selective recruitable actuators"); U.S. Pat. No. 7,948,447 ("Mobile display"); U.S. Pat. No. 7,864,702 ("Control and recruitment of client peripherals from server-side software"); U.S. Pat. No. 7,406,515 ("System and method for automated and customizable agent availability and task assignment management"); U.S. Pat. No. 7,308,472 ("System allowing data input device to request management server to assign a data input job to itself"); U.S. Pat. No. 6,975,820 ("Device control using job ticket scoring"); U.S. Pat. No. 6,493,581 ("System and method for rapid recruitment of widely distributed easily operated automatic external defibrillators").

Referring again to FIG. 18, extensive operation 82 describes signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device (e.g. control unit 860 transmitting a command 481 that configures name recognition module 810 to respond to an alias 871 of "Aunt" as an automatic and conditional response to control unit 860 receiving an acceptance or confirmation 381 indicating that UAD 801 will participate in delivery task 491). This can occur, for example, in a context in which "Aunt" is not a primary identifier 811 (serial number or Internet Protocol address, e.g.) that UAD 801 ordinarily responds to and in which name recognition module 810 was previously configured not to respond to "Aunt"; in which a name recognition module 820 of UAD 802 responds to an alias 822 of "Hulk" pursuant to the same delivery task 491; in which a primary identifier 821 of UAD 802 is neither "Hulk" nor "Aunt"; in which enlistment module 133 also causes alias 871 to be transferred into a participant list 885 of the delivery task 491 (in a met needs list 880 thereof, e.g.) that grows with each successful recruitment; and in which the primary digital identifier would otherwise have to be used throughout the task in addressing UAD 801. Alternatively or additionally, a primary unit 110 (residing in station 520, e.g.) remotely controlling UAD 801 may include a name recognition module 146 configured to perform operation 84 (pursuant to a successful recruitment as described above, e.g.).

In light of teachings herein, numerous existing techniques may be applied for configuring special-purpose circuitry or other structures effective for name recognition (determining whether an incoming signal is addressing an entity by comparing a component of the incoming signal against one or more names of the entity, e.g.) without undue experimentation or for configuring other decisions and devices as described herein. See, e.g., U.S. Pat. No. 8,135,764 ("Configuration management server, name recognition method and name recognition program"); U.S. Pat. No. 7,865,356 ("Method and apparatus for providing proper or partial proper name recognition"); U.S. Pat. No. 7,822,988 ("Method and system for identity recognition"); U.S. Pat. No. 7,792,837 ("Entity name recognition"); U.S. Pat. No. 7,370,078 ("Determining a remote device name"); U.S. Pat. No. 6,052,682 ("Method of and apparatus for recognizing and labeling instances of name classes in textual environments").

Figure 9:
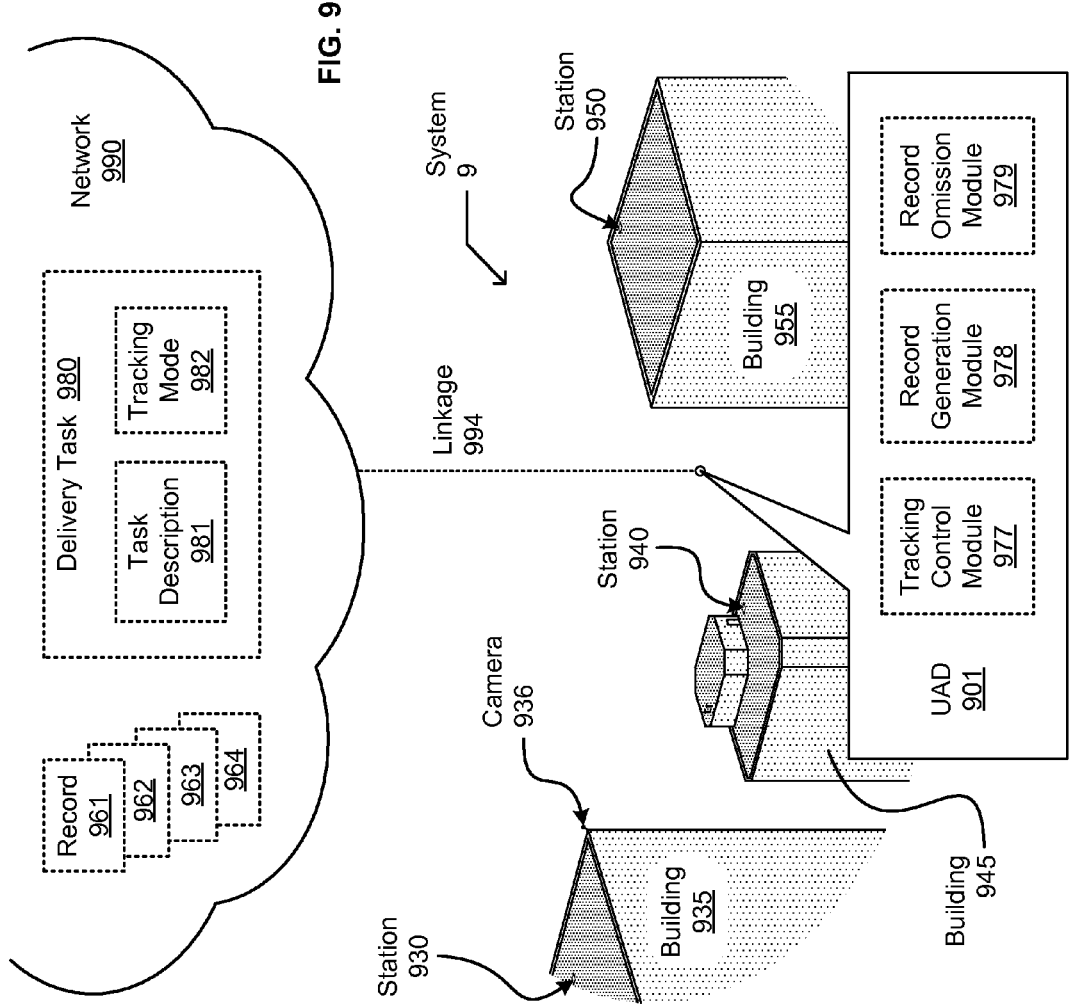
FIG. 9 depicts an exemplary environment featuring a UAD traveling among several stations.

Another system 9 in which one or more technologies may be implemented is shown in FIG. 9, depicting UAD 901 (comprising primary unit 110, e.g.) operably connected with one or more networks 190 (comprising network 990, e.g.) via a wireless communication linkage 994. Network 990 includes (a memory 395 or other data handling medium 195 containing) one or more records 961, 962, 963, 964, some of which may (optionally) include digitally represented delivery tasks 980 or other tasks 491-499, each of which may (optionally) comprise one or more instances of task descriptions 981 or tracking modes 982 as shown. UAD 901 may (optionally) include one or more instances of tracking control modules 977; record generation modules 978, or record omission modules 979. In some contexts, UAD 901 (implementing UAD 501, e.g.) may be configured to fly (along respective paths 581, 582, 583, e.g.) among two or more stations 930, 940, 950 (e.g. on respective buildings 935, 945, 955), some or all of which may be observable by a stationary or pivotable camera 936 (in a configuration like systems 3-8 described above, e.g.).

Figure 19:
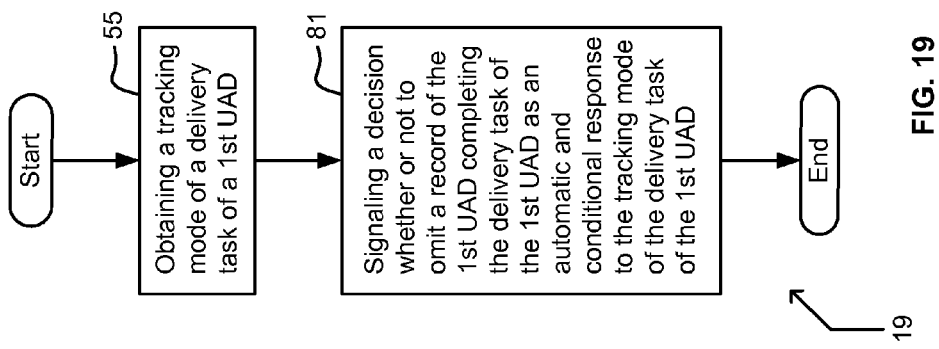
FIG. 19 depicts a high-level logic flow of an operational process described with reference to FIG. 9.

With reference now to FIG. 19, shown is a high-level logic flow 19 of an operational process. Intensive operation 55 describes obtaining a tracking mode of a delivery task of a first unmanned aerial device (e.g. tracking control module 977 receiving a tracking mode 982 of zero pertaining to a delivery task 980 that has been assigned to UAD 901). This can occur, for example, in a context in which a task description 981 of delivery task 980 indicates a physical delivery of a "first" item (envelope 551, e.g.) to station 940; in which UAD 901 implements a primary unit 110 that includes data acquisition module 138; in which one or more just-completed task 493 involved UAD 901 visiting station 950; in which a tracking mode 982 of zero corresponds to a delivery protocol 417 by which the specific item is delivered in lieu of operation 53 (without notifying a provider of an item delivered, e.g.); and in which tracking control module 977 would otherwise trigger data acquisition module 138 to obtain at least some delivery-indicative data 411-413 in response to the item being delivered to station 940 (by performing operation 53, e.g.). See FIG. 15. In some variants, for example, task 493 may include one or more instances of delivery tasks 494, pickup tasks 495, recharge tasks 496, reconfiguration tasks 497, or data transfer tasks 498. In some variants, for example, UAD 901 downloads each successive task in a resting state after completing the prior task. Alternatively or additionally, tracking control module 977 may be configured to implement a default tracking mode 361—indicating at least one of the first item(s) or UAD(s), e.g.—for each task 494-499 except when that task specifies an alternative tracking mode (such as a brief mode 362 or user-defined mode 363, e.g.).

In some variants, one or more instances of tracking control module 148 resident in network 990 may be configured to perform operation 55. This can occur, for example, in a context in which the first UAD 901 does not have any on-board capability of performing operation 55 or is currently configured not to perform operation 55; in which network 990 contains one or more instances of primary unit 110 (resident in a "second" UAD 202 or tower-based station 520, e.g.); and in which tracking control module 148 receives tracking mode 982 as a component of a delivery task 980 assigned to the first UAD 901.

In light of teachings herein, numerous existing techniques may be applied for configuring special-purpose circuitry or other structures effective for tracking control (identifying and updating how increments of task progress are documented, e.g.) without undue experimentation or for configuring other decisions and devices as described herein. See, e.g., U.S. Pat. No. 8,179,261 ("Identification and surveillance device, system and method for individual item level tracking"); U.S. Pat. No. 8,179,253 ("Location and tracking system, method and device using wireless technology"); U.S. Pat. No. 8,135,171 ("Multipoint tracking method and related device"); U.S. Pat. No. 8,115,625 ("Parental alert and child tracking device which determines if a child has deviated from a predicated travel route"); U.S. Pat. No. 8,014,917 ("Apparatus for tracking and recording vital signs and task-related information of a vehicle to identify operating patterns"); U.S. Pat. No. 7,978,065 ("Device, system and method for tracking mobile assets"); U.S. Pat. No. 7,951,046 ("Device, method and computer program product for tracking and monitoring an exercise regimen"); U.S. Pat. No. 7,451,445 ("Mechanism for tracking the execution progress of a parent task which spawns one or more concurrently executing child tasks"); U.S. Pat. No. 7,401,030 ("Method and system for tracking disposition status of an item to be delivered within an organization"); U.S. Pat. No. 6,604,124 ("Systems and methods for automatically managing work flow based on tracking job step completion status"); U.S. Pat. No. 6,463,420 ("Online tracking of delivery status information over a computer network").

Referring again to FIG. 19, extensive operation 81 describes signaling a decision whether or not to omit a record of the first unmanned aerial device completing the delivery task of the first unmanned aerial device as an automatic and conditional response to the tracking mode of the delivery task of the first unmanned aerial device (e.g. selective retention module 158 implementing either a decision 434 to deactivate record generation module 978 temporarily or a decision 435 to cause record generation module 978 to generate a record 961 of "first" UAD 901 having made such a delivery by configuring record generation module 978 before UAD 901 approaches building 945). This can occur, for example, in a context in which decision 435 is "implemented" by a selective retention module 158 (resident in network 990, e.g.) transmitting (to record generation module 978, e.g.) either (1) a Boolean expression ("yes," e.g.) indicating that a user has requested one or more records 961-963 of the delivery or (2) an identifier 444 of which tracking mode 361-363 to use in such acquisition. Alternatively or additionally, decision 435 may be implemented by causing record generation module 978 to be transmitted to or updated aboard UAD 901. Likewise a decision 434 "to omit a record" may be "implemented" by selective retention module 158 causing a selective deletion of record 961 (of UAD 901 delivering the "first" item to station 940, e.g.) before one or more similar records 962-964 (relating to other tasks, e.g.) are transmitted from UAD 901 to network 990 (in a batch transfer, e.g.). This can occur, for example, in a context in which a data acquisition module 139 residing in UAD 901 generates and holds at least one photograph 553, 554 or other record 961-963 for each delivery aboard UAD 901 (in a memory 395 or other data-handling medium 195 thereof, e.g.); in which record omission module 979 selectively deletes a subset of such records 961-963 identified by selective retention module 158; and in which a remainder (comprising record 962, e.g.) of such records is later transmitted to network 990. In other contexts a selective retention module 158 resident in network 990 can implement a decision to omit such a record 961 of the delivery task completion (from a data transmission to a station 520 outside network 990, e.g.) by explicitly listing (a) one or more records 962-963 to be included in such transmission or (b) one or more records 961 to be excluded from such transmission. This can occur, for example, in a context in which UAD 901 implements primary unit 110 and one or more of the above-described UAD's and in which either (1) unwanted tracking of delivery task 980 would occur or (2) UAD 901 would be unable to track a completion of other potentially available tasks 491-499.

In light of teachings herein, numerous existing techniques may be applied for configuring special-purpose circuitry or other structures effective for selective event tracking without undue experimentation or for configuring other decisions and devices as described herein. See, e.g., U.S. Pat. No. 8,219,572 ("System and method for searching enterprise application data"); U.S. Pat. No. 8,165,932 ("Enhancement of network accounting records"); U.S. Pat. No. 8,019,771 ("Method for dynamically finding relations between database tables"); U.S. Pat. No. 7,922,088 ("System and method to automatically discriminate between different data types"); U.S. Pat. No. 7,903,839 ("Method for canceling impact of physical property variability on image quality performance of digital imaging system"); U.S. Pat. No. 7,883,013 ("Mobile image capture and processing system"); U.S. Pat. No. 7,870,012 ("Method for managing a workflow process that assists users in procurement, sourcing, and decision-support for strategic sourcing"); U.S. Pat. No. 7,835,971 ("Method and system configured for facilitating management of international trade receivables transactions"); U.S. Pat. No. 7,792,808 ("More efficient search algorithm (MESA) using virtual search parameters"); U.S. Pat. No. 7,769,644 ("Bill of lading transmission and processing system for less than a load carriers"); U.S. Pat. No. 7,739,096 ("System for extraction of representative data for training of adaptive process monitoring equipment"); U.S. Pat. No. 7,733,223 ("Effectively documenting irregularities in a responsive user's environment"); U.S. Pat. No. 7,631,065 ("System, method and computer program product for merging data in a network-based filtering and aggregating platform"); U.S. Pat. No. 7,496,670 ("Digital asset monitoring system and method"); U.S. Pat. No. 7,467,122 ("System for aiding the design of product configuration"); U.S. Pat. No. 7,394,817 ("Distributed data caching in hybrid peer-to-peer systems"); U.S. Pat. No. 7,346,675 ("System, method and computer program product for contract-based aggregation"); U.S. Pat. No. 7,142,110 ("Automatic conditioning of data accumulated by sensors monitoring supply chain processes").

Figure 10:
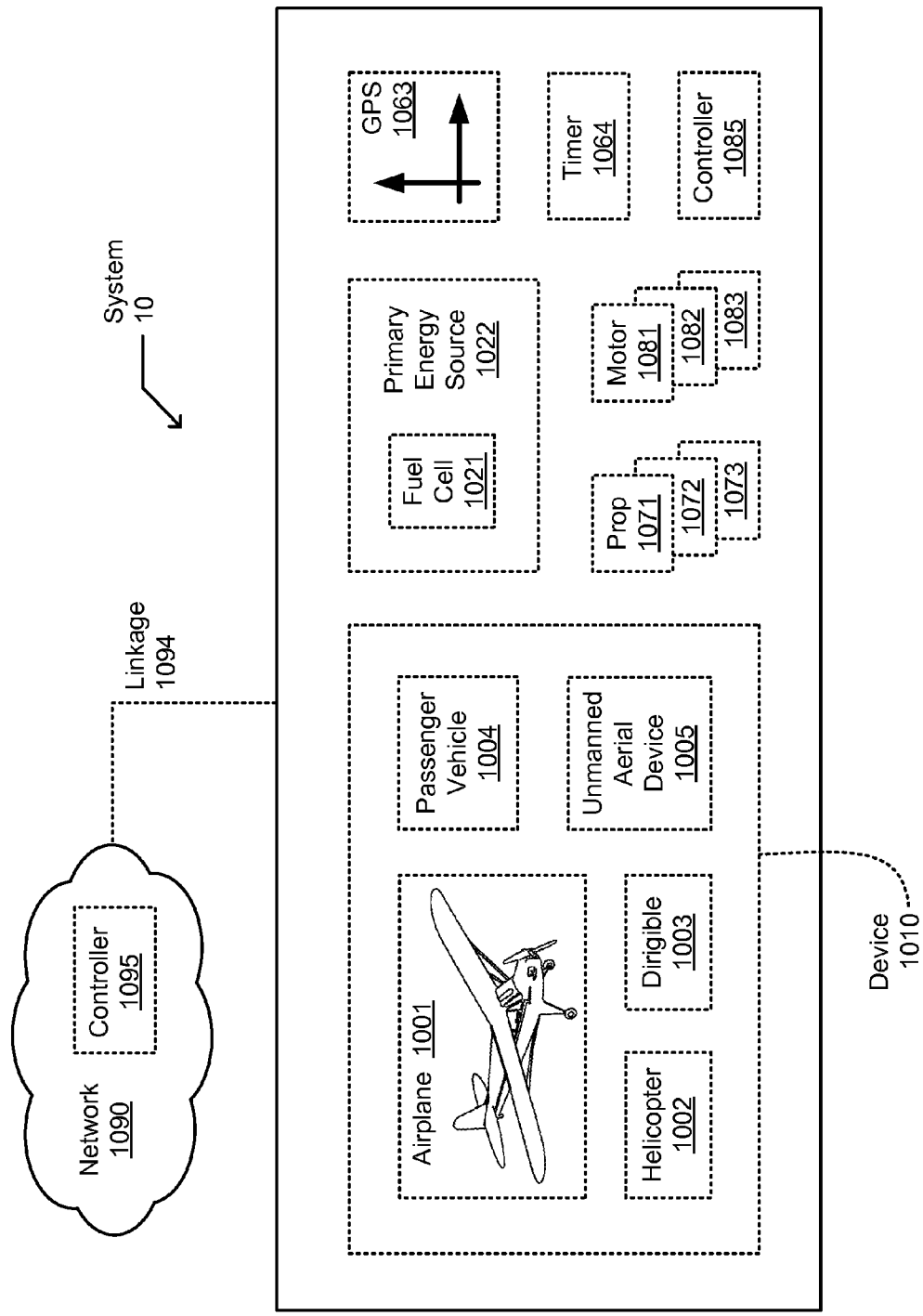
FIG. 10 depicts an exemplary environment featuring a device (UAD, e.g.) operably coupled with a network via a communication linkage.

FIG. 10 depicts another context in which one or more of the above-described systems may be implemented. System 10 comprises one or more instances of participating mobile devices 1010 such as airplanes 1001, helicopters 1002, or dirigibles 1003. Each such mobile device 1010 may, moreover, comprise a passenger vehicle 1004 (like a car 602 or passenger airplane, e.g.), a handheld device (like a cellular telephone or UAD 201, UAD 202 of FIG. 2, e.g.), or another unmanned aerial device 1005 (such as a glider, balloon, rocket, helicopter 1002, dirigible 1003, or other such device configured to be maneuvered in flight, e.g.). In some contexts, moreover, such a device may include one or more instances of fuel cells 1021 or batteries or other primary energy sources 1022 or secondary energy sources (a photovoltaic cell, e.g.); wireless communication linkages 1094 (operably coupled with one or more controllers 1095 in network 1090 and remote from device 1010, e.g.); a global positioning system (GPS) 1063; timers 1064; or local controllers 1085 operable for controlling one, two, or several props 1071, 1072, 1073 or wheels 683 (via one or more motors 1081, 1082, 1083, e.g.).

In light of teachings herein, numerous existing techniques may be applied for configuring special-purpose circuitry or other structures effective for remotely, autonomously, or otherwise controlling one or more devices in flight without undue experimentation or for configuring other decisions and devices as described herein. See, e.g., U.S. Pat. No. 8,090,525 ("Device and method for providing automatic assistance to air traffic controllers"); U.S. Pat. No. 8,078,395 ("Control system for automatic circle flight"); U.S. Pat. No. 7,890,221 ("Method and device for consolidation by software synchronisation in flight control computers"); U.S. Pat. No. 6,926,233 ("Automatic formation flight control system (AFFCS)—a system for automatic formation flight control of vehicles not limited to aircraft, helicopters, or space platforms"); U.S. Pat. No. 6,847,865 ("Miniature, unmanned aircraft with onboard stabilization and automated ground control of flight path"); U.S. Pat. No. 6,604,044 ("Method for generating conflict resolutions for air traffic control of free flight operations"); U.S. Pat. No. 6,552,669 ("Automated air-traffic advisory system and method"); U.S. Pat. No. 6,538,581 ("Apparatus for indicating air traffic and terrain collision threat to an aircraft"); U.S. Pat. No. 6,526,377 ("Virtual presence"); U.S. Pat. No. 6,133,867 ("Integrated air traffic management and collision avoidance system").

Figure 11:
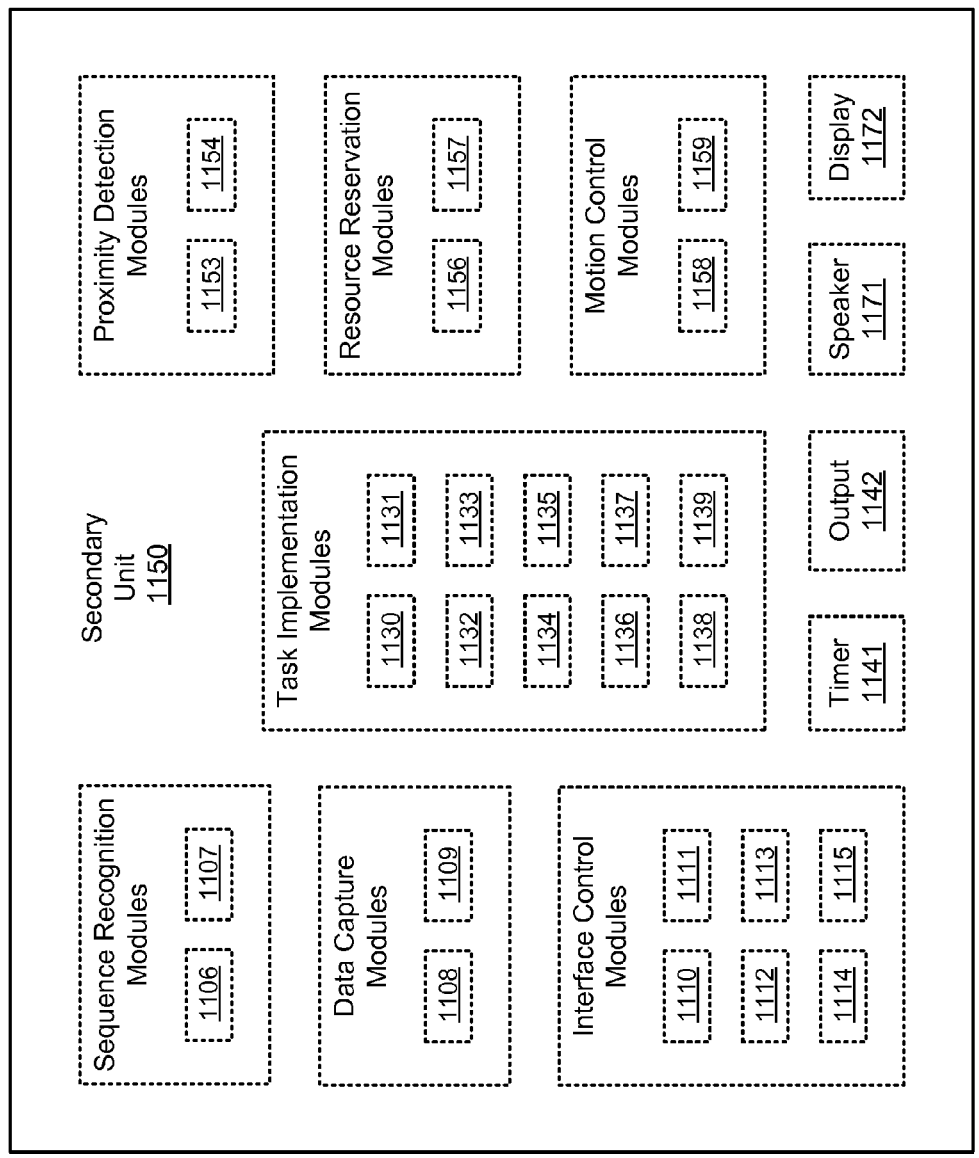
FIG. 11 depicts an exemplary environment featuring a secondary unit.

Another system in which one or more technologies may be implemented is shown in FIG. 11. Secondary unit 1150 comprises one or more instances of sequence recognition modules 1106, 1107; data capture modules 1108, 1109; interface control modules 1110, 1111, 1112, 1113, 1114, 1115; task implementation modules 1130, 1131, 1132, 1133, 1134, 1135, 1136, 1137, 1138, 1139; timers 1141 or other delay elements; outputs 1142 (speakers 1171 or displays 1172 configured to present data to device user 226, e.g.); proximity detection modules 1153, 1154; resource reservation modules 1156, 1157; or motion control modules 1158, 1159. In some variants, one or more instances of secondary unit 1150 may be operably coupled with event/condition detection unit or may reside in one or more networks 190, 990, 1090 described above.

Figure 12:
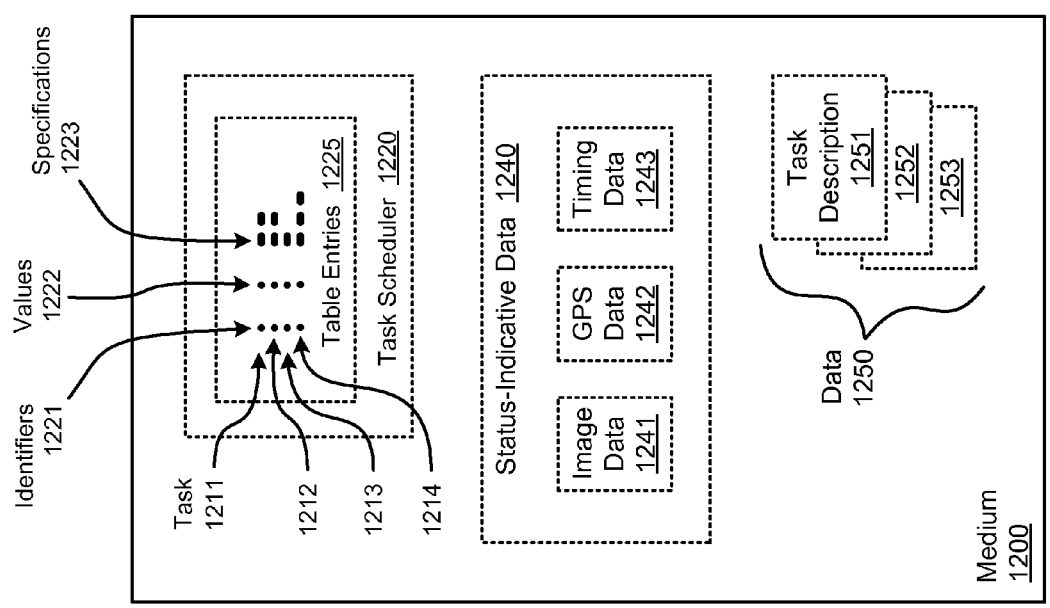
FIG. 12 depicts a physical medium residing in one or more of the above-described environments.

Another system in which one or more technologies may be implemented is shown in FIG. 12. A medium 1200 (of storage or transmission or display, e.g.) may include one or more instances of task scheduler 1220 containing or otherwise able to access table entries 1225 comprising one or more digitally represented tasks 1211, 1212, 1213, 1214 (each shown as a row, e.g.), each of which may include one or more instances of task identifiers 1221, values 1222, or specifications 1223. Medium 1200 may also include status-indicative data 1240 (comprising one or more of image data 1241, GPS data 1242, or timing data 1243, e.g.); task descriptions 1251, 1252, 1253; or other task-related data 1250 as described herein.

Figure 13:
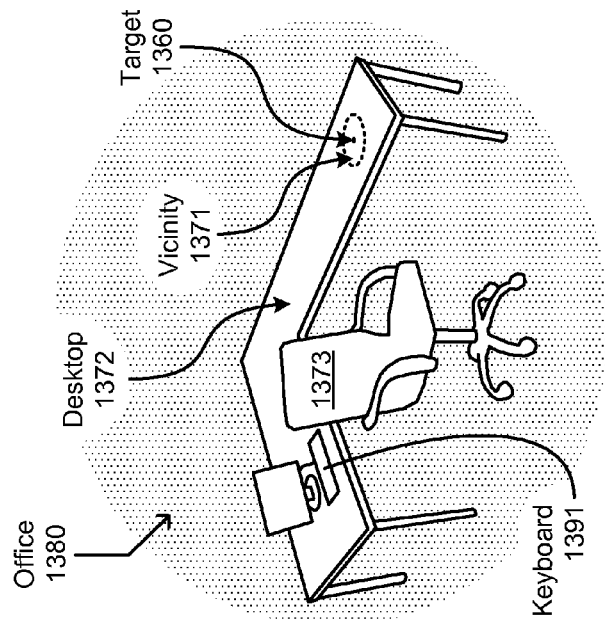
FIG. 13 depicts a chair, keyboard, and desktop in an office into which a UAD may enter.

Another context in which one or more technologies may be implemented is shown in FIG. 13, depicting a stationary computer (implementing interface device 310, e.g.) having a keyboard 1391 (implementing input 391, e.g.) and a user's chair 1373 in an office 1380. Office 1380 further comprises a desktop 1372 that supports or comprises a target 1360 (an ASIC 409, surface pattern, or other feature detectable by UAD 1005, e.g.) within a vicinity 1371 of which a delivery or landing (by or of UAD 1005, e.g.) may occur as described below.

Figure 14:
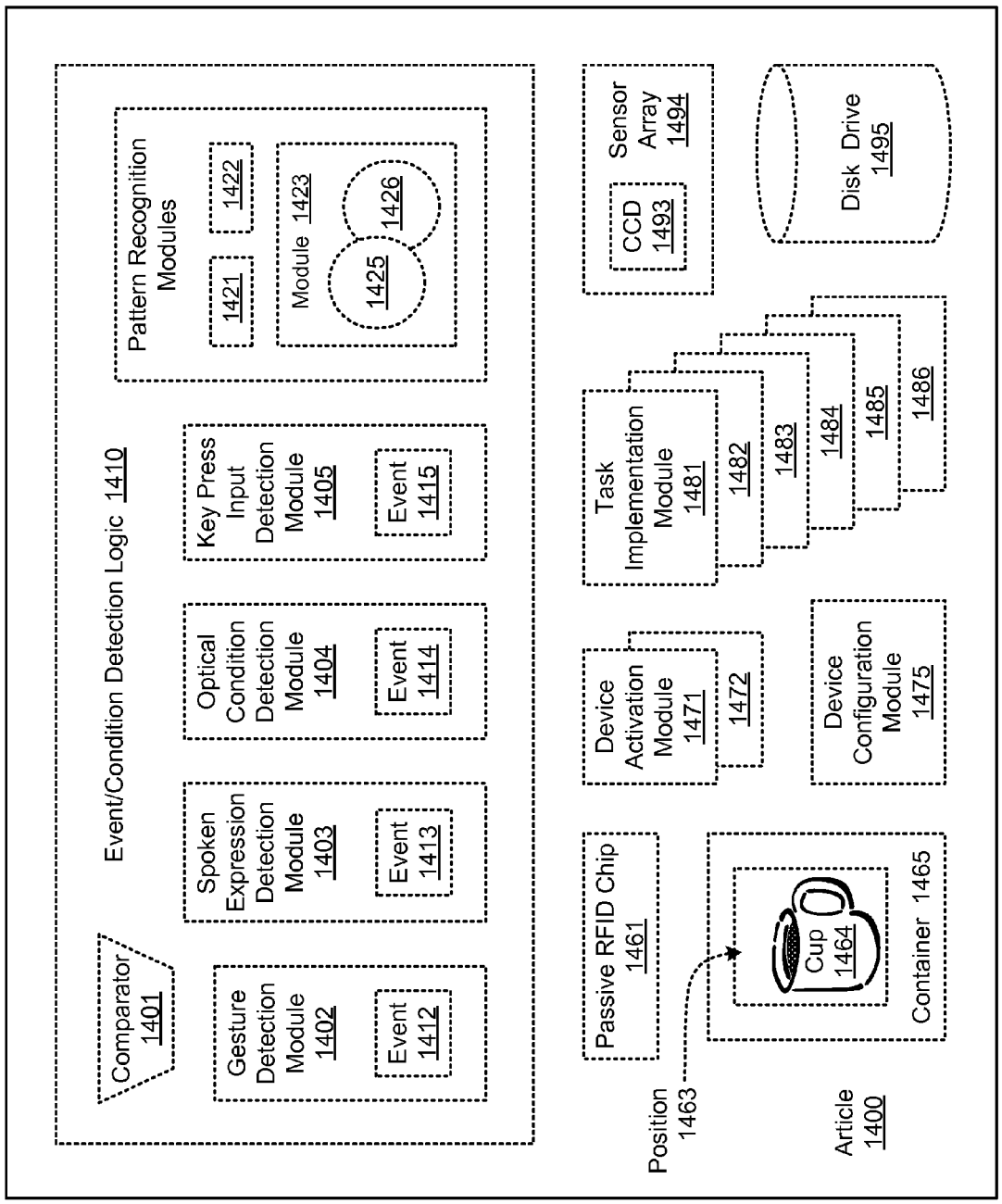
FIG. 14 depicts an exemplary environment featuring an article of manufacture.

Another context in which one or more technologies may be implemented is shown in FIG. 14, depicting one or more instances of articles 1400 each comprising a comparator 1401 or other event/condition logic 1410 that may (optionally) implement target 1360 as well. Alternatively or additionally, article 1400 may comprise one or more instances of passive radio frequency identification (RFID) chips 1461; a cup 1464 or other container 1465 above which is a position 1463 to which UAD 1005 may fly; device activations modules 1471, 1472; device configuration modules 1475; task implementation modules 1481, 1482, 1483, 1484, 1485, 1486; device configuration modules 1475; task implementation modules 1481, 1482, 1483, 1484, 1485, 1486; charge-coupled devices (CCD's) 1493 or other sensor arrays 1494; or disk drives 1495. In some contexts, as variously described herein, article 1400 (implementing UAD 1005, e.g.) may include a sensor array 1494 (camera, e.g.) configured to depict (some or all of) a vicinity (chair 1373, e.g.) of an object (target 1360, e.g.) or a person 727 or of itself.

Another context in which one or more technologies may be implemented is shown in FIG. 20, depicting various structures forming a part of UAD 1005 (on a bottom or side thereof, e.g.) having one or more mechanical linkages 2040 (adhesives or tethers or clamps or other such releasable support mechanisms 2020, e.g.) that can physically engage or disengage one or more cargo modules 2090. As shown, each such cargo module 2090 may include one or more instances of packages 2050 (having a hole 2049 therethrough, e.g.); syringes 2061, inhalers 2062, capsules 2063 (containing a dose 2064 of therapeutic material, e.g.), or other such products 2060 (in a dispenser 2038, e.g.); data handling units 2078 (comprising a camera 2071, display 2072, or other device having a primary function of handling data, e.g.); or releasable UAD energy sources (battery 2085, e.g.). In a variant of structure 2030 configured to engage package 2050, for example, a cross-sectional view 2048 across hole 2049 is shown in a context in which package 2050 protrudes into a groove 2026 of UAD 1005. Post 2006 may be moved (e.g. magnetically by a solenoid or mechanically by a spring, not shown) toward recess 2023 (to the right, as shown) to engage package 2050 or away from recess 2023 (to the left, as shown) to disengage package 2050, as described below. Alternatively or additionally, UAD 1005 may include a robotic arm 2039 or similar structure 2030 for engaging or disengaging cargo module 2090 (pursuant to an engagement trigger or disengagement trigger from of one or more task implementation modules 1130-1139, 1481-1486, e.g.).

In some embodiments, a material is "therapeutic" if it includes a pharmaceutical (e.g. an antibiotic, pain reliever, or stimulant), a nutraceutical (e.g. a dietary supplement or other therapeutic food ingredient), a topically applied material (e.g. a liniment or lotion prescribed or used in a medical other health-related practice), or other product or components (e.g. propellants, inhalants, inoculants, or resorbable binders or coatings) intended primarily to maintain or improve a subject's health or performance. Some embodiments relate to a delivery of a "single dose" (±50%, e.g.) generally signifying a prescribed or recommended amount of a material ("two aspirin," e.g.) to be administered into or onto a subject's body either (1) periodically or (2) at one time.

In light of teachings herein, numerous existing techniques may be applied for configuring special-purpose circuitry or other structures effective for configuring devices to engage or disengage data handling units, medical products, energy sources, or other such modular cargo without undue experimentation or for configuring other decisions and devices as described herein. See, e.g., U.S. Pat. No. 8,192,698 ("Sampling probe, gripper and interface for laboratory sample management systems"); U.S. Pat. No. 8,179,496 ("Display casing capable of accommodating LCD panel modules of different sizes"); U.S. Pat. No. 8167236 ("Hybrid lift air vehicle"); U.S. Pat. No. 8,164,302 ("System for replenishing energy sources onboard different types of automatic vehicles"); U.S. Pat. No. 8,141,814 ("Lighter-than-air vertical load lifting system"); U.S. Pat. No. 8,128,026 ("Removable cargo pod with lifting mechanism and open top"); U.S. Pat. No. 8,122,982 ("Mobile robot systems and methods"); U.S. Pat. No. 8,101,434 ("Method for LED-module assembly"); U.S. Pat. No. 8,091,463 ("Machine gun ammunition holder incorporating center of gravity downward ejection-deflector"); U.S. Pat. No. 8,066,460 ("Apparatus and method for cargo loading system"); U.S. Pat. No. 8,037,839 ("Device for handling a load hoisted between two locations offset both vertically and horizontally"); U.S. Pat. No. 8,029,228 ("Cable hoisting apparatus"); U.S. Pat. No. 7,919,060 ("Dispenser for flattened articles"); U.S. Pat. No. 7,913,370 ("Method and apparatus for assembling exterior automotive vehicle body components onto an automotive vehicle body"); U.S. Pat. No. 7,750,778 ("System and method for attachment of objects"); U.S. Pat. No. 7,717,255 ("End of arm tool, apparatus, and method of engaging an article"); U.S. Pat. No. 7,648,513 ("Surgical manipulator for a telerobotic system"); U.S. Pat. No. 7,641,461 ("Robotic systems for automated construction"); U.S. Pat. No. 7,549,204 ("Methods for picking and placing workpieces into small form factor hard disk drives"); U.S. Pat. No. 7,474,212 ("Object tagged with RFID tag and device and method for processing it"); and U.S. Pat. No. 7,252,453 ("Robot arm coupling apparatus").

Figure 21:
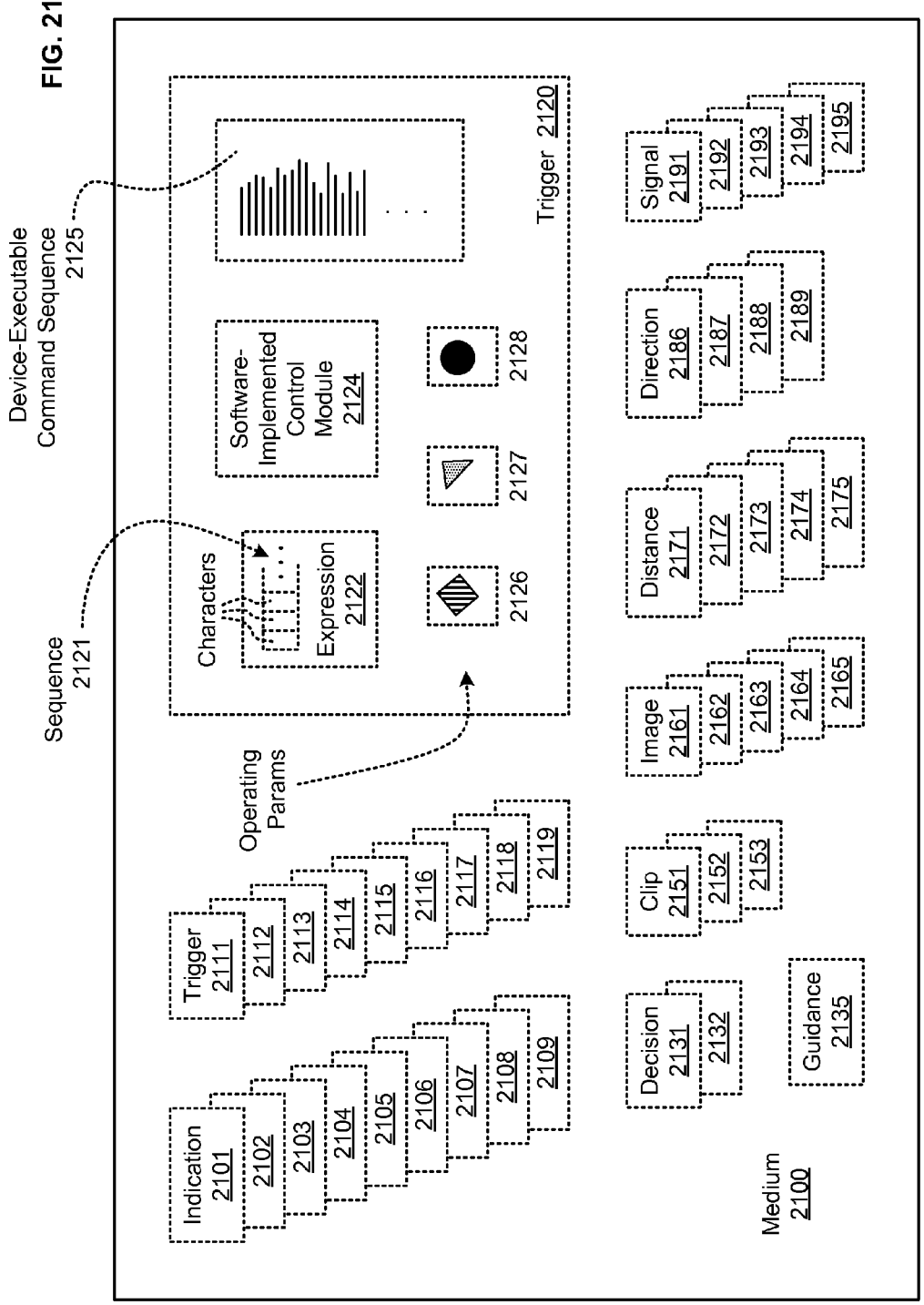
FIGS. 21-22 depict physical media residing in one or more of the above-described environments.

Another context in which one or more technologies may be implemented is shown in FIG. 21. A medium 2100 (configured to implement storage or transmission or display, e.g.) may bear one or more instances of indications 2101, 2102, 2103, 2104, 2105, 2106, 2107, 2108, 2109; triggers 2111, 2112, 2113, 2114, 2115, 2116, 2117, 2118, 2119, 2120; guidance 2130; decisions 2131, 2132, 2133, 2134; clips 2151, 2152, 2153; images 2161, 2162, 2163, 2164, 2165; distances 2171, 2172, 2173, 2174, 2175; directions 2186, 2187, 2188, 2189; or signals 2191, 2192, 2193, 2194, 2195. Each of these items may (optionally) include two or more components. In various embodiments, for example, one or more of triggers 2110-2120 may comprise one or more instances of a character sequence 2121 or similar digital expression 2122 (expressing a scalar operating parameter 2127, an alphanumeric identifier, or other such operating parameter 2128, e.g.) to which a trigger recipient (an instance of task implementation module 1130 residing in UAD 1005 or another module depicted in FIGS. 1-20, e.g.) is configured to respond. Each such trigger may likewise comprise one or more software-implemented control modules 2124 (comprising a device-implemented command sequence 2125, e.g.) or operating parameters 2126, 2127, 2128.

Several variants described herein refer to software or other device-detectable "implementations" such as one or more instances of computer-readable code, transistor or latch connectivity layouts or other geometric expressions of logical elements, firmware or software expressions of transfer functions implementing computational specifications, digital expressions of truth tables, or the like. Such instances can, in some implementations, include source code or other human-readable portions. Alternatively or additionally, functions of implementations described herein may constitute one or more device-detectable outputs such as decisions, manifestations, side effects, results, coding or other expressions, displayable images, data files, data associations, statistical correlations, streaming signals, intensity levels, frequencies or other measurable attributes, packets or other encoded expressions, or the like from invoking or monitoring the implementation as described herein.

In some embodiments, a "state" of a component may comprise "available" or some other such state-descriptive labels, an event count or other such memory values, a partial depletion or other such physical property of a supply device, a voltage, or any other such conditions or attributes that may change between two or more possible values irrespective of device location. Such states may be received directly as a measurement or other detection, in some variants, and/or may be inferred from a component's behavior over time. A distributed or other composite system may comprise vector-valued device states, moreover, which may affect dispensations or departures in various ways as exemplified herein.

Figure 22:
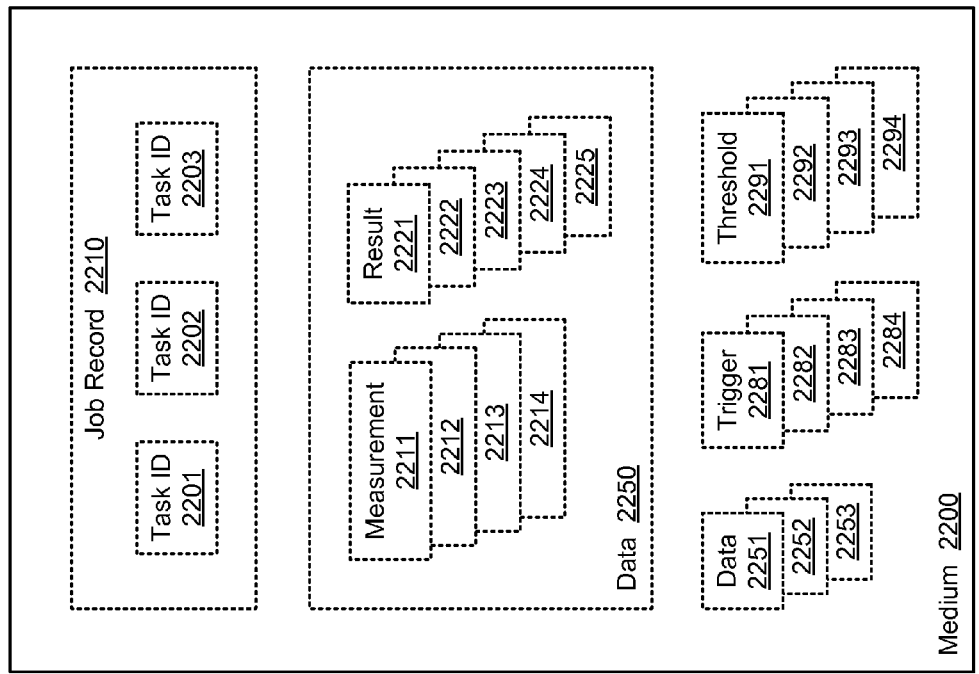

Another context in which one or more technologies may be implemented is shown in FIG. 22. A medium 2200 (configured to implement storage or transmission or display, e.g.) may bear one or more instances of job records 2210; data 2250, 2251, 2252, 2253 (comprising measurements 2211, 2212, 2213, 2214 or images or other results 2221, 2222, 2223, 2224, 2225, e.g.); triggers 2281, 2282, 2283, 2284; thresholds 2291, 2292, 2293, 2294; or components of other media 195, 410, 1200, 2100 described above. In some variants, for example, a job record may include one or more task identifiers 2201, 2202, 2203 configured to identify, in respective embodiments, any of the other tasks indicated herein to be implemented in one or more devices.

Figure 28:
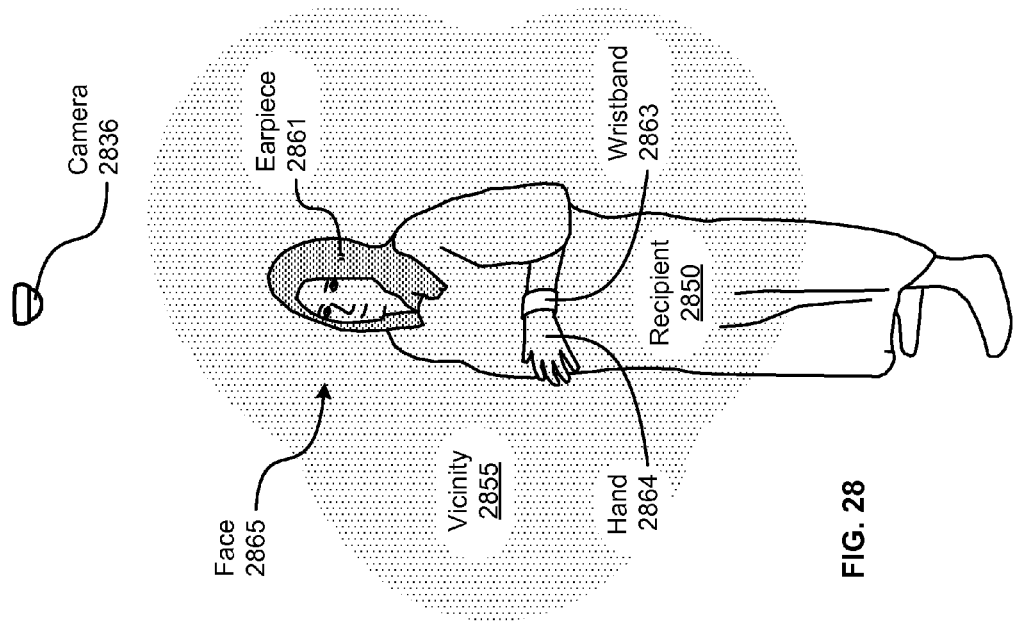
FIG. 28 depicts an exemplary environment featuring a camera mounted on a building configured to observe a person.

Another context in which one or more technologies may be implemented is shown in FIG. 28. A mounted camera 2836 (supported by a building or other stationary structure, e.g.) is configured to observe one or more instances of a particular person (a recipient 2850 of a delivery, e.g.) or a portion thereof (a hand 2864 or face 2865, e.g.) or a wearable device (an earpiece 2861 or wristband 2863, e.g.) or a partial or entire vicinity 2855 (room or other facility, e.g.) of one of these entities. Moreover in some contexts, as further described below, recipient 2850 may be a user of one or more of the above-described devices (in vicinity 2855, e.g.).

Figure 23:
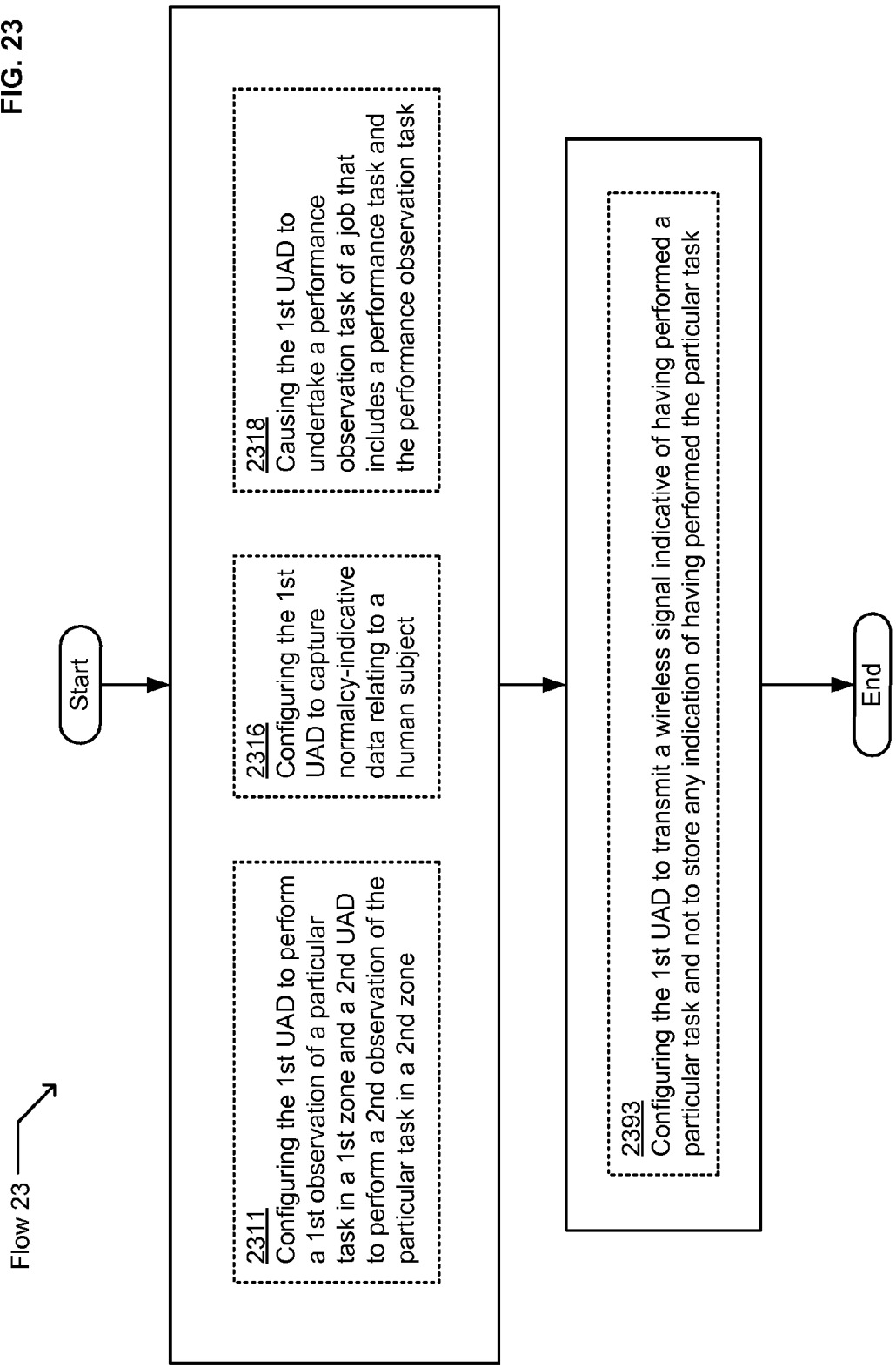
FIGS. 23-27 each depict intensive and extensive operations that may be performed in conjunction with one or more high-level logic flows shown in FIGS. 15-19.

With reference now to flow 23 of FIG. 23 and to other flows 15-19 described above, in some variants, one or more intensive operations 2311, 2316, 2318 described below may (optionally) be performed in conjunction with one or more intensive operations 51-55 described above. Alternatively or additionally, extensive operation 2393 described below may likewise comprise or be performed in conjunction with one or more extensive operations 81-85 described above.

Intensive operation 2311 describes configuring the first unmanned aerial device to perform a first observation of a particular task in a first zone and a second unmanned aerial device to perform a second observation of the particular task in a second zone (e.g. task implementation module 1138 transmitting a trigger 2282 causing UAD 801 to capture an audio or video clip 2151 of a person 726 carrying UAD 701 seeking device 775 in zone 781 and also transmitting a trigger 2283 instructing UAD 802 to capture an audio or video clip 2152 of the person 726 seeking device 775 in zone 782). This can occur, for example, in a context in which one or more UAD's 701 or people 726 are performing the particular task 499 (monitoring person 726 seeking device 775, e.g.) across one or more zone boundaries 789; in which secondary unit 1150 includes event/condition detection unit 400 and media 2100, 2200; in which at least one UAD 801, 802 contains or otherwise interacts with secondary unit 1150; in which such UAD's 801, 802 or people 726 have different UAD operating restrictions in respective zones 781, 782 (UAD 801 lacking permission to move or transmit only within zone 782, for example, or UAD 802 lacking permission to move or transmit only within zone 781); and in which adequate surveillance of the entire task 499 would otherwise be prohibited (by the owners of the respective zones 781, 782, e.g.).

In light of teachings herein, numerous existing techniques may be applied for configuring special-purpose circuitry or other structures effective for coordinating surveillance among two or more observers without undue experimentation or for configuring other decisions and devices as described herein. See, e.g., U.S. Pat. No. 8,180,107 ("Active coordinated tracking for multi-camera systems"); U.S. Pat. No. 7,947,936 ("Apparatus and method for cooperative multi target tracking and interception"); U.S. Pat. No. 7,739,157 ("Method of tracking the real time location of shoppers, associates, managers and vendors through a communication multi-network within a store"); U.S. Pat. No. 7,647,232 ("Real-time team coordination system for reconnaissance and surveillance missions"); U.S. Pat. No. 7,295,106 ("Systems and methods for classifying objects within a monitored zone using multiple surveillance devices"); U.S. Pat. No. 6,999,876 ("Modular architecture for rapid deployment and coordination of emergency event field surveillance"); U.S.

Pat. No. 6,963,279 ("System and method for transmitting surveillance signals from multiple units to a number of points"); U.S. Pat. No. 6,577,976 ("Method for dynamic autocalibration of a multi-sensor tracking system and apparatus incorporating it therein"); U.S. Pat. No. 6,333,718 ("Continuous multi-satellite tracking"); U.S. Pat. No. 6,084,827 ("Dual-head multibeam sonar apparatus and method for tracking objects underwater"); U.S. Pat. No. 6,055,523 ("Method and apparatus for multi-sensor, multi-target tracking using a genetic algorithm").

Intensive operation 2316 describes configuring the first unmanned aerial device to capture normalcy-indicative data relating to a human subject (e.g. task implementation module 1135 causing, by transmitting an appropriate trigger 2281, a data capture module 1108 to record one or more scalar measurements 2211-2213 or other data 2250-2253 directly or indirectly indicative of whether or not an item recipient 555, user 226, 626 or other human subject meets one or more recognizable criteria indicative of the human subject being impaired or otherwise abnormal). This can occur, for example, in a context in which a primary unit 110 contains a data capture module 1108 of one secondary unit 1150 and receives the trigger 2281 from another secondary unit 1150; in which data 2251 comprises a video clip of the human subject taking something (a purse, e.g.) previously carried by another and then running away (at a pace greater than 4 miles per hour within 5 seconds of the taking event, e.g.); and in which primary unit 110 also implements one or more media 2200 of a "first" UAD as described above. See, e.g., FIG. 2 or 5-10. In some contexts, such optically detectable events 1414 or conditions may be recognizable (as negatively indicative of normalcy, e.g.) by a corresponding optical condition detection module 1404 or by security personnel remotely viewing such data 2250. Alternatively or additionally, data 2252 may comprise (1) an infrared image indicating warmer-than-normal or cooler-than-normal regions of the human subject's skin; (2) one or more scalar measurements 2211, 2212 of the subject's body temperature, exhaled gas analysis (detecting a ketone concentration or other indication of intoxication, e.g.), rates (of respiration, speech, movement, or heartbeats, e.g.), or other such biometric parameters. Such events 1415 or conditions may be device-detectable or humanly recognizable (as negatively indicative of normalcy, e.g.) by a corresponding optical condition detection module 1404, by another pattern recognition module 1421, or by a person remotely viewing such data 2251-2253 in real time. In some contexts, for example, pattern recognition module 1421 may comprise a comparator 1401 configured to generate one or more results 2221, 2222 ("normal," e.g.) of comparing one or more performance or biometric measurements 2211-2213 of a user 226, 626 each against one or more corresponding normalcy-indicative thresholds 2291-2293 (maxima, e.g.). Such recognition may, for example, trigger the "first" UAD to obtain additional images or measurements 2214 pertaining to the apparent normalcy of the human subject.

In light of teachings herein, numerous existing techniques may be applied for configuring special-purpose circuitry or other structures effective for obtaining measurements, comparison results, or other normalcy-indicative data without undue experimentation or for configuring other decisions and devices as described herein. See, e.g., U.S. Pat. No. 8,135,957 ("Access control system based on brain patterns"); U.S. Pat. No. 8,061,842 ("Method of eye aliveness testing and device for eye aliveness testing"); U.S. Pat. No. 7,809,163 ("Method for prohibiting a person with a facial mask to operate an automatic teller machine"); U.S. Pat. No. 7,840,346 ("Real time performance comparison"); U.S. Pat. No. 7,571,101 ("Quantifying psychological stress levels using voice patterns"); U.S. Pat. No. 7,825,815 ("Apparatus, systems, and methods for gathering and processing biometric and biomechanical data"); U.S. Pat. No. 7,733,214 ("System and methods for the remote measurement of a person's biometric data in a controlled state by way of synchronized music, video and lyrics"); U.S. Pat. No. 8,094,009 ("Health-related signaling via wearable items"); U.S. Pat. No. 8,145,199 ("Controlling mobile device functions"); U.S. Pat. No. 8,211,035 ("System and method for monitoring health using exhaled breath"); U.S. Pat. No. 7,477,993 ("Multiple sensing system and device"); U.S. Pat. No. 8,172,459 ("Apparatus and method for measuring biologic parameters"); U.S. Pat. No. 8,108,083 ("Vehicular system which retrieves hospitality information promoting improvement of user's current energy value based on detected temporal change of biological condition"); U.S. Pat. No. 7,787,663 ("System and method for detecting thermal anomalies").

Intensive operation 2318 describes causing the first unmanned aerial device to undertake a performance observation task of a job that includes a performance task and the performance observation task (e.g. task implementation module 1137 transmitting to UAD 501, as the "first" UAD, a task identifier 2201 corresponding to a task description 1251 calling for specific status-indicative data 1240 relating to another device 1010 undertaking to fulfill a performance task description 1252 corresponding to task identifier 2202). This can occur, for example, in which secondary unit 1150 and media 1200, 2200 reside aboard UAD 501; in which the "performance" specified by task description 1252 comprises delivering an envelope 551; in which task description 1251 relates to obtaining one or more of image data 1241 (including photograph 553, e.g.), GPS data 1242 (of destination 530, e.g.), or timing data 1243 documenting the delivery; and in which such observation and performance are respectively identified by task identifiers 2201, 2202 of a single common job record 2210. Alternatively or additionally, such task description 1251 and other task descriptions 1252, 1253 may comprise job description data 1130 managed and delegated by a common task implementation module 1137. Other such task identifiers or descriptions may (optionally) comprise a scalar or other operating parameter 2126 of one or more triggers 421-423, 2111-2120 transmitted by task implementation modules 1130-1139, for example, as described herein.

In light of teachings herein, numerous existing techniques may be applied for configuring special-purpose circuitry or other structures effective for assigning tasks to respective devices without undue experimentation or for configuring other decisions and devices as described herein. See, e.g., U.S. Pat. No. 7,945,470 ("Facilitating performance of submitted tasks by mobile task performers"); U.S. Pat. No. 8,127,300 ("Hardware based dynamic load balancing of message passing interface tasks"); U.S. Pat. No. 7,716,667 ("Migrating virtual machines among computer systems to balance load caused by virtual machines"); U.S. Pat. No. 8,200,084 ("Encoding for information needed for routing and wavelength assignment in wavelength switched optical networks"); U.S. Pat. No. 8,181,168 ("Memory access assignment for parallel processing architectures"); U.S. Pat. No. 7,665,092 ("Method and apparatus for distributed state-based load balancing between task queues"); U.S. Pat. No. 8,184,860 ("Image processing device for controlling a plurality of tasks"); U.S. Pat. No. 7,996,893 ("Determining roles for automated tasks in a role-based access control environment"); U.S. Pat. No. 8,184,860 ("Image processing device for controlling a plurality of tasks").

Extensive operation 2393 describes configuring the first unmanned aerial device to transmit a wireless signal indicative of having performed a particular task and not to store any indication of having performed the particular task (e.g. task implementation module 1136 transmitting a trigger 2114 to which a component of UAD 1005 responds by transmitting one or more optical or other wireless signals 454 indicative of UAD 1005 having completed a particular task 491-499 without any component borne by UAD 1005 storing any indication of the particular task having been performed). This can occur, for example, in a context in which volatile memory 395 contains an indication 2108 of such completion that task implementation module 1136 includes in wireless signal 454 and in which task implementation module 1136 comprises event/condition detection unit 400. Alternatively or additionally, task implementation module 1136 may be configured to generate an indication 2108 of such completion (in response to one or more of photographs 553, 554 or GPS data 1242 or timing data 1243 documenting a completed delivery task, e.g.) for inclusion in wireless signal 454.

Figure 24:
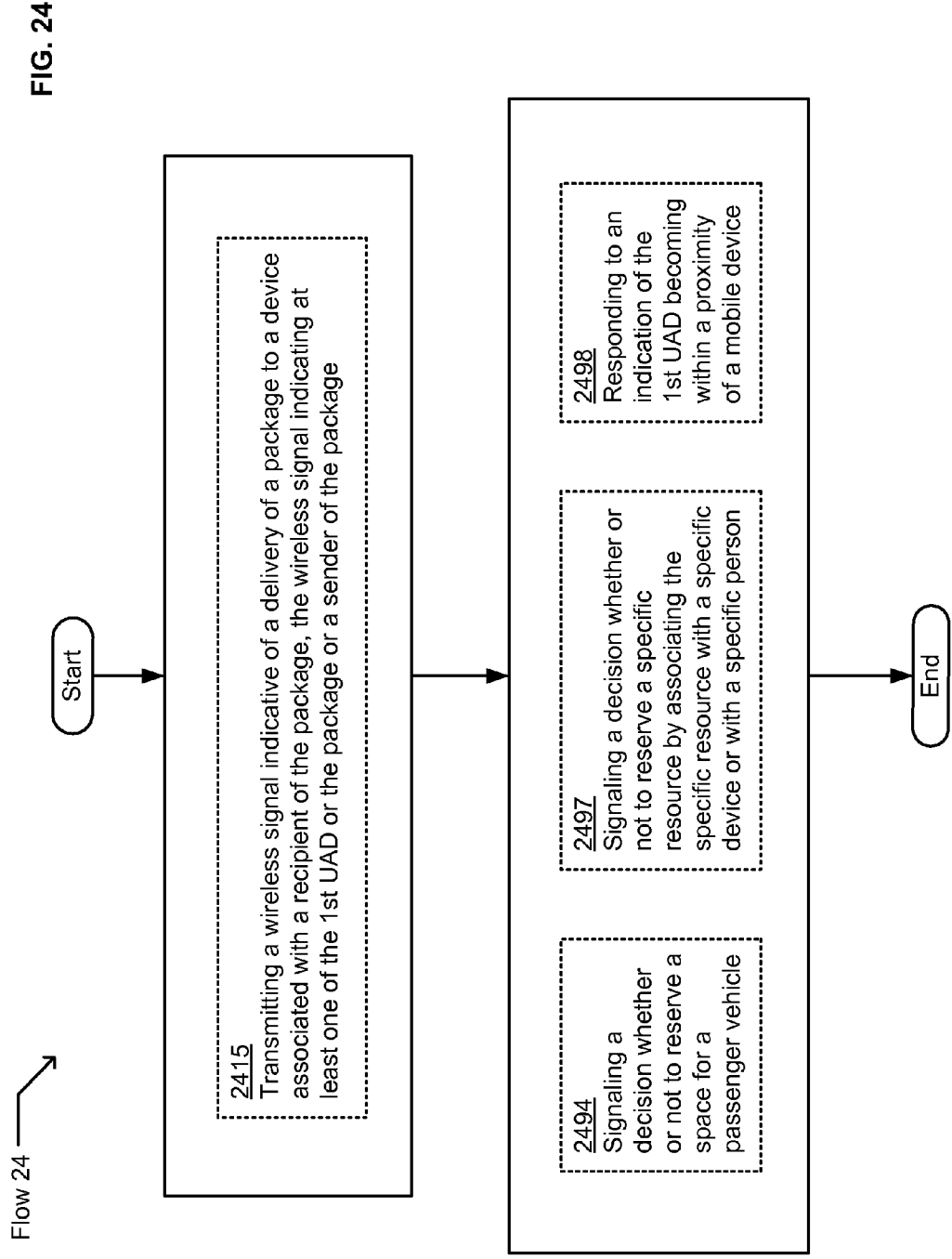

With reference now to flow 24 of FIG. 24 and to other flows 15-19, 23 described above, in some variants, intensive operation 2415 described below may (optionally) be performed in conjunction with one or more intensive operations described above. Alternatively or additionally, one or more extensive operations 2494, 2497, 2498 described below may likewise comprise or be performed in conjunction with one or more extensive operations described above.

Intensive operation 2415 describes transmitting a wireless signal indicative of a delivery of a package to a device associated with a recipient of the package, the wireless signal indicating at least one of the first unmanned aerial device or the package or a sender of the package (e.g. data delivery module 154 transmitting a wireless signal 451 indicative of a delivery of a package 2050 into a vicinity of an article 1400 associated with a purchaser of the package 2050, the wireless signal 451 indicating at least one of the 1st UAD 1005 or the package 2050 or a sender 510 of the package 2050). This can occur, for example, in a context in which primary unit 110 resides in the "first" UAD 1005 or in another device 1010 described herein; in which the "vicinity" comprises the room in which article 1400 is situated; in which task implementation module 1481 transmits various operating parameters 2126-2128 (specified by a UAD user 226 or package sender 510, e.g.) relating to such delivery. One such sequence 2121, for example, may (optionally) comprise an alias 823 or other expression 2122 facilitating an identification of article 1400. Another such expression 2122 may comprise global positioning system (GPS) or other destination coordinates 605, 606 (of the article 1400, e.g. or of an alternative destination to be used if the "first" UAD 1005 cannot locate the article 1400, e.g.). Other such parameters may comprise one or more distances 2171-2175; directions 2186-2189; protocol identifiers, or other such indications 2101-2109 described herein.

In light of teachings herein, numerous existing techniques may be applied for configuring special-purpose circuitry or other structures effective for specifying how a delivery is to be performed without undue experimentation or for configuring other decisions and devices as described herein. See, e.g., U.S. Pat. No. 8,156,542 ("Conditional data delivery to remote devices"); U.S. Pat. No. 8,112,475 ("Managing data delivery based on device state"); U.S. Pat. No. 8,090,826 ("Scheduling data delivery to manage device resources"); U.S. Pat. No. 7,647,230 ("Method and apparatus for tracking a special service delivery of a mail item created by an office worker"); U.S. Pat. No. 7,587,369 ("Trusted and secure techniques, systems and methods for item delivery and execution"); U.S. Pat. No. 7,401,030 ("Method and system for tracking disposition status of an item to be delivered within an organization"); U.S. Pat. No. 7,225,983 ("Intelligent parcel monitoring and controlling apparatus and method and terminal for executing real-time parcel pickup and delivery and operation method thereof"); U.S. Pat. No. 7,143,937 ("Systems and methods for utilizing a tracking label in an item delivery system"); U.S. Pat. No. 6,463,354 ("System and method for automatic notification of upcoming delivery of mail item").

Extensive operation 2494 describes signaling a decision whether or not to reserve a space for a passenger vehicle (e.g. resource reservation module 1156 transmitting a trigger 2118 that is effective to allocate parking space 648 for the use of car 602). This can occur, for example, in a context in which the trigger 2118 includes an affirmative decision 2133 (to reserve parking space 648, e.g.) that has been received from a person (user 626, e.g.) aboard the passenger vehicle; in which secondary unit 1150 resides in UAD 601 or in a stationary unit (at station 520, e.g.) operable to communicate with UAD 601 and in which resource reservation module 1156 maintains one or more records 964 indicating available and unavailable parking spaces (in the same parking lot, e.g.) monitored by UAD 601. In some contexts, moreover, UAD 601 may (optionally) perform operation 2494 by hovering or landing in parking space 648 to notify passersby that the space is taken.

In light of teachings herein, numerous existing techniques may be applied for configuring special-purpose circuitry or other structures effective for associating a thing or person with another thing or person without undue experimentation or for configuring other decisions and devices as described herein. See, e.g., U.S. Pat. No. 8,196,809 ("System and method for associating an absorbent article with a user"); U.S. Pat. No. 8,180,827 ("Method and apparatus for associating graphic icon in internet virtual world with user's experience in real world"); U.S. Pat. No. 8,160,615 ("Method and system for generating associations between a user profile and wireless devices"); U.S. Pat. No. 8,131,745 ("Associating user identities with different unique identifiers"); U.S. Pat. No. 8,051,429 ("Method for associating data bearing objects with user interface objects"); U.S. Pat. No. 8,006,194 ("Associating an object with a relevant data source"); U.S. Pat. No. 7,979,585 ("System and method to associate a private user identity with a public user identity"); U.S. Pat. No. 7,941,505 ("System and method for associating a user with a user profile in a computer network environment"); U.S. Pat. No. 7,787,870 ("Method and system for associating a user profile to a caller identifier").

Extensive operation 2497 describes signaling a decision whether or not to reserve a specific resource by associating the specific resource with a specific device or with a specific person (e.g. resource reservation module 157 transmitting one or more triggers 2113, 2120 effective for implementing or broadcasting an association of a sender 510 or device 775 with person 725). This can occur, for example, in a context in which network 190 comprises one or more systems 4-9 and media 1200, 2100, 2200 as described herein; in which trigger 2113 includes one expression 2122 for the specific resource (sender 510 or device 775, e.g.) and another expression 2122 for the specific entity (device or person, e.g.) with which the specific resource is or will be associated. Alternatively or additionally, in some implementations, resource reservation module 1157 may perform operation 2497 by transmitting an indication 2103 that a specific resource (a modular data handling unit 2078, e.g.) not be reserved for a specific entity (UAD 201, e.g.) by associating the specific resource with another specific entity (UAD 202, e.g.). This can occur, for example, in a context in which the specific resource can only be associated with one such entity.

In light of teachings herein, numerous existing techniques may be applied for configuring special-purpose circuitry or other structures effective for allocating resources without undue experimentation or for configuring other decisions and devices as described herein. See, e.g., U.S. Pat. No. 8,204,770 ("Computer-implemented systems and methods for resource allocation"); U.S. Pat. No. 8,200,583 ("Method and system for leasing or purchasing domain names"); U.S. Pat. No. 8,099,339 ("Systems and methods for pharmacy inventory management"); U.S. Pat. No. 7,979,309 ("Method and system for automating inventory management of consumer items"); U.S. Pat. No. 7,956,769 ("Method and system for reservation-based parking"); U.S. Pat. No. 7,941,354 ("Method and system for lease of assets, such as trailers, storage devices and facilities"); U.S. Pat. No. 7,865,409 ("Vehicle inventory management system and method"); U.S. Pat. No. 7,839,526 ("Reservation of secondary printing devices in a substitute printing system"); U.S. Pat. No. 7,836,186 ("Automated adjustment of IP address lease time based on usage"); U.S. Pat. No. 7,797,077 ("System and method for managing vending inventory"); U.S. Pat. No. 7,680,691 ("Inventory management system using RFID"); U.S. Pat. No. 7,636,687 ("Method and system for completing a lease for real property in an on-line computing environment"); U.S. Pat. No. 7,636,669 ("Recreational outing reservation system").

Extensive operation 2498 describes responding to an indication of the first unmanned aerial device becoming within a proximity of a mobile device (e.g. proximity detection module 1153 determining whether UAD 1005 has come into a vicinity 2855 of an earpiece 2861, wristband 2863, or other article 1400 wearable by a person). This can occur, for example, in a context in which such an article 1400 (comprising device 775, e.g.) is worn by a person 725 who is moving (toward or away from UAD 1005, e.g.); in which proximity detection module 1153 resides within the (wearable or other mobile) device 775 or within the "first" UAD 1005; in which one or more components of such device are thereby able to detect a proximity of the other device; and in which proximity detection module 1153 responds by invoking one or more task implementation modules 1130-1139, 1481-1486 described herein.

A first device may "become within" a proximity of a second device by one or both such devices moving toward the other. Each proximity detection module 1153 may, in some instances, operate by having a sensor as a component of a first device that detects the other device becoming close enough to the sensor to be detected by the sensor, irrespective of which device(s) moved. Alternatively or additionally, some implementations of proximity detection module 1153 may reside remotely from both devices and may be configured to determine the devices' mutual proximity from their respective coordinates 605, 606. In some contexts, for example, a proximity of an object may comprise a room (of a patient in a hospital, e.g.) containing the object. In others, a proximity (of target 1360, e.g.) may comprise only an immediate vicinity 1371 (within a few centimeters, e.g.) of the object or may comprise an entire surface (desktop 1372, e.g.) on which such an object is positioned.

In light of teachings herein, numerous existing techniques may be applied for configuring special-purpose circuitry or other structures effective for computing a difference between locations without undue experimentation or for configuring other decisions and devices as described herein. See, e.g., U.S. Pat. No. 8,044,798 ("Passive microwave speed and intrusion detection system"); U.S. Pat. No. 8,026,850 ("Apparatus and method for computing location of a moving beacon using time difference of arrival and multi-frequencies"); U.S. Pat. No. 7,962,283 ("Deviation-correction system for positioning of moving objects and motion tracking method thereof"); U.S. Pat. No. 7,778,792 ("Systems and methods for location, motion, and contact detection and tracking in a networked audiovisual device"); U.S. Pat. No. 7,775,329 ("Method and detection system for monitoring the speed of an elevator car"); U.S. Pat. No. 7,671,795 ("Wireless communications device with global positioning based on received motion data and method for use therewith"); U.S. Pat. No. 7,647,049 ("Detection of high velocity movement in a telecommunication system"); U.S. Pat. No. 7,460,052 ("Multiple frequency through-the-wall motion detection and ranging using a difference-based estimation technique"); U.S. Pat. No. 7,242,462 ("Speed detection methods and devices"); U.S. Pat. No. 6,985,206 ("Baseball pitch speed measurement and strike zone detection devices"); U.S. Pat. No. 6,400,304 ("Integrated GPS radar speed detection system").

In light of teachings herein, numerous existing techniques may be applied for configuring special-purpose circuitry or other structures effective for detecting whether two devices are near one another without undue experimentation or for configuring other decisions and devices as described herein. See, e.g., U.S. Pat. No. 8,078,107 ("Automatic network and device configuration for handheld devices based on bluetooth device proximity"); U.S. Pat. No. 8,050,243 ("Method and system for evaluating proximity to a WLAN for a UMA/GAN compatible electronic device"); U.S. Pat. No. 8,019,283 ("Automatic data encryption and access control based on Bluetooth device proximity"); U.S. Pat. No. 7,769,984 ("Dual-issuance of microprocessor instructions using dual dependency matrices"); U.S. Pat. No. 7,574,077 ("Optical imaging device for optical proximity communication"); U.S. Pat. No. 7,289,184 ("Liquid crystal panel and equipment comprising said liquid crystal panel"); U.S. Pat. No. 7,010,098 ("Ultrasonic proximity detector for a telephone device"); U.S. Pat. No. 6,735,444 ("Method and system for locating a device using a local wireless link"); U.S. Pat. No. 6,114,950 ("Obstacle proximity warning device for vehicles").

Figure 25:
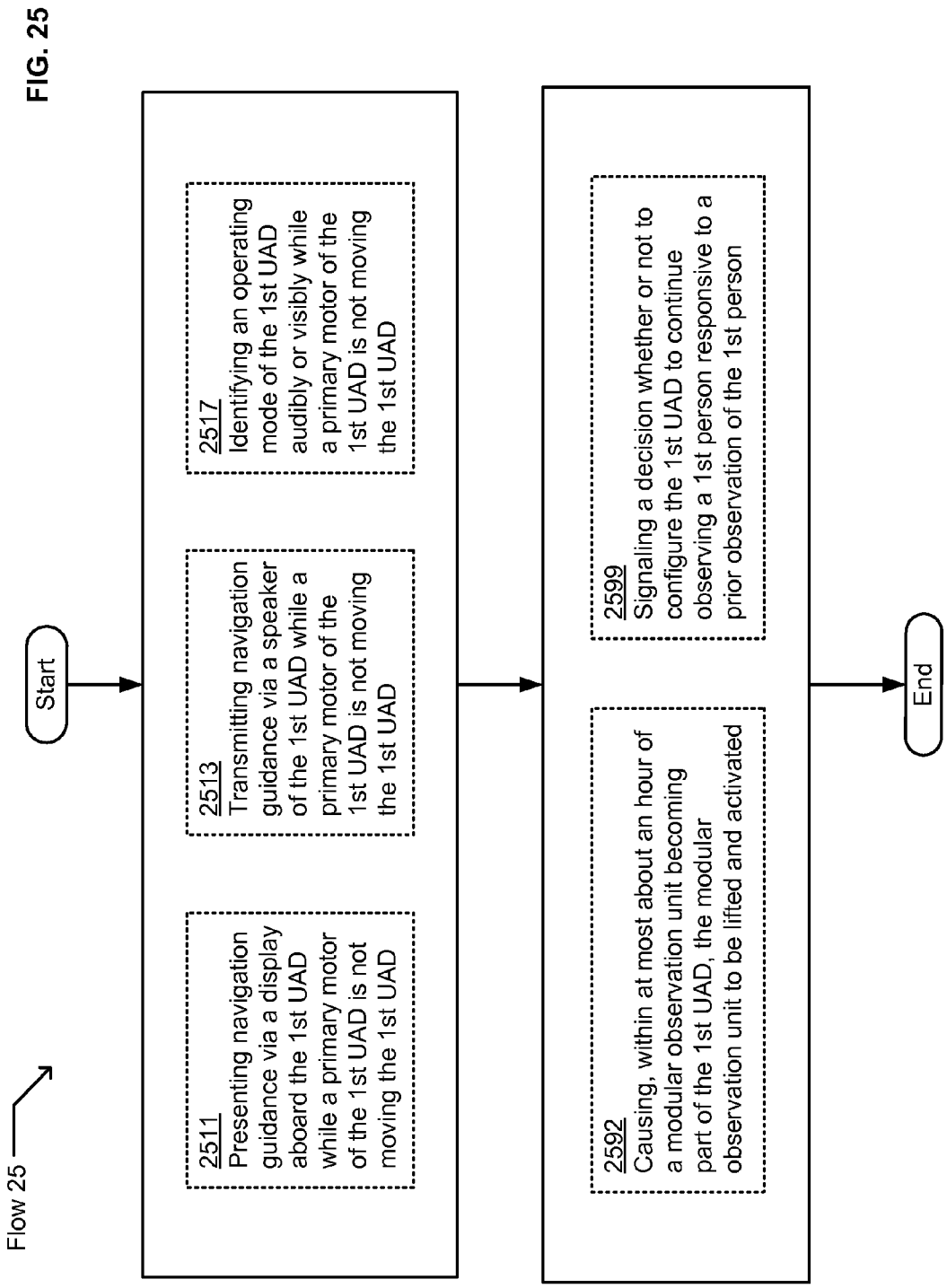

With reference now to flow 25 of FIG. 25 and to other flows 15-19, 23, 24 described above, in some variants, one or more intensive operations 2511, 2513, 2517 described below may (optionally) be performed in conjunction with one or more intensive operations described above. Alternatively or additionally, one or more extensive operations 2592, 2599 described below may likewise comprise or be performed in conjunction with one or more extensive operations described above.

Intensive operation 2511 describes presenting navigation guidance via a display aboard the first unmanned aerial device while a primary motor of the first unmanned aerial device is not moving the first unmanned aerial device (e.g. triggering interface control module 1111 to output navigation guidance 2130 via a touchscreen or other display 1172 borne by UAD 1005 after controller 1085 stops motor 1081). This can occur, for example, in a context in which UAD 1005 includes a secondary unit 1150 that includes one or more media 2110 and in which controller 1085 switches motor 1081 off. Alternatively or additionally, task implementation module 1131 may perform operation 2511 by displaying guidance 2130 (arrows, words, or other turn-by-turn navigation instructions for a pedestrian or motor vehicle, e.g.). In some variants, for example, such guidance 2130 may be outputted locally (to a user 226 via a speaker 1171 or display 1172, 2072 aboard UAD 1005, e.g.) while UAD 1005 is stationary (tethered or hovering or landed, e.g.). Alternatively or additionally, in some variants, such task implementation modules 1131, 1132 may be disabled selectively by a signal from controller 1085 (a control signal indicating that motor 1081 is active, e.g.).

In light of teachings herein, numerous existing techniques may be applied for configuring special-purpose circuitry or other structures effective for providing navigational guidance without undue experimentation or for configuring other decisions and devices as described herein. See, e.g., U.S. Pat. No. 8,179,287 ("Method and apparatus for communicating map and route guidance information for vehicle navigation"); U.S. Pat. No. 8,170,798 ("Navigation system and operation guidance display method for use in this navigation system"); U.S. Pat. No. 8,155,805 ("Flight guidance and navigation display for a helicopter"); U.S. Pat. No. 7,970,539 ("Method of direction-guidance using 3D sound and navigation system using the method"); U.S. Pat. No. 7,899,617 ("Navigation system providing route guidance in multi-lane road according to vehicle lane position"); U.S. Pat. No. 7,881,497 ("Vision based navigation and guidance system"); U.S. Pat. No. 7,805,306 ("Voice guidance device and navigation device with the same"); U.S. Pat. No. 6,901,330 ("Navigation system, method and device with voice guidance"); U.S. Pat. No. 6,459,935 ("Integrated filter feed-thru"); U.S. Pat. No. 6,374,182 ("Method and system for providing walking instructions with route guidance in a navigation program").

Intensive operation 2513 describes transmitting navigation guidance via a speaker of the first unmanned aerial device while a primary motor of the first unmanned aerial device is not moving the first unmanned aerial device (e.g. task implementation module 1132 triggering interface control module 1111 to output navigation guidance 2130 via a speaker 1171 borne by UAD 1005 after controller 1085 disengages motor 1081 from propeller 1071). This can occur, for example, in a context in which UAD 1005 includes a secondary unit 1150 that includes one or more media 2110 and in which controller 1085 permits UAD 1005 to idle (drift or land, e.g.) by disengaging one or more primary motors 1081, 1082 thereof from one or more props 1071, 1072 to which it/they correspond (by mechanical coupling, e.g.). In some variants, for example, such task implementation modules 1131, 1132 may be enabled (so that it is possible for the transmission to coincide with the condition recited in operation 2513, e.g.) by a signal from a sensor array 1494 positioned adjacent one or more props 1071, 1072 (indicating that they are stopped, e.g.).

Intensive operation 2517 describes identifying an operating mode of the first unmanned aerial device audibly or visibly while a primary motor of the first unmanned aerial device is not moving the first unmanned aerial device (e.g. task implementation module 1133 identifying one or more triggers 2111-2120 or operating parameters 2126-2128 relating to how UAD 701 is performing or will perform a current or scheduled task 491-499 so that a person 726 who is carrying UAD 701 can hear or see such information). This can occur, for example, in a context in which speaker 1171 can announce such information audibly (in response to a voice menu aboard UAD 701, e.g.) or in which a display 1172, 2072 aboard UAD 701 can present such information visibly, or both. This can occur, for example, in a context in which the operating mode(s) that currently apply to the UAD (silent or not, flight permitted or not, e.g.) can be a function of which of the proximate zones 781, 782 currently contain UAD 701.

In light of teachings herein, numerous existing techniques may be applied for configuring special-purpose circuitry or other structures effective for reporting current or scheduled operating parameters without undue experimentation or for configuring other decisions and devices as described herein. See, e.g., U.S. Pat. No. 8,203,426 ("Feed protocol used to report status and event information in physical access control system"); U.S. Pat. No. 8,171,318 ("Reporting flash memory operating voltages"); U.S. Pat. No. 8,121,083 ("Method and device for reporting request for uplink scheduling or emergency in wireless network"); U.S. Pat. No. 8,024,138 ("Power supply circuitry, collection and reporting of power supply parameter information"); U.S. Pat. No. 8,014,974 ("System and method for analyzing and reporting machine operating parameters"); U.S. Pat. No. 7,983,759 ("Advanced patient management for reporting multiple health-related parameters"); U.S. Pat. No. 7,756,822 ("Operational reporting architecture"); U.S. Pat. No. 7,245,702 ("Method and apparatus for determining and reporting the operational status of an integrated services hub").

Extensive operation 2592 describes causing a modular observation unit to be lifted and activated within at most about an hour of the modular observation unit becoming part of the first unmanned aerial device (e.g. an interface control module 1114, motion control module 1158, device activation module 1472, and an engagement structure 2030 of UAD 1005 jointly picking up cargo module 2090 and then activating a data handling unit 2078 thereof). This can occur, for example, in a context in which engagement structure 2030 (one or more robotic arms 2039, e.g.) comprise a mechanical linkage 2040 between cargo module 2090 and the remainder of UAD 1005; in which interface control module 1114 transmits one trigger 2115 causing motion control module 1158 to engage one or more motors 1081, 1082 to rotate props 1071, 1072 so that UAD 1005 takes off; and in which interface control module 1114 transmits another trigger 2116 causing device activation module 1472 to acquire image data 1241 by activating a camera 2071 of data handling unit 2078. In some variants, for example, trigger 2116 may be configured to actuate post 2006 (sliding it along shaft 2025 rightward, as shown, into recess 2023, e.g.) so that post 2006 engages and supports a modular observation unit (a package 2050 containing a sensor array 1494, e.g.). This can occur in a context in which motion control module 1158 positions UAD 1005 so that a topmost portion of package 2050 extends up into groove 2026, for example. In other contexts, a user may (optionally) position structure 2030 (relative to package 2050, e.g.) or may otherwise facilitate linkage 2040. Alternatively or additionally, in some variants, the modular observation unit (a camera 2071 or GPS 1063 in cargo module 2090, e.g.) may be lifted (by engagement structure 2030, e.g.) responsive to an indication of the modular observation unit becoming part of the first unmanned aerial device (a control signal activating engagement structure 2030 or a sensor signal indicating an activation of engagement structure 2030, e.g.) or to the modular observation unit being activated. In some variants, moreover, the modular observation unit may be activated (by device activation module 1472, e.g.) responsive to an indication of the modular observation unit becoming part of the first unmanned aerial device (a control signal activating engagement structure 2030 or a sensor signal indicating an activation of engagement structure 2030, e.g.) or to the modular observation unit being lifted. In a context in which UAD 1005 implements UAD 501, moreover, such a user may generate one or more triggers 2111-2120 as described herein (trigger 2116 causing device activation module 1472 to acquire sensor data, e.g.) by pressing a button 561 (positioned on a cargo module 2090 of UAD 1005, e.g.).

In light of teachings herein, numerous existing techniques may be applied for configuring special-purpose circuitry or other structures effective for aerial motion control without undue experimentation or for configuring other decisions and devices as described herein. See, e.g., U.S. Pat. No. 7,962,254 ("Method and system for assisting flight control of a low-flying aircraft"); U.S. Pat. No. 7,931,238 ("Automatic velocity control system for aircraft"); U.S. Pat. No. 7,837,143 ("Method and apparatus for disabling pilot control of a hijacked aircraft"); U.S. Pat. No. 7,806,371 ("Remote control model aircraft with laser tag shooting action"); U.S. Pat. No. 7,787,998 ("Method and device for assisting the lateral control of an aircraft running on a runway"); U.S. Pat. No. 7,669,805 ("Device for remotely controlling aircraft control surfaces"); U.S. Pat. No. 7,617,024 ("Automatic heading control system for tiltrotor aircraft and helicopters"); U.S. Pat. No. 7,262,730 ("Method and a station for assisting the control of an aircraft"); U.S. Pat. No. 6,991,304 ("Method and device for automatic control of an aircraft deceleration in running phase"); U.S. Pat. No. 6,917,863 ("System for assuming and maintaining secure remote control of an aircraft").

Extensive operation 2599 describes signaling a decision whether or not to configure the first unmanned aerial device to continue observing a first person responsive to a prior observation of the first person (e.g. task implementation module 1134 responding to a behavioral indication 2102 from pattern recognition module 1422 by generating a positive or negative decision 2132 about whether to transmit a trigger 2117 instructing UAD 801 to continue one or more tasks 492, 493 that include observing person 727). This can occur, for example, in a context in which a portable article 1400 (UAD 701, e.g.) comprising secondary unit 1150 is positioned so that it can observe person 727 (sensing his speech or movements, e.g.); in which an initial task 492 comprises UAD 802 providing image data 1241 or other sensor data (comprising the prior observation, e.g.) to pattern recognition module 1422 for analysis; in which pattern recognition module 1422 comprises one or more of a gesture detection module 1402 or a spoken expression detection module 1403 or an optical condition detection module; and in which a positive behavioral indication 2102 results from one or more recognizable events 1412-1415 being detected. In some contexts, task implementation module 1134 may be configured so that decision 2132 will generally be negative (contraindicative of monitoring, e.g.) if the behavioral indication 2102 is normal (within expected bounds, e.g.), for example, and will otherwise generally be positive. In some variants, moreover, pattern recognition module 1422 may be configured to detect events (a key press input detection event 1415, e.g.) relating to person 727 from other UAD's or systems described herein (a keyboard 1391 or other input 121 of a stationary primary unit 110, e.g.). Alternatively or additionally, in some contexts, pattern recognition module 1422 may be configured to transmit a positive or negative behavioral indication 2102 resulting from some other event (a timer expiration, e.g.) occurring before any of such recognizable events (recognizable by whichever event/condition detection logic 1410 is active, e.g.) are detected.

Alternatively or additionally, task implementation module 1134 may be configured to perform operation 2599 by responding to one or more attribute indications 2101 (relating to identity, shape, preference, or other such static attributes, e.g.) of a subject of observation (an item recipient 2850 or other person described herein, e.g.). Task implementation module 1134 may thus be configured to implement a continued observation of such a subject via a "first" UAD 801 in response to any combination of (1) one or more indications 2104 that the subject's face 2865 or clothing 728 resembles that of a particular person of interest, (2) one or more indications 2105 that the subject has spoken or otherwise used particular terminology of interest (a threat or classified program name, e.g.), or (3) one or more indications 2106 that the subject has taken a recognizable action of interest (fired a gun or entered an office 1380, e.g.). Such recognizable indications 2104-2106 may be based on the "prior observations" from the "first" UAD 801, from another UAD 802, from another device, or from some combination of these. In some contexts, for example, such indications 2104-2106 from two or more such devices may be correlated or otherwise aggregated (by selective retention module 159, e.g.) according to status-indicative data (image data 1241, GPS data 1242, or timing data 1243 indicative of performance, e.g.) from each respective device.

In light of teachings herein, numerous existing techniques may be applied for configuring special-purpose circuitry or other structures effective for detecting a particular person or event without undue experimentation or for configuring other decisions and devices as described herein. See, e.g., U.S. Pat. No. 8,184,914 ("Method and system of person identification by facial image"); U.S. Pat. No. 8,170,532 ("Method and system for identification using a portable wireless communication device of a person"); U.S. Pat. No. 8,144,881 ("Audio gain control using specific-loudness-based auditory event detection"); U.S. Pat. No. 8,109,891 ("Device and method for detecting an epileptic event"); U.S. Pat. No. 8,040,245 ("Hand washing monitor for detecting the entry and identification of a person"); U.S. Pat. No. 8,036,891 ("Methods of identification using voice sound analysis"); U.S. Pat. No. 7,995,731 ("Tag interrogator and microphone array for identifying a person speaking in a room"); U.S. Pat. No. 7,774,719 ("System and method for conducting online visual identification of a person"); U.S. Pat. No. 7,653,697 ("System, method and apparatus for communicating via sound messages and personal sound identifiers"); U.S. Pat. No. 7,596,248 ("Method for identification of person by recognition of a digital fingerprint"); U.S. Pat. No. 7,596,241 ("System and method for automatic person counting and detection of specific events"); U.S. Pat. No. 7,492,926 ("Method for identifying a person from a detected eye image").

Figure 26:
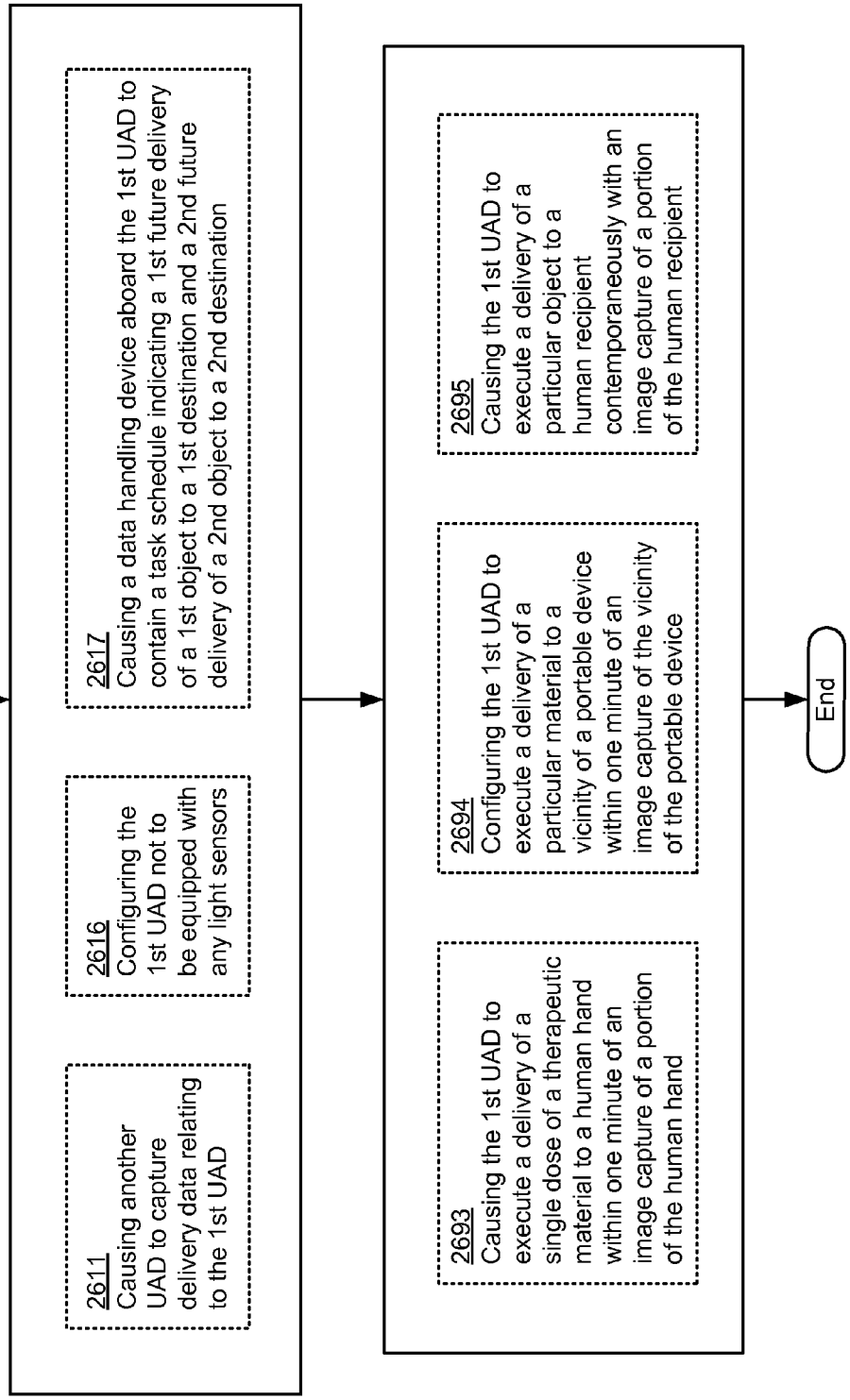

With reference now to flow 26 of FIG. 26 and to other flows 15-19, 23-25 described above, in some variants, one or more intensive operations 2611, 2616, 2617 described below may (optionally) be performed in conjunction with one or more intensive operations described above. Alternatively or additionally, one or more extensive operations 2693, 2694, 2695 described below may likewise comprise or be performed in conjunction with one or more extensive operations described above.

Intensive operation 2611 describes causing another unmanned aerial device to capture delivery data relating to the first unmanned aerial device (e.g. device activation module 1471 transmitting one or more requests 373, invitations 374, or other triggers 2284 that result in UAD 803 acquiring observations of UAD 801 completing a delivery). Referring to FIG. 8, for example, this can occur in a context in which a tracking control module 149 aboard UAD 803 receives a task description 1252 specifying what audio clips 563, photographs 553, 554 or other records may constitute acceptable delivery data 2253 and in which device activation module 1471 resides in UAD 801 (as the "first" UAD, e.g.) or in a stationary control unit 860 in wireless communication with UAD 803. Alternatively or additionally, device activation module 1471 may perform operation 2611 by configuring another UAD (an instance of UAD 1005, e.g.) to indicate an observed result 2223 (a location or other indicator of incremental success, e.g.) of one or more other tasks 491-499 (incorporating a delivery component, e.g.) being undertaken by a "first" UAD described herein.

In light of teachings herein, numerous existing techniques may be applied for configuring special-purpose circuitry or other structures effective for programmatic image capture or other event tracking without undue experimentation or for configuring other decisions and devices as described herein. See, e.g., U.S. Pat. No. 8,149,288 ("Image capture device that records image accordant with predetermined condition and storage medium that stores program"); U.S. Pat. No. 8,004,563 ("Method and system for effectively performing event detection using feature streams of image sequences"); U.S. Pat. No. 7,643,686 ("Multi-tiered image clustering by event"); U.S. Pat. No. 7,476,796 ("Image controlling apparatus capable of controlling reproduction of image data in accordance with event"); U.S. Pat. No. 6,721,640 ("Event based aircraft image and data recording system"); U.S. Pat. No. 6,167,186 ("Video recording device for retroactively reproducing a video image of an event, while also recording images in real time").

Intensive operation 2616 describes configuring the first unmanned aerial device not to be equipped with any light sensors (e.g. device configuration module 1475 transmitting a trigger 2119 that causes a robotic arm 2039 affixed to UAD 1005 to release an optical sensor aboard UAD 1005). This can occur, for example, in a context in which cargo module 2090 implements an instance of article 1400 that includes a charge-coupled device 1493 or other sensor array 1494 comprising optical sensors; in which another instance of article 1400 transmits trigger 2119 to robotic arm 2039; in which UAD 1005 implements at least one UAD 801-3 that is capable of navigating to a healthcare or item recipient 2850 or other destination 530 without any need for an onboard camera 2071 or CCD 1493; and in which a user can readily discern which cargo module 2090 (if any) is being carried by UAD 1005. In some contexts, for example, an inspection of UAD 1005 would not otherwise provide a user (recipient 2850, e.g.) with an adequate assurance of privacy.

Alternatively or additionally, operation 2616 may be performed by an instance of device configuration module 1475 that manufactures UAD 1005 (at a factory, e.g.) as a "blind" device (i.e. lacking light sensors). This can occur, for example, in a context in which "first" UAD 1005 implements UAD 801 (of FIG. 8) and in which device configuration module 1475 implements non-optical position sensing (sonar, e.g.) or optical position sensing via optical sensors not borne by UAD 1005 (in a stationary control unit 860 or aboard a second UAD 802, e.g.).

Intensive operation 2617 describes causing a data handling device aboard the first unmanned aerial device to contain a task schedule indicating a first future delivery of a first object to a first destination and a second future delivery of a second object to a second destination (e.g. task implementation module 1134 causing a memory 395 or disk drive 1495 aboard the UAD 1005 to contain several tasks 491-494, 1211-1214 comprising the first future delivery and the second future delivery). This can occur, for example, in a context in which task 491 associates (by inclusion in a single common table entry 1225, e.g.) a task identifier 1221 with one or more of a description of the "first" destination (an immediate vicinity 1371 of target 1360, e.g.) or a description of the "first" object (an inhaler 2062, e.g.) or other specifications 1223 (tracking mode, e.g.) pertaining to the first future delivery; in which task 494 associates another task identifier 1221 with one or more of a description of the "second" destination 530 or a description of the "second" object (a rescued second UAD 202, e.g.) or other specifications 1223 (aborting the delivery if anyone is present, e.g.) pertaining to the second future delivery.

In light of teachings herein, numerous existing techniques may be applied for configuring special-purpose circuitry or other structures effective for scheduling deliveries without undue experimentation or for configuring other decisions and devices as described herein. See, e.g., U.S. Pat. No. 8,090,826 ("Scheduling data delivery to manage device resources"); U.S. Pat. No. 7,929,559 ("Method of scheduling message delivery in a wireless communication system"); U.S. Pat. No. 7,516,082 ("Scheduling delivery of chemical products based on a predicted estimated time of exhaustion"); U.S. Pat. No. 7,437,305 ("Scheduling delivery of products via the internet"); U.S. Pat. No. 7,233,907 ("Parcel or service delivery with partially scheduled time windows"); U.S. Pat. No. 7,174,305 ("Method and system for scheduling online targeted content delivery"); U.S. Pat. No. 6,985,871 ("Systems and methods for scheduling reoccurring deliveries and pickups"); U.S. Pat. No. 6,826,534 ("Agent and method for dynamically scheduling publication in an automated document delivery system"); U.S. Pat. No. 6,238,290 ("System and method for scheduled delivery of a software program over a cable network"); U.S. Pat. No. 6,009,409 ("System and method for scheduling and controlling delivery of advertising in a communications network").

Extensive operation 2693 describes causing the first unmanned aerial device to execute a delivery of a single dose of a therapeutic material to a human hand within one minute of an image capture of a portion of the human hand (e.g. task implementation module 1484 causing UAD 501 to complete a delivery of a single syringe 556 directly into a hand 2864 of a healthcare recipient 2850 or caregiver). This can occur, for example in a context in which such delivery occurs within a minute before or after a camera 2836 captures one or more images (photograph 554, e.g.) depicting a palm, finger, or other feature of the hand 2864 distinctive enough to prove the delivery recipient's identity; in which such image(s) also depict the syringe 2061 or other dose clearly enough to prove the delivery occurred; in which the "first" UAD carries at most one (nominal) dose of the therapeutic material at any given time; in which the therapeutic material is highly addictive and expensive; and in which an installed dispenser or other device configured to administer more than one dose would be vulnerable to break-ins or other abuse. Alternatively, in some contexts, the only bioactive material borne by UAD 1005 (implementing UAD 501, e.g.) is the single dose 2064 in a capsule 2063.

In some embodiments, a process step occurs "within" a time interval of an event if the event occurs before or after the process step by an amount of time that does not exceed the time interval. A device or other module that is configured to perform an action "within" a time interval may include a timer 1141 or other circuitry configured to ensure such performance. In fact a module may be "configured to" perform a brief action (of 1-2 seconds, e.g.) within a long interval (of 1-2 minutes, e.g.), even if the interval is not signaled, in some contexts (in which the performance occurs during a portion of the interval in which the process step is enabled, e.g.).

In some embodiments, a device is "configured to execute" a task if special-purpose hardware or software aboard the device enables the UAD to actually complete the task. Likewise a UAD is "configured to execute" a task if such components aboard the UAD will enable the UAD to complete the task autonomously provided that no overriding instructions ("abort," e.g.) or other intervening events or conditions (blockages, e.g.) prevent such completion. A component is "aboard" a UAD if it resides in or on the UAD or is mechanically supported by the UAD (hanging from the UAD by a tether or otherwise affixed to the UAD, e.g.).

In light of teachings herein, numerous existing techniques may be applied for configuring special-purpose circuitry or other structures effective for automatic positioning without undue experimentation or for configuring other decisions and devices as described herein. See, e.g., U.S. Pat. No. 8,108,091 ("Automatic position-based guide toy vehicle apparatus"); U.S. Pat. No. 8,027,761 ("Local positioning system for automated lawn mowers"); U.S. Pat. No. 7,869,562 ("Automatic patient positioning system"); U.S. Pat. No. 7,693,565 ("Method and apparatus for automatically positioning a structure within a field of view"); U.S. Pat. No. 7,502,684 ("Method and system for the automatic piloting of an aircraft on the approach to an airdrop position"); U.S. Pat. No. 6,942,369 ("Device for the automatic adjustment of the position of the headlights on a motor vehicle"); U.S. Pat. No. 6,931,596 ("Automatic positioning of display depending upon the viewer's location").

Extensive operation 2694 describes configuring the first unmanned aerial device to execute a delivery of a particular material to a vicinity of a portable device within one minute of an image capture of the vicinity of the portable device (e.g. task implementation module 1482 responding to a photographic image 2161 depicting a position 1463 right above a cup 1464 of coffee by transmitting a trigger 2112 to one or more dispensers 2038 of UAD 1005, which respond by delivering cream or sugar into the cup 1464). This can occur, for example, in a context in which task implementation module 1482 previously transmitted a trigger 2111 commanding one or more flight control modules 151, 152 to guide UAD 1005 approximately to position 1463; in which camera 2071 comprises a cargo module 2090 carried by a robotic arm 2039 or other support structure 2030 of UAD 1005; and in which camera 2071 captures a video clip 2153 comprising a succession of images 2161, 2162 depicting a top view of cup 1464 via which an optical condition detection module 1404 may effectively control the alignment of the one or more dispensers 2038 relative to cup 1464. In some contexts, for example, other preparations (verifying a user preference, e.g.) may occur before the delivery is completed (during the "one minute," e.g.). Alternatively or additionally, in some variants, such an image 2161 (suitable for verifying alignment, e.g.) may be obtained via a charge-coupled device 1493 (aboard UAD 1005 or another UAD tasked with observation, e.g.) or via a stationary-mount surveillance camera 936 (mounted on a building 935 or other stationary object, e.g.).

In light of teachings herein, numerous existing techniques may be applied for configuring special-purpose circuitry or other structures effective for delivering an item to a vicinity of a device without undue experimentation or for configuring other decisions and devices as described herein. See, e.g., U.S. Pat. No. 8,167,786 ("Systems and methods for delivering a medical implant to an anatomical location in a patient"); U.S. Pat. No. 7,822,463 ("Method for delivering a device to a target location"); U.S. Pat. No. 7,735,631 ("Mail processing system and method of delivering articles to delivery locations therein"); U.S. Pat. No. 7,670,329 ("Systems and methods for delivering drugs to selected locations within the body"); U.S. Pat. No. 7,658,156 ("Apparatus and method for delivering beneficial agents to subterranean locations"); U.S. Pat. No. 7,361,183 ("Locator and delivery device and method of use"); U.S. Pat. No. 6,711,555 ("Method and apparatus for delivering mail items to non-postal route locations").

Extensive operation 2695 describes causing the first unmanned aerial device to execute a delivery of a particular object to a human recipient contemporaneously with an image capture of a portion of the human recipient (e.g. task implementation module 1483 transmitting one or more triggers 2110, 2116 that configure UAD 1005 to deliver the object to recipient 2850 within about ten seconds of when a camera 2071, 2836 captures an image 2164 of a hand 2864 or face 2865 of the recipient 2850). This can occur, for example, in a context in which the object comprises a passive radio frequency identification (RFID) chip 1461, an envelope 551 or other package 2050 (containing an inhaler 2062 or other therapeutic product 2060, e.g.), a data handling unit 2078 (a memory 395 or other medium, e.g.), a battery 2085 or other power source, a wearable article (earpiece 2861 or wristband 2863, e.g.), a "second" UAD, or similar physical objects. In some variants, for example, such image capture occurs in response to one or more triggers from task implementation module 1483.

In light of teachings herein, numerous existing techniques may be applied for configuring special-purpose circuitry or other structures effective for determining how one or more portions of a person's body are positioned without undue experimentation or for configuring other decisions and devices as described herein. See, e.g., U.S. Pat. No. 7,978,084 ("Body position monitoring system"); U.S. Pat. No. 7,949,089 ("Apparatus and method for tracking feature's position in human body"); U.S. Pat. No. 7,934,267 ("Articles of apparel providing enhanced body position feedback"); U.S. Pat. No. 7,916,066 ("Method and apparatus for a body position monitor and fall detector using radar"); U.S. Pat. No. 7,889,913 ("Automatic compositing of 3D objects in a still frame or series of frames"); U.S. Pat. No. 7,630,806 ("System and method for detecting and protecting pedestrians"); U.S. Pat. No. 7,029,031 ("Method and device for detecting the position and the posture of a human body"); U.S. Pat. No. 6,692,449 ("Methods and system for assessing limb position sense during movement").

Figure 27:
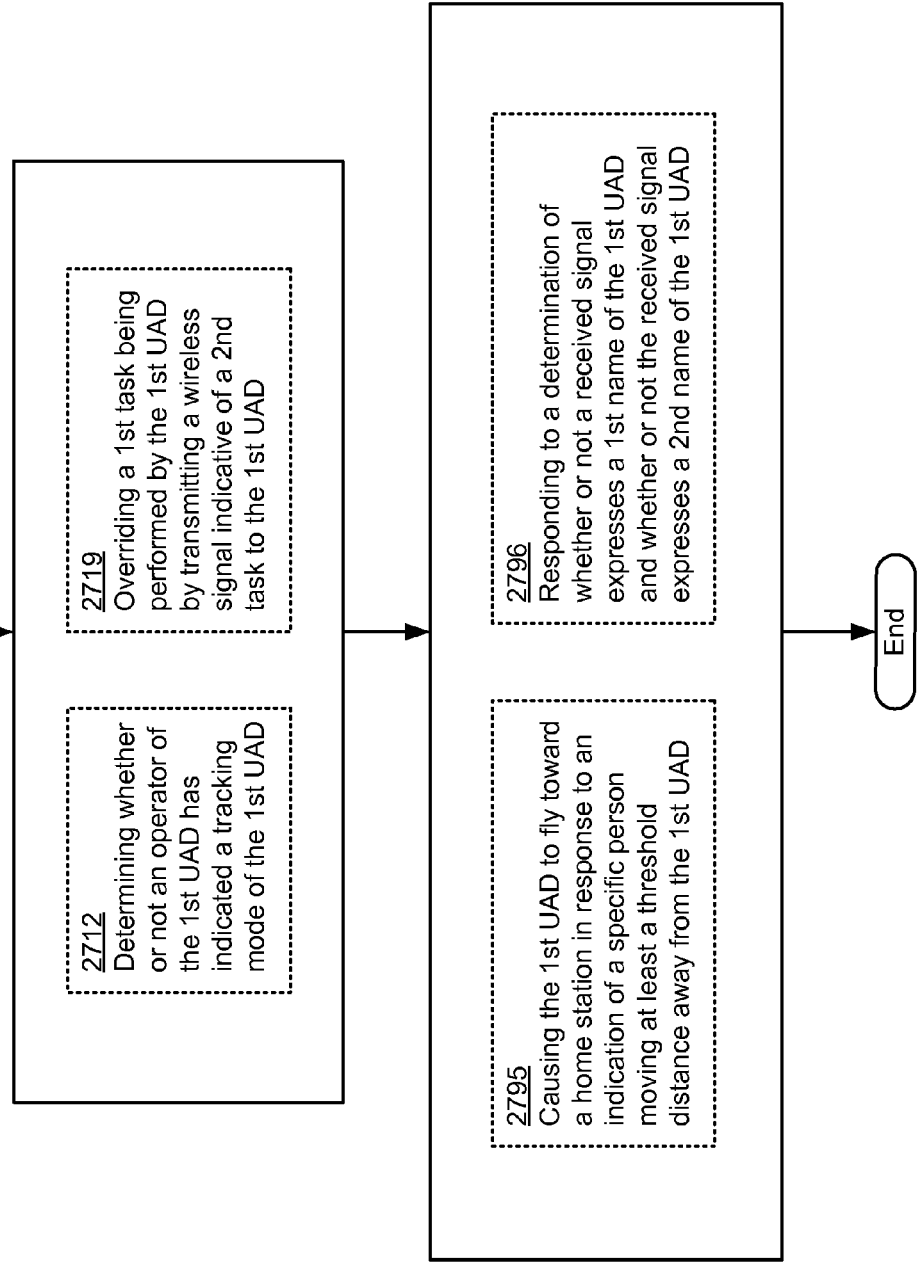

With reference now to flow 27 of FIG. 27 and to other flows 15-19, 23-26 described above, in some variants, one or more intensive operations 2712, 2719 described below may (optionally) be performed in conjunction with one or more intensive operations described above. Alternatively or additionally, one or more extensive operations 2795, 2796 described below may likewise comprise or be performed in conjunction with one or more extensive operations described above.

Intensive operation 2712 describes determining whether or not an operator of the first unmanned aerial device has indicated a tracking mode of the first unmanned aerial device (e.g. interface control module 1110 determining whether any specifications 1223 provided by a user 226 of UAD 1005 contain any indication 2109 of whether or how any ongoing or future task 491-499, 1211-1214 assigned to UAD 1005 should be tracked). This can occur, for example, in a context in which user 226 indicates via input 391 (a mouse or keyboard 1391, e.g.) a decision 2131 that a default tracking mode 361 for UAD 1005 (for use in tasks not specifying an exception, e.g.) should be "none" (not record any aspect of tasks performed by UAD 1005, e.g.). Alternatively or additionally, such decisions 2131 or specifications 1223 may indicate "periodic" tracking (recording image data 1241, GPS data 1242, wind speed, or other status-indicative data 1240 relating to UAD 1005 periodically, e.g.) with operating parameter 2127 specifying the tracking period (how long to wait between successive recording events, e.g.) and operating parameter 2128 specifying the source of data to be recorded (event/condition detection logic 1410 or camera 2071, e.g.).

In light of teachings herein, numerous existing techniques may be applied for configuring special-purpose circuitry or other structures effective for task performance monitoring without undue experimentation or for configuring other decisions and devices as described herein. See, e.g., U.S. Pat. No.

8,171,474 ("System and method for managing, scheduling, controlling and monitoring execution of jobs by a job scheduler utilizing a publish/subscription interface"); U.S. Pat. No. 8,164,461 ("Monitoring task performance"); U.S. Pat. No. 7,996,658 ("Processor system and method for monitoring performance of a selected task among a plurality of tasks"); U.S. Pat. No. 7,953,806 ("Task assignment and progress monitoring in an instant messaging session"); U.S. Pat. No. 7,784,946 ("Virtual microscope system for monitoring the progress of corneal ablative surgery and associated methods"); U.S. Pat. No. 7,764,179 ("Method of an apparatus for monitoring the processing cycle of a job and instructing workers to perform events or steps according to a standard"); U.S. Pat. No. 7,610,213 ("Apparatus and method for monitoring progress of customer generated trouble tickets"); U.S. Pat. No. 7,494,464 ("Monitoring system for monitoring the progress of neurological diseases"); U.S. Pat. No. 7,331,019 ("System and method for real-time configurable monitoring and management of task performance systems"); U.S. Pat. No. 6,669,653 ("Method and apparatus for monitoring the progress of labor"); U.S. Pat. No. 6,569,690 ("Monitoring system for determining progress in a fabrication activity"); U.S. Pat. No. 6,034,361 ("System for monitoring the progress of a chemical reaction in a microwave-assisted heating system"); U.S. Pat. No. 6,033,316 ("Golf course progress monitor to alleviate slow play").

Intensive operation 2719 describes overriding a first task being performed by the first unmanned aerial device by transmitting a wireless signal indicative of a second task to the first unmanned aerial device (e.g. task implementation module 1139 transmitting a wireless signal 2192 indicative of a pickup task 1213 and a delivery task 1214 to an interface control module 142 of a UAD 1005 that is performing a lower-priority task 1211). This can occur, for example, in a context in which interface control module 142 includes a task scheduler 1220 indicating one or more ongoing, contingent, upcoming, or other tasks 1211-1214; in which task scheduler 1220 earlier received (from one or more task implementation modules 1130-1139, e.g.) another signal 2191 indicative of the lower-priority task 1211; and in which scalar values 1222 control the respective rankings of the scheduled tasks 1211-1214 so that an intermediate-priority task 1212 (energy replenishment, e.g.) will be performed before "lower-priority" tasks and after "higher-priority" tasks. In other variants, however, task implementation module 1139 may be (a) configured to modify the scalar value 1222 of task 1212 (to indicate a higher priority, e.g.) responsive to an indication that one or more higher priority tasks 1213, 1214 will not be completed (due to capacity limitations, e.g.) without first executing task 1212 or (b) configured to be performed contingently (with a highest priority, but only if a particular condition (running below a fuel/charge threshold 2294 or other such conditions set forth in the task specification 1223, e.g.) is met.

In light of teachings herein, numerous existing techniques may be applied for configuring special-purpose circuitry or other structures effective for ranking tasks without undue experimentation or for configuring other decisions and devices as described herein. See, e.g., U.S. Pat. No. 8,200,491 ("Method and system for automatically detecting morphemes in a task classification system using lattices"); U.S. Pat. No. 8,185,536 ("Rank-order service providers based on desired service properties"); U.S. Pat. No. 8,135,708 ("Relevance ranked faceted metadata search engine"); U.S. Pat. No. 8,095,612 ("Ranking messages in an electronic messaging environment"); U.S. Pat. No. 8,087,019 ("Systems and methods for performing machine-implemented tasks"); U.S. Pat. No. 7,969,922 ("Apparatus and methods for providing configurable task management of a wireless device"); U.S. Pat. No. 7,945,470 ("Facilitating performance of submitted tasks by mobile task performers"); U.S. Pat. No. 7,885,222 ("Task scheduler responsive to connectivity prerequisites"); U.S. Pat. No. 8,127,300 ("Hardware based dynamic load balancing of message passing interface tasks"); U.S. Pat. No. 7,290,005 ("System for improving the performance of information retrieval-type tasks by identifying the relations of constituents").

Extensive operation 2795 describes causing the first unmanned aerial device to fly toward a home station in response to an indication of a specific person moving at least a threshold distance away from the first unmanned aerial device (e.g. sequence recognition module 1106 transmitting a trigger 423 to a controller 1085, 1095 of the "first" UAD instructing the latter to fly home in response to an outcome of protocol 418 indicating that one or more device-identifiable people 725 have moved at least a minimum distance 2174 in a direction generally away from the 1st UAD). This can occur, for example, in a context in which (at least) the navigation of UAD 1005 is locally controlled (via on-board controller 1085, e.g.); in which controller 1085 has access to protocol 418 (implemented therein as a software subroutine or in special-purpose circuitry, e.g.); in which the "first" UAD comprises a helicopter 1002 or other UAD 1005 of FIG. 10 (featuring one or more aspects of UAD's depicted above in systems 4-9, e.g.); and in which one or more kiosks 250 or other stations 520, 930 are qualifying "home stations" (identified by coordinates 606, a distinctive auditory or optical signal from a beacon 217 near such station(s), or other such expressions 2122 (in trigger 423, e.g.) useable by a flight control module 151, 152.

In one context, sequence recognition module 1106 (implementing one embodiment of protocol 418, e.g.) has been notified that entity identification module 144 has detected person 725 being "near" the first UAD—close enough that facial recognition, proximity sensors 449, or other suitable technologies described herein generate an output 1142 identifying person 725 as the "specific person" and explicitly or otherwise indicating a distance 2171 and direction 2186 of initial separation (in a 2- or 3-dimensional frame of reference, e.g.). Sequence recognition module 1106 responds to this notification by iteratively determining (each 0.1 or 1 second, e.g.) where person 725 is relative to her prior position (indicating her movement distance 2172 and direction 2187, e.g.) and by accumulating the movements (as vector-valued or scalar-valued components, e.g.) and comparing a resultant vector magnitude or other scalar distance 2173 (for at least those iterations in which person 725 moved generally away from the first UAD, e.g.) against the threshold distance 2174. (It should be noted that device 775 would be moving "generally away" from another UAD 701, situated directly to the south as shown, by moving west-northwest or north or east-northeast.) In some contexts, sequence recognition module 1106 may be configured to transmit a heading or otherwise-expressed direction 2188 (comprising trigger 423, e.g.) generally toward a (nearest or other) home station 520 relative to UAD 701's current location, whereby UAD 701 is caused to fly toward home station 520.

Alternatively or additionally, protocol 418 (implemented in a sequence recognition module 1107 within a controller 1095 remote from a "first" UAD 1005 under its control, e.g.) may make a similar determination of a UAD user 226, 626 (either being the "specific person") moving at least a threshold distance 2175 (of roughly 1 to 10 meters, within 1 or 2 orders of magnitude, e.g.) away from the first UAD as a manifestation of such user(s) being finished with or otherwise not in need of the first UAD. This can occur, for example, in a context in which "first" UAD 1005 has landed or started hovering in a locality in response to sequence recognition module 1107 receiving an indication of such user(s) being near the first UAD (from entity identification module 144 or proximity sensor 449, e.g.).

In light of teachings herein, numerous existing techniques may be applied for configuring special-purpose circuitry or other structures effective for estimating a distance or movement (of one person or object relative to another, e.g.) without undue experimentation or for configuring other decisions and devices as described herein. See, e.g., U.S. Pat. No. 7,782,365 ("Enhanced video/still image correlation"); U.S. Pat. No. 8,219,312 ("Determining speed parameters in a geographic area"); U.S. Pat. No. 8,219,116 ("Wireless base station location estimation"); U.S. Pat. No. 8,207,869 ("Position estimation for navigation devices"); U.S. Pat. No. 8,138,976 ("Method for position estimation using generalized error distributions"); U.S. Pat. No. 7,592,945 ("Method of estimating target elevation utilizing radar data fusion"); U.S. Pat. No. 7,532,896 ("Wireless node location mechanism using antenna pattern diversity to enhance accuracy of location estimates"); U.S. Pat. No. 8,068,802 ("Estimating the location of a wireless terminal based on calibrated signal-strength measurements"); U.S. Pat. No. 7,895,013 ("Estimation of the speed of a mobile device"); U.S. Pat. No. 7,720,554 ("Methods and apparatus for position estimation using reflected light sources").

Extensive operation 2796 describes responding to a determination of whether or not a received signal expresses a first name of the first unmanned aerial device and whether or not the received signal expresses a second name of the first unmanned aerial device (e.g. pattern recognition module 1423 transmitting respective results 2224, 2225 of searching a sequence 2121 of characters of an incoming signal 2194 for any instance of the "first" UAD name 1425 or any instance of the "second" UAD name 1426). This can occur, for example, in a context in which such results 2224, 2225 are each Boolean values ("positive" if found and otherwise "negative," e.g.); in which such names 1425, 1426 are aliases 822, 823 identifying UAD 802; in which control unit 860 includes storage or transmission media 2100, 2200; and in which instances of article 1400 comprise control unit 860 and reside in network 890. Alternatively or additionally, in some variants, pattern recognition module 1423 may respond to a positive search/comparison result (an indication that at least one of the UAD names was found among in signal 2194, e.g.) by programmatically and conditionally invoking one or more device activation modules 1471, 1472 or causing a transmission of one or more triggers 2111-2120 described herein.

In light of teachings herein, numerous existing techniques may be applied for configuring special-purpose circuitry or other structures effective for pattern matching without undue experimentation or for configuring other decisions and devices as described herein. See, e.g., U.S. Pat. No. 8,209,278 ("Computer editing system for common textual patterns in legal documents"); U.S. Pat. No. 8,209,171 ("Methods and apparatus relating to searching of spoken audio data"); U.S. Pat. No. 8,171,567 ("Authentication method and system"); U.S. Pat. No. 8,023,695 ("Methods for analyzing electronic media including video and audio"); U.S. Pat. No. 7,917,514 ("Visual and multi-dimensional search"); U.S. Pat. No. 8,131,540 ("Method and system for extending keyword searching to syntactically and semantically annotated data").

Referring again to the flow embodiments of FIGS. 15 and 23-27, other variants of data acquisition module 138 may perform operation 53—obtaining first data indicating that a first unmanned aerial device delivered a first item to a first entity—by asking for, receiving, and recording (via an interface 390 or other data handling unit 2078 in a vicinity 2855 of an item recipient 2850, e.g.) a spoken confirmation 382 that the item was received. This can occur, for example, in a context in which UAD 1005 includes data handling unit 207; in which an engagement structure 2030 of UAD 1005 (post 2006 or robotic arm 2039, e.g.) releases cargo module 490 (a cell phone, e.g.) in a vicinity 2855 of recipient 2850; and in which data acquisition module 138 triggers the data handling unit 2078 to ask for and cause a recordation of a spoken confirmation 382 (as audio clip 563, for example, obtained by conducting an automated telephone call or similar verbal interchange via data handling unit 2078, e.g.) from recipient 2850. In the variants set forth above, for example, operation 53 and one or more others of the above-describe intensive operations may be initiated by processor 365 (executing a respective variant of high-level command 484, e.g.) or by invoking special-purpose circuitry as described above.

Other variants of data delivery module 153 may likewise perform operation 84 of flow 15—transmitting via a free space medium the first data to a provider of the first item as an automatic and conditional response to the first data indicating that the first unmanned aerial device delivered the first item to the first entity, the first data indicating at least one of the first item or the first entity or the first unmanned aerial device—by transmitting (to a sender 510 of cargo module 490, e.g.) a wireless signal 2195 (via station 520 through air 585, e.g.) containing the recorded spoken confirmation 382 or other data indicating the delivery within a few minutes after data acquisition module 138 obtains such confirmation. This can occur, for example, in a context in which one or more systems 5-9 described above implement primary unit 110, in which UAD 1005 implements the "first" UAD, and in which sender 510 would otherwise be unwilling to send cargo module 490 via UAD 1005. In the variants set forth above, for example, operation 84 and one or more others of the above-describe extensive operations may be initiated by processor 365 (executing a respective variant of high-level command 485, e.g.) or by invoking special-purpose circuitry as described above.

Referring again to the flow variants of FIGS. 16 and 23-27, other variants of coordinate communication module 136 may perform operation 51—obtaining first position data from a first entity, by a second entity, the first entity being a first unmanned aerial device—by receiving an address 562 from UAD 501 indicating the position of sender 510). This can occur, for example, in a context in which UAD 501 implements UAD 1005 as described above; in which sender 510 is or has the "first" resource (a data handling unit 2078 or other package 2050 or product 2060 described herein, e.g.); and in which such resource(s) may be allocated as described herein (purchased or temporarily reserved by the "second" entity, e.g.). This can occur, for example, in a context in which the second entity (recipient 2850, e.g.) is remote from the location specified by the first position data (not within the same room or facility, e.g.). In the variants set forth above, for example, operation 51 and one or more others of the above-describe intensive operations may be initiated by processor 365 (executing a respective variant of high-level command 484, e.g.) or by invoking special-purpose circuitry as described above.

Other variants of resource reservation module 156 may likewise perform operation 83 of flow 16—signaling a decision whether or not to allocate a first resource to the second entity after the first position data passes from the first unmanned aerial device to the second entity, the first resource being associated with the first position data—by transmitting an indication 2107 that a request 373 for such a resource reservation 376 has been declined. This can occur in a context in which the first resource is offline or otherwise unavailable, for example, or in which no device is authorized to grant a reservation of the first resource. In some contexts, for example, resource reservation module 156 may be configured to manage other resources within a defined zone 781 or of a particular type (products 2060, e.g.). Alternatively or additionally, in some variants, resource reservation module 156 may be configured to provide (automatically and conditionally, e.g.) one or more signals other than whether or not to allocate the first resource ("stand by while I contact an authorized agent for you," e.g.). In the variants set forth above, for example, operation 83 and one or more others of the above-describe extensive operations may be initiated by processor 365 (executing a respective variant of high-level command 485, e.g.) or by invoking special-purpose circuitry as described above.

In light of teachings herein, numerous existing techniques may be applied for configuring special-purpose circuitry or other structures effective for associating a user or a device with another user or another device without undue experimentation or for configuring other decisions and devices as described herein. See, e.g., U.S. Pat. No. 8,023,485 ("Method, system and device for realizing user identity association"); U.S. Pat. No. 7,979,585 ("System and method to associate a private user identity with a public user identity"); U.S. Pat. No. 7,970,660 ("Identifying associations between items and email-address-based user communities"); U.S. Pat. No. 7,941,505 ("System and method for associating a user with a user profile in a computer network environment"); U.S. Pat. No. 7,894,812 ("Automatic over-the-air updating of a preferred roaming list (PRL) in a multi-mode device, based on an account association between the device and a wireless local area network (WLAN) access point"); U.S. Pat. No. 7,743,099 ("Associating multiple visibility profiles with a user of real-time communication system"); U.S. Pat. No. 7,716,378 ("System and method to associate a private user identity with a public user identity"); U.S. Pat. No. 7,703,691 ("Multiple device and/or user association"); U.S. Pat. No. 7,627,577 ("System and method for maintaining an association between a distribution device and a shared end user characteristic"); U.S. Pat. No. 6,473,824 ("Dynamic association of input/output device with application programs").

Referring again to the flow variants of FIGS. 17 and 23-27, other variants of interface control module 141 may perform operation 52—causing a first unmanned aerial device to guide a first individual to a first destination—by signaling via UAD 1005 a direction 2189 of one or more waypoints 642, 742 relative to a current position of the "first" individual along a path to the first destination. In the context of FIG. 6, for example, an interface control module 141 may be configured to perform operation 52 by prompting UAD 601 (implementing UAD 1005, e.g.) to signal (via a wireless communication linkage 694, e.g.) a direction of a waypoint 642 to guide a driver (by causing user interface 660 to display an upward arrow to user 626, e.g.) along a path 643 to the first destination (parking space 648, e.g.). Another implementation of interface control module 141 may be configured to perform operation 52 by configuring UAD 701 (implementing UAD 1005, e.g.) to signal a direction of a waypoint 742 to guide a pedestrian (via a speaker 1171 or display 1172 aboard UAD 1005, e.g.) along a path 743 (to "first" destination 530, e.g.). In relation to these variants and others set forth above, operation 52 and one or more others of the above-describe intensive operations may (optionally) be initiated by processor 365 (executing a respective variant of high-level command 484, e.g.) or by invoking special-purpose circuitry as described above.

Other variants of flight control module 152 may likewise perform operation 85 of flow 17—causing the first unmanned aerial device to fly to a second destination as an automatic and conditional response to an indication of the first individual arriving at the first destination—by causing UAD 1005 to fly to the "second" destination after, and responsive to, the "first" individual apparently arriving at a parking space 648 or other "first" destination 530). This can occur, for example, in a context in which the "second" destination relates to a task 491-499 to be performed next; in which one or more other conditions, events, or indications 2101-2109 described herein also occur (detected by event/condition detection logic 1410 or signaled by one or more triggers 2111-2120, e.g.); and in which flight control module 152 implements such flight by triggering a task implementation module 1485 aboard UAD 1005 to activate one or more motors 1081-1083 aboard UAD 1005 controlling one or more props 1071-1073 aboard UAD 1005. In the variants set forth above, for example, operation 85 and one or more others of the above-describe extensive operations may be initiated by processor 365 (executing a respective variant of high-level command 485, e.g.) or by invoking special-purpose circuitry as described above.

Referring again to the flow variants of FIGS. 18 and 23-27, other variants of enlistment module 133 may perform operation 54—indicating a first unmanned aerial device participating in a first task—by notifying device operators (e.g. users 226, 626) or other persons 725, 726 that a "first" task 491-499 (or component task thereof) as described herein has been begun by or accepted on behalf of "first" UAD 1005. This can occur, for example, in a context in which network 190 contains UAD 1005 and in which primary unit 110 contains interface device 310 and event/condition detection unit 400. In the variants set forth above, for example, operation 54 and one or more others of the above-describe intensive operations may be initiated by processor 365 (executing a respective variant of high-level command 484, e.g.) or by invoking special-purpose circuitry as described above.

Other variants of control unit 860 may likewise perform operation 82 of flow 18—signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device—by configuring a name recognition module 147 of control unit 860 to recognize and use the primary identifier 821 of UAD 1005 (instead of an alias, e.g.) partly based on an indication of UAD 1005 participating in a "first" task 491-499 described herein and partly based on an indication that UAD 1005 has not accepted any aliases 822, 823. This can occur, for example, in a context in which the decision is negative (not to cause UAD 1005 to recognize any aliases, e.g.); in which control unit 860 makes the negative decision in response to UAD 1005 not responding to a configuration request within a prescribed interval; in which UAD 1005 implements UAD 802; in which control unit 860 implements primary unit 110; and in which control unit 860 addresses UAD 1005 during such task(s) using primary identifier 821. Alternatively, in some contexts, UAD 1005 may generate such a negative decision. In the variants set forth above, for example, operation 82 and one or more others of the above-describe extensive operations may be initiated by processor 365 (executing a respective variant of high-level command 485, e.g.) or by invoking special-purpose circuitry as described above.

Referring again to the flow variants of FIGS. 19 and 23-27, other variants of tracking control module 977 may perform operation 55—obtaining a tracking mode of a delivery task of a first unmanned aerial device—by receiving a device-executable command sequence 2125 implementing a user-defined mode 363 of tracking one or more delivery tasks 491, 494 performed or being performed by UAD 1005. This can occur, for example, in a context in which UAD 1005 implements interface device 310 and media 1200, 2100; in which processor 365 executes device-executable command sequence 2125 (e.g. capturing one or more of image data 1241, GPS data 1242, or timing data 1243) periodically or in response to a trigger 2111-2120 described herein. Alternatively or additionally, a one or more user-specified expressions 2122 (expressing rules that incorporate OR, AND, or other logical operators, e.g.) may identify one or more device-detectable indications 2101-2109 that enable or disable such tracking (respectively as a prerequisite or exception, e.g.). In the variants set forth above, for example, operation 55 and one or more others of the above-describe intensive operations may be initiated by processor 365 (executing a respective variant of high-level command 484, e.g.) or by invoking special-purpose circuitry as described above.

Other variants of selective retention module 158 may likewise perform operation 81 of flow 19—signaling a decision whether or not to omit a record of the first unmanned aerial device completing the delivery task of the first unmanned aerial device as an automatic and conditional response to the tracking mode of the delivery task of the first unmanned aerial device—by transmitting a selection of records 961-964 that are recognized by one or more gesture detection modules 1402, spoken expression detection modules 1403, optical condition detection modules 1404, or other pattern recognition modules 1421-1423 configured to detect one or more events 1412-1414 (a gesture or word or other expression of acknowledgment from a delivery recipient 2850, e.g.) specified by the tracking mode (and detectable as visual or auditory phenomena in one or more records 961-964, e.g.). This can occur, for example, in a context in which a sender 510 of an item delivered decides to specify what kind(s) of expression (saying "take my picture," e.g.) should trigger tracking; in which the sender 510 expresses such decision(s) as the tracking mode 982; and in which the first UAD 1005 would not otherwise perform any tracking upon completion of one or more delivery tasks 491, 494. In the variants set forth above, for example, operation 81 and one or more others of the above-describe extensive operations may be initiated by processor 365 (executing a respective variant of high-level command 485, e.g.) or by invoking special-purpose circuitry as described above.

Referring again to flows 15-19 and to variants thereof described with reference to FIGS. 23-27, in some implementations, each of these flows may (optionally) be performed entirely within a "first" unmanned aerial device (in UAD 1005, e.g.) or within another device described herein. In some implementations, for example, each of these flows may be performed entirely within a vehicle as described herein (car 602, e.g.) or within a single handheld device (e.g. a cell phone or handheld UAD 202, 701) or in a wearable article (an earpiece 2861, wristband 2863, or similar chip-containing device, for example, or an article of clothing 728 having such a device affixed thereto). Alternatively or additionally, the first unmanned aerial device may include the second aerial device (as a cargo module 2090 thereof, e.g.). In some embodiments, moreover, each of these flows may be performed by a network 1090 of devices or otherwise shared among two or more such devices 1010.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim 1ncludes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

With respect to the numbered clauses and claims expressed below, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise. Also in the numbered clauses below, specific combinations of aspects and embodiments are articulated in a shorthand form such that (1) according to respective embodiments, for each instance in which a "component" or other such identifiers appear to be introduced (with "a" or "an," e.g.) more than once in a given chain of clauses, such designations may either identify the same entity or distinct entities; and (2) what might be called "dependent" clauses below may or may not incorporate, in respective embodiments, the features of "independent" clauses to which they refer or other features described above.

Clauses

1. A system comprising:
one or more articles of manufacture including
circuitry for indicating a first unmanned aerial device participating in a first task; and
circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device.

2. The system of any of the above SYSTEM CLAUSES in which the circuitry for indicating a first unmanned aerial device participating in a first task comprises:
circuitry for configuring the first unmanned aerial device to perform a first observation of a particular task in a first zone and a second unmanned aerial device to perform a second observation of the particular task in a second zone, the particular task being the first task.

3. The system of any of the above SYSTEM CLAUSES in which the circuitry for indicating a first unmanned aerial device participating in a first task comprises:
circuitry for configuring the first unmanned aerial device to perform a first observation of a particular task in a first zone and a second unmanned aerial device to perform a second observation of the particular task in a second zone, the particular task being the first task, the first zone and the second zone sharing a common boundary.

4. The system of any of the above SYSTEM CLAUSES in which the circuitry for indicating a first unmanned aerial device participating in a first task comprises:
circuitry for configuring the first unmanned aerial device to capture normalcy-indicative data relating to a human subject as a component of the first task.

5. The system of any of the above SYSTEM CLAUSES in which the circuitry for indicating a first unmanned aerial device participating in a first task comprises:
circuitry for configuring the first unmanned aerial device to capture normalcy-indicative data relating to a human subject as a component of the first task, at least some of the normalcy-indicative data being negatively indicative of normalcy.

6. The system of any of the above SYSTEM CLAUSES in which the circuitry for indicating a first unmanned aerial device participating in a first task comprises:
circuitry for configuring the first unmanned aerial device to capture normalcy-indicative data relating to a human subject as a component of the first task, at least some of the normalcy-indicative data being indicative of a biometric, the biometric being an abnormal or normal rate, the abnormal or normal rate being a respiration rate or a heart rate of the human subject.

7. The system of any of the above SYSTEM CLAUSES in which the circuitry for indicating a first unmanned aerial device participating in a first task comprises:
circuitry for configuring the first unmanned aerial device to capture normalcy-indicative data relating to a human subject as a component of the first task, at least some of the normalcy-indicative data being indicative of a speech rate or a movement rate of the human subject.

8. The system of any of the above SYSTEM CLAUSES in which the circuitry for indicating a first unmanned aerial device participating in a first task comprises:
circuitry for causing the first unmanned aerial device to undertake a performance observation task of a job that includes a performance task and the performance observation task, the performance observation task being the first task.

9. The system of any of the above SYSTEM CLAUSES in which the circuitry for indicating a first unmanned aerial device participating in a first task comprises:
circuitry for transmitting a wireless signal indicative of a delivery of a package to a device associated with a recipient of the package, the wireless signal indicating at least one of the first unmanned aerial device or the package or a sender of the package, the first task including the delivery of the package to the recipient of the package.

10. The system of any of the above SYSTEM CLAUSES in which the circuitry for indicating a first unmanned aerial device participating in a first task comprises:
circuitry for presenting navigation guidance via a display aboard the first unmanned aerial device while a primary motor of the first unmanned aerial device is not moving the first unmanned aerial device.

11. The system of any of the above SYSTEM CLAUSES in which the circuitry for indicating a first unmanned aerial device participating in a first task comprises:
circuitry for transmitting navigation guidance via a speaker of the first unmanned aerial device while a primary motor of the first unmanned aerial device is not moving the first unmanned aerial device.

12. The system of any of the above SYSTEM CLAUSES in which the circuitry for indicating a first unmanned aerial device participating in a first task comprises:

circuitry for identifying an operating mode of the first unmanned aerial device audibly or visibly while a primary motor of the first unmanned aerial device is not moving the first unmanned aerial device.

13. The system of any of the above SYSTEM CLAUSES in which the circuitry for indicating a first unmanned aerial device participating in a first task comprises:

circuitry for causing another unmanned aerial device to capture delivery data relating to the first unmanned aerial device.

14. The system of any of the above SYSTEM CLAUSES in which the circuitry for indicating a first unmanned aerial device participating in a first task comprises:

circuitry for causing another unmanned aerial device to capture delivery data relating to the first unmanned aerial device, the delivery data relating to the first unmanned aerial device depicting at least one of the first unmanned aerial device or a vicinity of the first unmanned aerial device.

15. The system of any of the above SYSTEM CLAUSES in which the circuitry for indicating a first unmanned aerial device participating in a first task comprises:

circuitry for configuring the first unmanned aerial device not to be equipped with any light sensors.

16. The system of any of the above SYSTEM CLAUSES in which the circuitry for indicating a first unmanned aerial device participating in a first task comprises:

circuitry for configuring the first unmanned aerial device not to be equipped with any light sensors, the circuitry for configuring the first unmanned aerial device not to be equipped with any light sensors being operably coupled with a releasable mechanical linkage, the releasable mechanical linkage being configured to support a data handling unit, the data handling unit including at least one light sensor.

17. The system of any of the above SYSTEM CLAUSES in which the circuitry for indicating a first unmanned aerial device participating in a first task comprises:

circuitry for causing a data handling device aboard the first unmanned aerial device to contain a task schedule indicating a first future delivery of a first object to a first destination and a second future delivery of a second object to a second destination.

18. The system of any of the above SYSTEM CLAUSES in which the circuitry for indicating a first unmanned aerial device participating in a first task comprises:

circuitry for causing a data handling device aboard the first unmanned aerial device to contain a task schedule indicating a first future delivery of a first object to a first destination and a second future delivery of a second object to a second destination, the data handling device aboard the first unmanned aerial device comprising at least one of a disk drive or a volatile memory.

19. The system of any of the above SYSTEM CLAUSES in which the circuitry for indicating a first unmanned aerial device participating in a first task comprises:

circuitry for determining whether or not an operator of the first unmanned aerial device has indicated a tracking mode of the first unmanned aerial device.

20. The system of any of the above SYSTEM CLAUSES in which the circuitry for indicating a first unmanned aerial device participating in a first task comprises:

circuitry for overriding a second task being performed by the first unmanned aerial device by transmitting a wireless signal indicative of the first task to the first unmanned aerial device.

21. The system of any of the above SYSTEM CLAUSES in which the one or more articles of manufacture further comprise:

circuitry for configuring the first unmanned aerial device to transmit a wireless signal indicative of having performed a particular task and not to store any indication of having performed the particular task, the particular task being the first task.

22. The system of any of the above SYSTEM CLAUSES in which the one or more articles of manufacture further comprise:

the first unmanned aerial device, including circuitry for signaling a decision whether or not to reserve a space for a passenger vehicle.

23. The system of any of the above SYSTEM CLAUSES in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

circuitry for signaling a decision whether or not to reserve a specific resource by associating the specific resource with the first unmanned aerial device or with a specific person.

24. The system of any of the above SYSTEM CLAUSES in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

circuitry for signaling a decision whether or not to reserve a specific resource by associating the specific resource with the first unmanned aerial device or with a specific person, the decision being an affirmative decision to reserve the specific resource, the specific resource including at least one of a space or a material.

25. The system of any of the above SYSTEM CLAUSES in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

circuitry for responding to an indication of the first unmanned aerial device becoming within a proximity of a mobile device by signaling the decision whether or not to cause the first unmanned aerial device to recognize the alias identifying the first unmanned aerial device as the automatic and conditional response to the indication of the first unmanned aerial device participating in the first task.

26. The system of any of the above SYSTEM CLAUSES in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

circuitry for responding to an indication of the first unmanned aerial device becoming within a proximity of a mobile device by signaling the decision whether or not to cause the first unmanned aerial device to recognize the alias identifying the first unmanned aerial device as the automatic and conditional response to the indication of the first unmanned aerial device participating in the first task, the first unmanned aerial device having a sensor, the indication of the first unmanned aerial device becoming within a proximity of a mobile device including an indication of the mobile device being close enough to the sensor to be detected by the sensor.

27. The system of any of the above SYSTEM CLAUSES in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

circuitry for responding to an indication of the first unmanned aerial device becoming within a proximity of a mobile device by signaling the decision whether or not to cause the first unmanned aerial device to recognize the alias identifying the first unmanned aerial device as the automatic and conditional response to the indication of the first unmanned aerial device participating in the first task, the indication of the first unmanned aerial device becoming within a proximity of a mobile device including an indication of the first unmanned aerial device being close enough to the mobile device to be detected by the mobile device.

28. The system of any of the above SYSTEM CLAUSES in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

circuitry for causing a modular observation unit to be lifted and activated within at most about an hour of the modular observation unit becoming part of the first unmanned aerial device.

29. The system of any of the above SYSTEM CLAUSES in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

circuitry for signaling a decision whether or not to configure the first unmanned aerial device to continue observing a first person responsive to a prior observation of the first person, the prior observation of the first person having resulted from the first unmanned aerial device participating in the first task.

30. The system of any of the above SYSTEM CLAUSES in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

circuitry for causing the first unmanned aerial device to execute a delivery of a single dose of a therapeutic material to a human hand within one minute of an image capture of a portion of the human hand, the first task including the delivery of the single dose of the therapeutic material.

31. The system of any of the above SYSTEM CLAUSES in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

circuitry for configuring the first unmanned aerial device to execute a delivery of a particular material to a vicinity of a portable device within one minute of an image capture of the vicinity of the portable device, the first task including the delivery of the particular material to the vicinity of the portable device.

32. The system of any of the above SYSTEM CLAUSES in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

circuitry for causing the first unmanned aerial device to execute a delivery of a particular object to a human recipient contemporaneously with an image capture of a portion of the human recipient, the first task including the delivery of the particular object to the human recipient.

33. The system of any of the above SYSTEM CLAUSES in which the one or more articles of manufacture further comprise:

circuitry for causing the first unmanned aerial device to fly toward a home station in response to an indication of a specific person moving at least a threshold distance away from the first unmanned aerial device.

34. The system of any of the above SYSTEM CLAUSES in which the one or more articles of manufacture comprise:

the first unmanned aerial device, including circuitry for responding to a determination of whether or not a received signal expresses a first name of the first unmanned aerial device and whether or not the received signal expresses a second name of the first unmanned aerial device, the first name of the unmanned aerial device being the primary digital identifier, the second name of the unmanned aerial device being the alias.

35. A method comprising:

indicating a first unmanned aerial device participating in a first task; and signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device.

36. The method of any of the above METHOD CLAUSES in which the indicating a first unmanned aerial device participating in a first task comprises:

configuring the first unmanned aerial device to perform a first observation of a particular task in a first zone and a second unmanned aerial device to perform a second observation of the particular task in a second zone, the particular task being the first task.

37. The method of any of the above METHOD CLAUSES in which the indicating a first unmanned aerial device participating in a first task comprises:

configuring the first unmanned aerial device to capture normalcy-indicative data relating to a human subject as a component of the first task.

38. The method of any of the above METHOD CLAUSES in which the indicating a first unmanned aerial device participating in a first task comprises:

causing the first unmanned aerial device to undertake a performance observation task of a job that includes a performance task and the performance observation task, the performance observation task being the first task.

39. The method of any of the above METHOD CLAUSES in which the indicating a first unmanned aerial device participating in a first task comprises:

causing the first unmanned aerial device to undertake a performance observation task of a job that includes a performance task and the performance observation task, the performance observation task being the first task, the first task including invoking a pattern recognition module upon auditory data relating to the performance task.

40. The method of any of the above METHOD CLAUSES in which the indicating a first unmanned aerial device participating in a first task comprises:

transmitting a wireless signal indicative of a delivery of a package to a device associated with a recipient of the package, the wireless signal indicating at least one of the first unmanned aerial device or the package or a sender of the package, the first task including the delivery of the package to the recipient of the package.

41. The method of any of the above METHOD CLAUSES in which the indicating a first unmanned aerial device participating in a first task comprises:

transmitting a wireless signal indicative of a delivery of a package to a device associated with a recipient of the package, the wireless signal indicating at least one of the first unmanned aerial device or the package or a sender of the package, the first task including the delivery of the package to the recipient of the package, the wireless signal being a radio frequency signal indicating the sender of the package and also indicating at least one of the first unmanned aerial device or the package.

42. The method of any of the above METHOD CLAUSES in which the indicating a first unmanned aerial device participating in a first task comprises:

presenting navigation guidance via a display aboard the first unmanned aerial device while a primary motor of the first unmanned aerial device is not moving the first unmanned aerial device.

43. The method of any of the above METHOD CLAUSES in which the indicating a first unmanned aerial device participating in a first task comprises:

presenting navigation guidance via a display aboard the first unmanned aerial device while a primary motor of the first unmanned aerial device is not moving the first unmanned aerial device, the navigational guidance being presented via the display aboard the first unmanned aerial device while the first unmanned aerial device is stationary.

44. The method of any of the above METHOD CLAUSES in which the indicating a first unmanned aerial device participating in a first task comprises:

transmitting navigation guidance via a speaker of the first unmanned aerial device while a primary motor of the first unmanned aerial device is not moving the first unmanned aerial device.

45. The method of any of the above METHOD CLAUSES in which the indicating a first unmanned aerial device participating in a first task comprises:

transmitting navigation guidance via a speaker of the first unmanned aerial device while a primary motor of the first unmanned aerial device is not moving the first unmanned aerial device, the first unmanned aerial device having a rotor, the navigational guidance being transmitted via the speaker of the first unmanned aerial device while the primary motor is not turning the rotor.

46. The method of any of the above METHOD CLAUSES in which the indicating a first unmanned aerial device participating in a first task comprises:

identifying an operating mode of the first unmanned aerial device audibly or visibly while a primary motor of the first unmanned aerial device is not moving the first unmanned aerial device.

47. The method of any of the above METHOD CLAUSES in which the indicating a first unmanned aerial device participating in a first task comprises:

identifying an operating mode of the first unmanned aerial device audibly or visibly while a primary motor of the first unmanned aerial device is not moving the first unmanned aerial device, the operating mode of the first unmanned aerial device being a non-flight operating mode associated with the first task.

48. The method of any of the above METHOD CLAUSES in which the indicating a first unmanned aerial device participating in a first task comprises:

causing another unmanned aerial device to capture delivery data relating to the first unmanned aerial device.

49. The method of any of the above METHOD CLAUSES in which the indicating a first unmanned aerial device participating in a first task comprises:

configuring the first unmanned aerial device not to be equipped with any light sensors.

50. The method of any of the above METHOD CLAUSES in which the indicating a first unmanned aerial device participating in a first task comprises:

configuring the first unmanned aerial device not to be equipped with any light sensors, the first unmanned aerial device being operable to navigate without any light sensors.

51. The method of any of the above METHOD CLAUSES in which the indicating a first unmanned aerial device participating in a first task comprises:

causing a data handling device aboard the first unmanned aerial device to contain a task schedule indicating a first future delivery of a first object to a first destination and a second future delivery of a second object to a second destination.

52. The method of any of the above METHOD CLAUSES in which the indicating a first unmanned aerial device participating in a first task comprises:

determining whether or not an operator of the first unmanned aerial device has indicated a tracking mode of the first unmanned aerial device.

53. The method of any of the above METHOD CLAUSES in which the indicating a first unmanned aerial device participating in a first task comprises:

overriding a second task being performed by the first unmanned aerial device by transmitting a wireless signal indicative of the first task to the first unmanned aerial device.

54. The method of any of the above METHOD CLAUSES in which the indicating a first unmanned aerial device participating in a first task comprises:

overriding a second task being performed by the first unmanned aerial device by transmitting a wireless signal indicative of the first task to the first unmanned aerial device from or via a second unmanned aerial device.

55. The method of any of the above METHOD CLAUSES, further comprising:

configuring the first unmanned aerial device to transmit a wireless signal indicative of having performed a particular task and not to store any indication of having performed the particular task, the particular task being the first task.

56. The method of any of the above METHOD CLAUSES, further comprising:
    signaling a decision whether or not to reserve a space for a passenger vehicle as a component of the first task.

57. The method of any of the above METHOD CLAUSES, further comprising:
    signaling a decision whether or not to reserve a space for a passenger vehicle as a component of the first task by transmitting the decision to the first unmanned aerial device after the decision has been received from a person aboard the passenger vehicle.

58. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
    signaling a decision whether or not to reserve a specific resource by associating the specific resource with the first unmanned aerial device or with a specific person.

59. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
    responding to an indication of the first unmanned aerial device becoming within a proximity of a mobile device by signaling the decision whether or not to cause the first unmanned aerial device to recognize the alias identifying the first unmanned aerial device as the automatic and conditional response to the indication of the first unmanned aerial device participating in the first task.

60. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
    causing a modular observation unit to be lifted and activated within at most about an hour of the modular observation unit becoming part of the first unmanned aerial device.

61. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
    causing a modular observation unit to be lifted and activated within at most about an hour of the modular observation unit becoming part of the first unmanned aerial device, the modular observation unit being lifted responsive to an indication of the modular observation unit becoming part of the first unmanned aerial device.

62. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
    causing a modular observation unit to be lifted and activated within at most about an hour of the modular observation unit becoming part of the first unmanned aerial device, the modular observation unit being activated responsive to an indication of the modular observation unit becoming part of the first unmanned aerial device.

63. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
    signaling a decision whether or not to configure the first unmanned aerial device to continue observing a first person responsive to a prior observation of the first person, the prior observation of the first person having resulted from the first unmanned aerial device participating in the first task.

64. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
    signaling a decision whether or not to configure the first unmanned aerial device to continue observing a first person responsive to a prior observation of the first person, the prior observation of the first person having resulted from the first unmanned aerial device participating in the first task, the decision being an affirmative decision to configure the first unmanned aerial device to continue observing the first person if a pattern recognition module indicates an abnormality relating to the first person and the decision otherwise generally being a negative decision.

65. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
    causing the first unmanned aerial device to execute a delivery of a single dose of a therapeutic material to a human hand within one minute of an image capture of a portion of the human hand, the first task including the delivery of the single dose of the therapeutic material.

66. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
    causing the first unmanned aerial device to execute a delivery of a single dose of a therapeutic material to a human hand within one minute of an image capture of a portion of the human hand, the first task including the delivery of the single dose of the therapeutic material, the single dose of the therapeutic material including at least one of a capsule or a syringe, the first unmanned aerial device executing the delivery of the single dose of the therapeutic material to the human hand while a stationary or pivotable camera records video data depicting the human hand, the image capture being a component of the stationary or pivotable camera recording the video data.

67. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

configuring the first unmanned aerial device to execute a delivery of a particular material to a vicinity of a portable device within one minute of an image capture of the vicinity of the portable device, the first task including the delivery of the particular material to the vicinity of the portable device.

68. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

configuring the first unmanned aerial device to execute a delivery of a particular material to a vicinity of a portable device within one minute of an image capture of the vicinity of the portable device, the first task including the delivery of the particular material to the vicinity of the portable device, the particular material comprising a medical product, the first unmanned aerial device executing the delivery of the particular material to the vicinity of the portable device while a camera records video data depicting the vicinity of the portable device, the image capture of the vicinity of the portable device being a component of the camera recording video data depicting the vicinity of the portable device.

69. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

causing the first unmanned aerial device to execute a delivery of a particular object to a human recipient contemporaneously with an image capture of a portion of the human recipient, the first task including the delivery of the particular object to the human recipient.

70. The method of any of the above METHOD CLAUSES in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:

causing the first unmanned aerial device to execute a delivery of a particular object to a human recipient contemporaneously with an image capture of a portion of the human recipient, the first task including the delivery of the particular object to the human recipient, the particular object comprising at least one of a processor or an application specific integrated circuit, the first unmanned aerial device executing the delivery of the particular object to the human recipient while a camera records video data depicting the portion of the human recipient, the image capture of the portion of the human recipient being a component of the camera recording video data, the video data depicting at least a facial portion of the human recipient as the portion of the human recipient.

71. The method of any of the above METHOD CLAUSES, further comprising:

causing the first unmanned aerial device to fly toward a home station in response to an indication of a specific person moving at least a threshold distance away from the first unmanned aerial device.

72. The method of any of the above METHOD CLAUSES, further comprising:

causing the first unmanned aerial device to fly toward a home station in response to an indication of a specific person moving at least a threshold distance away from the first unmanned aerial device, the specific person being an operator of the unmanned aerial device.

73. The method of any of the above METHOD CLAUSES, further comprising:

responding to a determination of whether or not a received signal expresses a first name of the first unmanned aerial device and whether or not the received signal expresses a second name of the first unmanned aerial device.

74. The method of any of the above METHOD CLAUSES, further comprising:

responding to a determination of whether or not a received signal expresses a first name of the first unmanned aerial device and whether or not the received signal expresses a second name of the first unmanned aerial device, the first name of the first unmanned aerial device being the primary digital identifier of the first unmanned aerial device, the second name of the first unmanned aerial device being the alias of the first unmanned aerial device.

75. (Independent) A method comprising:

obtaining first data indicating that a first unmanned aerial device delivered a first item to a first entity; and transmitting via a free space medium the first data to a provider of the first item as an automatic and conditional response to the first data indicating that the first unmanned aerial device delivered the first item to the first entity, the first data indicating at least one of the first item or the first entity or the first unmanned aerial device.

76. The method of CLAUSE 75 further comprising:

performing the operation(s) of any one or more of the above METHOD CLAUSES that depend from METHOD CLAUSE 35.

77. (Independent) A method comprising:

obtaining first position data from a first entity, by a second entity, the first entity being a first unmanned aerial device; and signaling a decision whether or not to allocate a first resource to the second entity after the first position data passes from the first unmanned aerial device to the second entity, the first resource being associated with the first position data.

78. The method of CLAUSE 77 further comprising:

performing the operation(s) of any one or more of the above METHOD CLAUSES that depend from METHOD CLAUSE 35.

79. (Independent) A method comprising:

causing a first unmanned aerial device to guide a first individual to a first destination; and causing the first unmanned aerial device to fly to a second destination as an automatic and conditional response to an indication of the first individual arriving at the first destination.

80. The method of CLAUSE 79 further comprising:

performing the operation(s) of any one or more of the above METHOD CLAUSES that depend from METHOD CLAUSE 35.

81. (Independent) A method comprising:

obtaining a tracking mode of a delivery task of a first unmanned aerial device; and signaling a decision whether or not to omit a record of the first unmanned aerial device completing the delivery task of the first unmanned aerial device as an automatic and conditional response to the tracking mode of the delivery task of the first unmanned aerial device.

82. The method of CLAUSE 81 further comprising:

performing the operation(s) of any one or more of the above METHOD CLAUSES that depend from METHOD CLAUSE 35.

83. (Independent) A system comprising:

means for performing the operation(s) of any one or more of the above METHOD CLAUSES.

84. (Independent) An article of manufacture comprising:

one or more physical media configured to bear a device-detectable implementation of a method including at least indicating a first unmanned aerial device participating in a first task; and signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device.

85. The article of manufacture of CLAUSE 84 in which a portion of the one or more physical media comprises:

one or more signal-bearing media configured to transmit one or more instructions for performing the operation(s) of any one or more of the above METHOD CLAUSES.

86. (Independent) An article of manufacture comprising:

one or more physical media bearing a device-detectable output indicating an occurrence of indicating a first unmanned aerial device participating in a first task; and signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device.

87. The article of manufacture of CLAUSE 86 in which a portion of the one or more physical media comprises:

one or more physical media bearing a device-detectable output indicating an occurrence of performing the operation(s) of any one or more of the above METHOD CLAUSES.

All of the patents and other publications referred to above (not including websites) are incorporated herein by reference generally—including those identified in relation to particular new applications of existing techniques—to the extent not inconsistent herewith. While various system, method, article of manufacture, or other embodiments or aspects have been disclosed above, also, other combinations of embodiments or aspects will be apparent to those skilled in the art in view of the above disclosure. The various embodiments and aspects disclosed above are for purposes of illustration and are not intended to be limiting, with the true scope and spirit being indicated in the final claim set that follows.

What is claimed is:

1. A system comprising: one or more articles of manufacture including circuitry for indicating a first unmanned aerial device participating in a first task, the circuitry for indicating a first unmanned aerial device participating in a first task including:

circuitry for causing a data handling device associated with the first unmanned aerial device to contain a task schedule indicating a first future delivery of a first object to a first destination, the data handling device aboard the first unmanned aerial device comprising at least one of a disk drive or a volatile memory;

circuitry for transmitting navigation guidance via at least one of a speaker or a light indicator of the first unmanned aerial device while a primary mover of the first unmanned aerial device is not actively moving the first unmanned aerial device;

circuitry for identifying an operating mode related to a current or future movement of the first unmanned aerial device audibly or visibly while the primary mover of the first unmanned aerial device is not actively moving the first unmanned aerial device;

circuitry for transmitting a wireless signal indicative of a delivery of a package to at least one address associated with a device associated with a recipient of the package, the wireless signal indicating at least one of the first unmanned aerial device or the package or a sender of the package, the package including the first object, the first task including the delivery of the package to the recipient; and circuitry for requesting another unmanned aerial device to capture delivery depicting data relating to the first unmanned aerial device, the delivery depicting data relating to the first unmanned aerial device depicting at least one of the first unmanned aerial device or a vicinity of the first unmanned aerial device; and and circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device.

2. The system of claim 1 in which the circuitry for indicating a first unmanned aerial device participating in a first task comprises:

circuitry for configuring the first unmanned aerial device to perform a first observation of a particular task in a first zone and a second unmanned aerial device to perform a second observation of the particular task in a second zone, the particular task being the first task.

3. The system of claim 1 in which the circuitry for indicating a first unmanned aerial device participating in a first task comprises:

circuitry for configuring the first unmanned aerial device to perform a first observation of a particular task in a first zone and a second unmanned aerial device to perform a second observation of the particular task in a second zone, the particular task being the first task, the first zone and the second zone sharing a common boundary.

4. The system of claim 1 in which the circuitry for indicating a first unmanned aerial device participating in a first task comprises:

circuitry for configuring the first unmanned aerial device to capture normalcy-indicative data relating to a human subject as a component of the first task, at least some of the normalcy-indicative data being indicative of a speech rate or a movement rate of the human subject.

5. The system of claim 1 in which the circuitry for indicating a first unmanned aerial device participating in a first task comprises:
   circuitry for presenting navigation guidance via a display aboard the first unmanned aerial device while a primary motor of the first unmanned aerial device is not moving the first unmanned aerial device.

6. The system of claim 1 in which the circuitry for indicating a first unmanned aerial device participating in a first task comprises:
   circuitry for configuring the first unmanned aerial device not to be equipped with any light sensors, the circuitry for configuring the first unmanned aerial device not to be equipped with any light sensors being operably coupled with a releasable mechanical linkage, the releasable mechanical linkage being configured to support a data handling unit, the data handling unit including at least one light sensor.

7. The system of claim 1 in which the circuitry for indicating a first unmanned aerial device participating in a first task comprises:
   circuitry for determining whether or not an operator of the first unmanned aerial device has indicated a tracking mode of the first unmanned aerial device.

8. The system of claim 1 in which the circuitry for indicating a first unmanned aerial device participating in a first task comprises:
   circuitry for overriding a second task being performed by the first unmanned aerial device by transmitting a wireless signal indicative of the first task to the first unmanned aerial device.

9. The system of claim 1 in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
   circuitry for signaling a decision whether or not to reserve a specific resource by associating the specific resource with the first unmanned aerial device or with a specific person.

10. The system of claim 1 in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
   circuitry for signaling a decision whether or not to reserve a specific resource by associating the specific resource with the first unmanned aerial device or with a specific person, the decision being an affirmative decision to reserve the specific resource, the specific resource including at least one of a space or a material.

11. The system of claim 1 which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
   circuitry for causing a modular observation unit to be lifted and activated within at most about an hour of the modular observation unit becoming part of the first unmanned aerial device.

12. The system of claim 1 in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
   circuitry for signaling a decision whether or not to configure the first unmanned aerial device to continue observing a first person responsive to a prior observation of the first person, the prior observation of the first person having resulted from the first unmanned aerial device participating in the first task.

13. The system of claim 1 in which the circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
   circuitry for causing the first unmanned aerial device to execute a delivery of a particular object to a human recipient contemporaneously with an image capture of a portion of the human recipient, the first task including the delivery of the particular object to the human recipient.

14. The system of claim 1 in which the one or more articles of manufacture comprise:
   the first unmanned aerial device, including circuitry for responding to a determination of whether or not a received signal expresses a first name of the first unmanned aerial device and whether or not the received signal expresses a second name of the first unmanned aerial device, the first name of the unmanned aerial device being the primary digital identifier, the second name of the unmanned aerial device being the alias.

15. The system of claim 1 in which the one or more articles of manufacture further comprise:
   a vehicle having one or more wheels, the vehicle configured to support the circuitry for signaling the decision whether or not to cause the first unmanned aerial device to recognize the alias identifying the first unmanned aerial device as the automatic and conditional response to the indication of the first unmanned aerial device participating in the first task, the alias being different than the primary digital identifier of the first unmanned aerial device.

16. The system of claim 1 in which the circuitry for indicating a first unmanned aerial device participating in a first task comprises:
   circuitry for overriding a second task being performed by the first unmanned aerial device by transmitting a wireless signal indicative of the first task to the first unmanned aerial device;
   circuitry for configuring the first unmanned aerial device to capture normalcy-indicative data relating to a human subject as a component of the first task, at least some of the normalcy-indicative data being indicative of a biometric, the biometric being an abnormal or normal rate, the abnormal or normal rate being a respiration rate or a heart rate of the human subject;

circuitry for configuring the first unmanned aerial device to perform a first observation of a particular task in a first zone and a second unmanned aerial device to perform a second observation of the particular task in a second zone, the particular task being the first task, the first zone and the second zone sharing a common boundary; and circuitry for determining whether or not an operator of the first unmanned aerial device has indicated a tracking mode of the first unmanned aerial device.

17. The system of claim 1 in which the one or more articles of manufacture comprise:

a handheld device, including the circuitry for indicating the first unmanned aerial device participating in the first task and including the circuitry for signaling the decision whether or not to cause the first unmanned aerial device to recognize the alias identifying the first unmanned aerial device as the automatic and conditional response to the indication of the first unmanned aerial device participating in the first task, the alias being different than the primary digital identifier of the first unmanned aerial device, in which the circuitry for signaling the decision whether or not to cause the first unmanned aerial device to recognize the alias identifying the first unmanned aerial device as the automatic and conditional response to an indication of the first unmanned aerial device participating in the first task includes circuitry for configuring the first unmanned aerial device to execute a delivery of a particular material to a vicinity of another device within one minute of an image capture of the vicinity of the other device, the first task including the delivery of the particular material to the vicinity of the other device; and circuitry for responding to an indication of the first unmanned aerial device becoming within a proximity of the other device by signaling the decision whether or not to cause the first unmanned aerial device to recognize the alias identifying the first unmanned aerial device as the automatic and conditional response to the indication of the first unmanned aerial device participating in the first task, the indication of the first unmanned aerial device becoming within a proximity of the other device including an indication of the first unmanned aerial device being close enough to the other device to be detected by the other device.

18. The system of claim 1 in which the one or more articles of manufacture comprise:

circuitry for causing a modular observation unit to be lifted and activated within at most about an hour of the modular observation unit becoming part of the first unmanned aerial device;

circuitry for responding to an indication of the first unmanned aerial device becoming within a proximity of a mobile device by signaling the decision whether or not to cause the first unmanned aerial device to recognize the alias identifying the first unmanned aerial device as the automatic and conditional response to the indication of the first unmanned aerial device participating in the first task, the first unmanned aerial device having a sensor, the indication of the first unmanned aerial device becoming within a proximity of a mobile device including an indication of the mobile device being close enough to the sensor to be detected by the sensor;

circuitry for signaling a decision whether or not to reserve a specific resource by associating the specific resource with the first unmanned aerial device or with a human recipient, the specific resource including a particular object;

circuitry for causing the first unmanned aerial device to execute a delivery of the particular object to the human recipient contemporaneously with an image capture of a portion of the human recipient, the first task including the delivery of the particular object to the human recipient; and circuitry for signaling a decision whether or not to configure the first unmanned aerial device to continue observing a first person responsive to a prior observation of the first person, the prior observation of the first person having resulted from the first unmanned aerial device participating in the first task, the first person being the human recipient.

19. A system comprising: one or more articles of manufacture including means for indicating a first unmanned aerial device participating in a first task, the means for indicating a first unmanned aerial device participating in a first task including:

means for causing a data handling device associated with the first unmanned aerial device to contain a task schedule indicating a first future delivery of a first object to a first destination, the data handling device aboard the first unmanned aerial device comprising at least one of a disk drive or a volatile memory;

means for transmitting navigation guidance via at least one of a speaker or a light indicator of the first unmanned aerial device while a primary mover of the first unmanned aerial device is not actively moving the first unmanned aerial device;

means for identifying an operating mode related to a current or future movement of the first unmanned aerial device audibly or visibly while the primary mover of the first unmanned aerial device is not actively moving the first unmanned aerial device;

means for transmitting a wireless signal indicative of a delivery of a package to at least one address associated with a device associated with a recipient of the package, the wireless signal indicating at least one of the first unmanned aerial device or the package or a sender of the package, the package including the first object, the first task including the delivery of the package to the recipient; and means for requesting another unmanned aerial device to capture delivery depicting data relating to the first unmanned aerial device, the delivery depicting data relating to the first unmanned aerial device depicting at least one of the first unmanned aerial device or a vicinity of the first unmanned aerial device; and means for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device.

20. The system of claim 19 in which the one or more articles of manufacture comprise:

the first unmanned aerial device, including means for responding to a determination of whether or not a received signal expresses a first name of the first unmanned aerial device and whether or not the received signal expresses a second name of the first unmanned aerial device, the first name of the unmanned aerial device being the primary digital identifier, the second name of the unmanned aerial device being the alias.

21. A method comprising:
indicating, via at least one machine state, a first unmanned aerial device participating in a first task, the indicating including:
causing a data handling device associated with the first unmanned aerial device to contain a task schedule indicating a first future delivery of a first object to a first destination, the data handling device aboard the first unmanned aerial device comprising at least one of a disk drive or a volatile memory;
transmitting navigation guidance via at least one of a speaker or a light indicator of the first unmanned aerial device while a primary mover of the first unmanned aerial device is not actively moving the first unmanned aerial device;
identifying an operating mode related to a current or future movement of the first unmanned aerial device audibly or visibly while the primary mover of the first unmanned aerial device is not actively moving the first unmanned aerial device;
transmitting a wireless signal indicative of a delivery of a package to at least one address associated with a device associated with a recipient of the package, the wireless signal indicating at least one of the first unmanned aerial device or the package or a sender of the package, the package including the first object, the first task including the delivery of the package to the recipient; and
requesting another unmanned aerial device to capture delivery depicting data relating to the first unmanned aerial device, the delivery depicting data relating to the first unmanned aerial device depicting at least one of the first unmanned aerial device or a vicinity of the first unmanned aerial device; and
invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device.

22. The method of claim 21 in which the invoking circuitry for signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device, comprises:
causing the first unmanned aerial device to execute a delivery of a single dose of a therapeutic material to a human hand within one minute of an image capture of a portion of the human hand, the first task including the delivery of the single dose of the therapeutic material.

23. The method of claim 21, wherein the indicating via at least one machine state includes:
indicating via at least one of a state or a state transition of electrical circuitry.

24. The method of claim 23, wherein the indicating via at least one of a state or state transition of electrical circuitry includes:
indicating via at least one of a state or a state transition of at least one of an application specific integrated circuit (ASIC), or a programmable gate array.

25. The method of claim 23, wherein the indicating via at least one of a state or state transition of electrical circuitry includes:
indicating via at least one of a state or a state transition of at least one very-large-scale integrated circuit (VLSIC) configured by at least one program.

26. An article of manufacture comprising:
one or more physical media configured to bear a device-detectable implementation of a method including at least indicating a first unmanned aerial device participating in a first task, the indicating a first unmanned aerial device participating in a first task including:
causing a data handling device associated with the first unmanned aerial device to contain a task schedule indicating a first future delivery of a first object to a first destination, the data handling device aboard the first unmanned aerial device comprising at least one of a disk drive or a volatile memory;
transmitting navigation guidance via at least one of a speaker or a light indicator of the first unmanned aerial device while a primary mover of the first unmanned aerial device is not actively moving the first unmanned aerial device:
identifying an operating mode of the first unmanned aerial device audibly or visibly while the primary motor of the first unmanned aerial device is not moving the first unmanned aerial device;
transmitting a wireless signal indicative of a delivery of a package to at least one address associated with a device associated with a recipient of the package, the wireless signal indicating at least one of the first unmanned aerial device or the package or a sender of the package, the package including the first object, the first task including the delivery of the package to the recipient; and
requesting another unmanned aerial device to capture delivery depicting data relating to the first unmanned aerial device, the delivery depicting data relating to the first unmanned aerial device depicting at least one of the first unmanned aerial device or a vicinity of the first unmanned aerial device; and
signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device.

27. The article of manufacture of claim 26 in which a portion of the one or more physical media comprises:
one or more signal-bearing media configured to transmit one or more instructions for
causing the first unmanned aerial device to undertake a performance observation task of a job that includes a performance task and the performance observation task.

28. An article of manufacture comprising:
one or more physical media bearing a device-detectable outcome indicating an occurrence of
indicating a first unmanned aerial device participating in a first task, the indicating a first unmanned aerial device participating in a first task including:
causing a data handling device associated with the first unmanned aerial device to contain a task schedule indicating a first future delivery of a first object to a first destination, the data handling device aboard the first unmanned aerial device comprising at least one of a disk drive or a volatile memory;

transmitting navigation guidance via at least one of a speaker or a light indicator of the first unmanned aerial device while a primary mover of the first unmanned aerial device is not actively moving the first unmanned aerial device;

identifying an operating mode related to a current or future movement of the first unmanned aerial device audibly or visibly while the primary mover of the first unmanned aerial device is not actively moving the first unmanned aerial device;

transmitting a wireless signal indicative of a delivery of a package to at least one address associated with a device associated with a recipient of the package, the wireless signal indicating at least one of the first unmanned aerial device or the package or a sender of the package, the package including the first object, the first task including the delivery of the package to the recipient; and requesting another unmanned aerial device to capture delivery depicting data relating to the first unmanned aerial device, the delivery depicting data relating to the first unmanned aerial device depicting at least one of the first unmanned aerial device or a vicinity of the first unmanned aerial device; and signaling a decision whether or not to cause the first unmanned aerial device to recognize an alias identifying the first unmanned aerial device as an automatic and conditional response to an indication of the first unmanned aerial device participating in the first task, the alias being different than a primary digital identifier of the first unmanned aerial device.

29. The article of manufacture of claim 28 in which a portion of the one or more physical media comprises:

one or more physical media bearing a device-detectable output indicating an occurrence of signaling a decision whether or not to configure the first unmanned aerial device to continue observing a first person responsive to a prior observation of the first person.

\* \* \* \* \*